United States Patent
Shelton, IV et al.

(10) Patent No.: US 11,992,200 B2
(45) Date of Patent: May 28, 2024

(54) INSTRUMENT CONTROL SURGICAL IMAGING SYSTEMS

(71) Applicant: Cilag GmbH International, Zug (CH)

(72) Inventors: Frederick E. Shelton, IV, Hillsboro, OH (US); Charles J. Scheib, Loveland, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 28 days.

(21) Appl. No.: 17/449,769

(22) Filed: Oct. 1, 2021

(65) Prior Publication Data
US 2023/0097151 A1    Mar. 30, 2023

Related U.S. Application Data

(60) Provisional application No. 63/249,980, filed on Sep. 29, 2021.

(51) Int. Cl.
*A61B 1/00* (2006.01)
*A61B 1/313* (2006.01)
(Continued)

(52) U.S. Cl.
CPC ...... *A61B 17/0218* (2013.01); *A61B 1/00004* (2013.01); *A61B 1/00006* (2013.01);
(Continued)

(58) Field of Classification Search
CPC .......... A61B 1/00006; A61B 1/000095; A61B 1/00045; A61B 1/3132; A61B 34/20;
(Continued)

(56) References Cited

U.S. PATENT DOCUMENTS 4,445,892 A    5/1984    Hussein et al.
4,470,407 A    9/1984    Hussein
(Continued)

FOREIGN PATENT DOCUMENTS

CA    2978771 A1    10/2016
EP    2226026 A1    9/2010
(Continued)

OTHER PUBLICATIONS

International Search Report and Written Opinion for International Application No. PCT/IB2022/059103, dated Jan. 2, 2023, 16 pages.
(Continued)

*Primary Examiner* — Timothy J Neal
(74) *Attorney, Agent, or Firm* — Mintz Levin Cohn Ferris Glovsky and Popeo, P.C.

(57) ABSTRACT

Surgical systems are provided. The surgical system includes a first scope device configured to transmit image data of a first scene within a field of view of the first scope device. A second scope device is configured to transmit image data of a second scene within a field of view of the second scope device. A tracking device is associated with one of the scope devices and configured to transmit a signal indicative of a location of the one of the scope devices. A controller is configured to receive the transmitted image data and the transmitted signal to determine a relative distance between the scope devices and to provide a merged image of at least a portion of the scope devices in a single scene, where at least one of the scope devices in the merged image is a representative depiction.

20 Claims, 43 Drawing Sheets

(51) Int. Cl.
| | |
|---|---|
| *A61B 17/00* | (2006.01) |
| *A61B 17/02* | (2006.01) |
| *A61B 17/12* | (2006.01) |
| *A61B 17/34* | (2006.01) |
| *A61B 34/20* | (2016.01) |
| *A61B 34/30* | (2016.01) |
| *A61B 90/00* | (2016.01) |
| *A61B 90/50* | (2016.01) |
| *G06T 7/73* | (2017.01) |
| *H04N 13/111* | (2018.01) |
| *H04N 13/156* | (2018.01) |
| *A61B 5/00* | (2006.01) |

(52) U.S. Cl.
CPC .... *A61B 1/00009* (2013.01); *A61B 1/000095* (2022.02); *A61B 1/00045* (2013.01); *A61B 1/00048* (2013.01); *A61B 1/0005* (2013.01); *A61B 1/3132* (2013.01); *A61B 17/00234* (2013.01); *A61B 17/12099* (2013.01); *A61B 17/12104* (2013.01); *A61B 17/12136* (2013.01); *A61B 17/3421* (2013.01); *A61B 17/3474* (2013.01); *A61B 34/20* (2016.02); *A61B 34/30* (2016.02); *A61B 90/06* (2016.02); *A61B 90/361* (2016.02); *A61B 90/37* (2016.02); *A61B 90/39* (2016.02); *A61B 90/50* (2016.02); *G06T 7/74* (2017.01); *H04N 13/111* (2018.05); *H04N 13/156* (2018.05); *A61B 5/0075* (2013.01); *A61B 2017/00022* (2013.01); *A61B 2017/00057* (2013.01); *A61B 2017/00061* (2013.01); *A61B 2017/00075* (2013.01); *A61B 2017/00199* (2013.01); *A61B 2017/00292* (2013.01); *A61B 2017/00809* (2013.01); *A61B 2017/00818* (2013.01); *A61B 2017/3419* (2013.01); *A61B 2017/3484* (2013.01); *A61B 2034/2055* (2016.02); *A61B 2034/2057* (2016.02); *A61B 2034/301* (2016.02); *A61B 2090/064* (2016.02); *A61B 2090/3937* (2016.02); *A61B 2090/3945* (2016.02); *G06T 2207/10068* (2013.01)

(58) Field of Classification Search
CPC ............ A61B 34/30; A61B 2034/2055; A61B 2034/301; A61B 1/00193; A61B 1/00172; A61B 1/0638; A61B 1/05; A61B 1/06; A61B 1/04; A61B 1/046; A61B 1/0605; A61B 1/009; A61B 1/00194; A61B 1/000094; A61B 17/0482; A61B 1/00013; A61B 5/0084; A61B 1/00055; A61B 17/1114; A61B 1/00149; A61B 1/07; A61B 90/361; A61B 5/0086; A61B 90/30; A61B 1/00009; A61B 1/043; A61B 5/0036; A61B 5/0075; A61B 17/1155; A61B 90/37; A61B 1/053; G06T 7/0012; G06T 2207/10068; G06T 1/0007; G01S 17/36; G16H 40/63; G16H 20/40; G02F 1/1326; G01B 11/2513

See application file for complete search history.

(56) References Cited

U.S. PATENT DOCUMENTS

| | | | |
|---|---|---|---|
| 5,505,700 A | 4/1996 | Leone et al. | |
| 6,004,271 A | 12/1999 | Moore | |
| 6,503,195 B1* | 1/2003 | Keller | G06T 7/521 348/45 |
| 6,530,913 B1 | 3/2003 | Giba et al. | |
| 6,544,230 B1 | 4/2003 | Flaherty et al. | |
| 6,610,007 B2 | 8/2003 | Belson et al. | |
| 6,669,709 B1 | 12/2003 | Cohn et al. | |
| 6,905,460 B2 | 6/2005 | Wang et al. | |
| 7,371,210 B2 | 5/2008 | Brock et al. | |
| 8,052,636 B2 | 11/2011 | Moll et al. | |
| 8,068,649 B2 | 11/2011 | Green | |
| 8,257,303 B2 | 9/2012 | Moll et al. | |
| 8,517,933 B2 | 8/2013 | Mohr | |
| 8,545,515 B2 | 10/2013 | Prisco et al. | |
| 8,551,115 B2 | 10/2013 | Steger et al. | |
| 8,623,028 B2 | 1/2014 | Rogers et al. | |
| 8,771,180 B2 | 7/2014 | Mohr | |
| 8,831,782 B2 | 9/2014 | Itkowitz | |
| 8,888,789 B2 | 11/2014 | Prisco et al. | |
| 9,254,178 B2 | 2/2016 | Prisco et al. | |
| 9,269,682 B2 | 2/2016 | Yu et al. | |
| 9,274,047 B2 | 3/2016 | Velten et al. | |
| 9,283,050 B2 | 3/2016 | Prisco et al. | |
| 9,320,416 B2 | 4/2016 | Cooper et al. | |
| 9,339,341 B2 | 5/2016 | Cooper | |
| 9,358,074 B2 | 6/2016 | Schena et al. | |
| 9,572,481 B2 | 2/2017 | Duindam et al. | |
| 9,636,186 B2 | 5/2017 | Kumar et al. | |
| 9,861,271 B2 | 1/2018 | Liu et al. | |
| 10,245,069 B2 | 4/2019 | Rogers et al. | |
| 10,456,202 B2* | 10/2019 | Sholev | A61B 90/53 |
| 10,492,665 B2 | 12/2019 | Dejima | |
| 10,792,034 B2 | 10/2020 | Scheib et al. | |
| 10,925,598 B2 | 2/2021 | Scheib et al. | |
| 11,051,876 B2 | 7/2021 | Shelton, IV et al. | |
| 2001/0009976 A1 | 7/2001 | Panescu et al. | |
| 2001/0029366 A1 | 10/2001 | Swanson et al. | |
| 2002/0087169 A1 | 7/2002 | Brock et al. | |
| 2002/0177789 A1 | 11/2002 | Ferry et al. | |
| 2003/0074011 A1 | 4/2003 | Gilboa et al. | |
| 2003/0135204 A1 | 7/2003 | Lee et al. | |
| 2004/0176751 A1 | 9/2004 | Weitzner et al. | |
| 2004/0193146 A1 | 9/2004 | Lee et al. | |
| 2005/0182295 A1 | 8/2005 | Soper et al. | |
| 2007/0060879 A1 | 3/2007 | Weitzner et al. | |
| 2007/0162106 A1 | 7/2007 | Evans et al. | |
| 2008/0243142 A1* | 10/2008 | Gildenberg | G16H 30/40 606/130 |
| 2008/0300592 A1 | 12/2008 | Weitzner et al. | |
| 2009/0012618 A1 | 1/2009 | Ahrens et al. | |
| 2009/0054884 A1 | 2/2009 | Farley et al. | |
| 2009/0171196 A1 | 7/2009 | Hauck et al. | |
| 2010/0081881 A1 | 4/2010 | Murray et al. | |
| 2010/0228096 A1 | 9/2010 | Weisenburgh, II et al. | |
| 2010/0240960 A1 | 9/2010 | Richard | |
| 2010/0312063 A1 | 12/2010 | Hess et al. | |
| 2010/0312065 A1 | 12/2010 | Shelton, IV et al. | |
| 2011/0152788 A1 | 6/2011 | Hotter | |
| 2011/0295074 A1 | 12/2011 | Stefanchik et al. | |
| 2012/0130188 A1 | 5/2012 | Okoniewski | |
| 2013/0266029 A1 | 10/2013 | Yi et al. | |
| 2014/0066717 A1 | 3/2014 | Rogers et al. | |
| 2014/0194732 A1 | 7/2014 | Nakaguchi | |
| 2015/0145953 A1* | 5/2015 | Fujie | A61B 90/37 348/45 |
| 2016/0007979 A1 | 1/2016 | Bhagat et al. | |
| 2016/0331473 A1* | 11/2016 | Yamamura | A61B 1/005 |
| 2017/0024903 A1* | 1/2017 | Razzaque | A61B 6/5247 |
| 2017/0055819 A1 | 3/2017 | Hansen et al. | |
| 2017/0086653 A1 | 3/2017 | Yeung et al. | |
| 2017/0128041 A1 | 5/2017 | Hasser et al. | |
| 2017/0128144 A1 | 5/2017 | Hasser et al. | |
| 2017/0128145 A1 | 5/2017 | Hasser et al. | |
| 2017/0172662 A1 | 6/2017 | Panescu et al. | |
| 2017/0181808 A1 | 6/2017 | Panescu et al. | |
| 2017/0251900 A1 | 9/2017 | Hansen et al. | |
| 2018/0042680 A1* | 2/2018 | DiMaio | G16H 20/40 |
| 2018/0049821 A1 | 2/2018 | Shelton, IV et al. | |
| 2018/0070800 A1 | 3/2018 | Yeung et al. | |
| 2018/0177556 A1 | 6/2018 | Noonan | |
| 2018/0256008 A1* | 9/2018 | Nishizawa | A61B 1/05 |
| 2018/0276877 A1* | 9/2018 | Mountney | A61B 34/20 |
| 2018/0296280 A1 | 10/2018 | Kurihara et al. | |
| 2018/0325604 A1 | 11/2018 | Atarot et al. | |

(56) References Cited

U.S. PATENT DOCUMENTS

| | | |
|---|---|---|
| 2019/0117209 A1 | 4/2019 | Augelli et al. |
| 2019/0200844 A1 | 7/2019 | Shelton, IV et al. |
| 2019/0200981 A1 | 7/2019 | Harris et al. |
| 2019/0201046 A1 | 7/2019 | Shelton, IV et al. |
| 2019/0201088 A1 | 7/2019 | Shelton, IV et al. |
| 2019/0201114 A1 | 7/2019 | Shelton, IV et al. |
| 2019/0201136 A1 | 7/2019 | Shelton, IV et al. |
| 2019/0201140 A1 | 7/2019 | Yates et al. |
| 2019/0204201 A1 | 7/2019 | Shelton, IV et al. |
| 2019/0206004 A1 | 7/2019 | Shelton, IV et al. |
| 2019/0206555 A1 | 7/2019 | Morgan et al. |
| 2019/0207857 A1 | 7/2019 | Shelton, IV et al. |
| 2019/0290247 A1* | 9/2019 | Popovic ............ A61B 1/0005 |
| 2020/0000530 A1 | 1/2020 | Defonzo et al. |
| 2020/0015668 A1 | 1/2020 | Scheib |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015902 A1 | 1/2020 | Scheib et al. |
| 2020/0015903 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015923 A1 | 1/2020 | Scheib et al. |
| 2020/0015924 A1 | 1/2020 | Scheib et al. |
| 2020/0015925 A1 | 1/2020 | Scheib |
| 2020/0037863 A1 | 2/2020 | Harris et al. |
| 2020/0060524 A1 | 2/2020 | Weitzner |
| 2020/0085516 A1 | 3/2020 | Defonzo et al. |
| 2020/0170720 A1 | 6/2020 | Ummalaneni |
| 2020/0178948 A1 | 6/2020 | Piskun et al. |
| 2020/0188043 A1 | 6/2020 | Yu et al. |
| 2020/0222078 A1 | 7/2020 | Dharan et al. |
| 2020/0306004 A1 | 10/2020 | Batchelor et al. |
| 2020/0315723 A1* | 10/2020 | Hassan ............... A61B 34/74 |
| 2021/0085410 A1 | 3/2021 | Hassan |
| 2021/0196108 A1 | 7/2021 | Shelton, IV et al. |
| 2021/0196109 A1 | 7/2021 | Shelton, IV et al. |
| 2021/0196381 A1 | 7/2021 | Eckert et al. |
| 2021/0196383 A1 | 7/2021 | Shelton, IV et al. |
| 2021/0196384 A1 | 7/2021 | Shelton, IV et al. |
| 2021/0196385 A1 | 7/2021 | Shelton, IV et al. |
| 2021/0196386 A1 | 7/2021 | Shelton, IV et al. |
| 2021/0196423 A1 | 7/2021 | Shelton, IV et al. |
| 2021/0196424 A1 | 7/2021 | Shelton, IV et al. |
| 2021/0196425 A1 | 7/2021 | Shelton, IV et al. |
| 2021/0199557 A1 | 7/2021 | Shelton, IV et al. |
| 2021/0343088 A1* | 11/2021 | Payyavula ............ A61B 34/20 |
| 2021/0345952 A1 | 11/2021 | Harris et al. |
| 2021/0345953 A1 | 11/2021 | Shelton, IV et al. |
| 2021/0346015 A1 | 11/2021 | Krulevitch et al. |
| 2021/0350895 A1 | 11/2021 | Bakos et al. |
| 2021/0350896 A1 | 11/2021 | Shelton, IV et al. |
| 2021/0350897 A1 | 11/2021 | Shelton, IV et al. |
| 2021/0393338 A1 | 12/2021 | Graetzel et al. |
| 2022/0175269 A1* | 6/2022 | Lu ..................... A61B 5/6851 |
| 2023/0110791 A1 | 4/2023 | Shelton, IV et al. |

FOREIGN PATENT DOCUMENTS

| | | |
|---|---|---|
| EP | 3275386 A1 | 1/2018 |
| WO | 2007081800 A2 | 7/2007 |
| WO | 2014151621 A1 | 9/2014 |
| WO | 2020018566 A1 | 1/2020 |

OTHER PUBLICATIONS

Invitation to Pay Additional Fees for International Application No. PCT/IB2022/059079 mailed on Jan. 12, 2023, 12 pages.

Invitation to Pay Additional Fees for International Application No. PCT/IB2022/059080 mailed on Dec. 9, 2022, 16 pages.

Kurata et al. (2013) "Time-of-flight Near-infrared Spectroscopy for Nondestructive Measurement of Internal Quality in Grapefruit", Journal of the American Society for Horticultural Science, 138(3):225-228.

Lee et al. (Nov. 11-15, 2007) "Design of a Magnetic Field-Based Multi Degree-of-Freedom Orientation Sensor Using the Distributed-Multiple-Pole Model", IMECE2007-42106-Proceedings of IMECE2007, 2007 ASME International Mechanical Engineering Congress and Exposition, Seattle, Washington, USA, 6 pages.

U.S. Appl. No. 17/449,765, filed Oct. 1, 2021, Cooperative Access Hybrid Procedures.

U.S. Appl. No. 17/449,767, filed Oct. 1, 2021, Surgical Anchoring Systems for Endoluminal Access.

U.S. Appl. No. 17/449,770, filed Oct. 1, 2021, Instrument Control Imaging Systems for Visualization of Upcoming Surgical Procedure Steps.

U.S. Appl. No. 17/449,771, filed Oct. 1, 2021, Coordinated Instrument Control Systems.

U.S. Appl. No. 17/449,772, filed Oct. 1, 2021, Surgical Systems and Methods for Selectively Pressurizing a Natural Body Lumen.

U.S. Appl. No. 17/491,383, filed Sep. 30, 2021, Surgical Systems With Port Devices for Instrument Control.

U.S. Appl. No. 17/491,437, filed Sep. 30, 2021, Surgical Sealing Systems for Instrument Stabilization.

U.S. Appl. No. 17/493,526, filed Oct. 4, 2021, Surgical Systems With Devices for Both Intraluminal and Extraluminal Access.

U.S. Appl. No. 17/493,535, filed Oct. 4, 2021, Surgical Systems With Intraluminal and Extraluminal Cooperative Instruments.

U.S. Appl. No. 17/493,545, filed Oct. 4, 2021, Surgical Systems for Independently Insufflating Two Separate Anatomic Spaces.

U.S. Appl. No. 17/491,375, filed Sep. 30, 2021, Surgical Sealing Devices for a Natural Body Orifice.

International Search Report and Written Opinion for Patent Application No. PCT/IB2022/059079 dated Mar. 13, 2023, 17 pages.

International Search Report and Written Opinion for Patent Application No. PCT/IB2022/059082 dated Mar. 14, 2023, 24 pages.

* cited by examiner

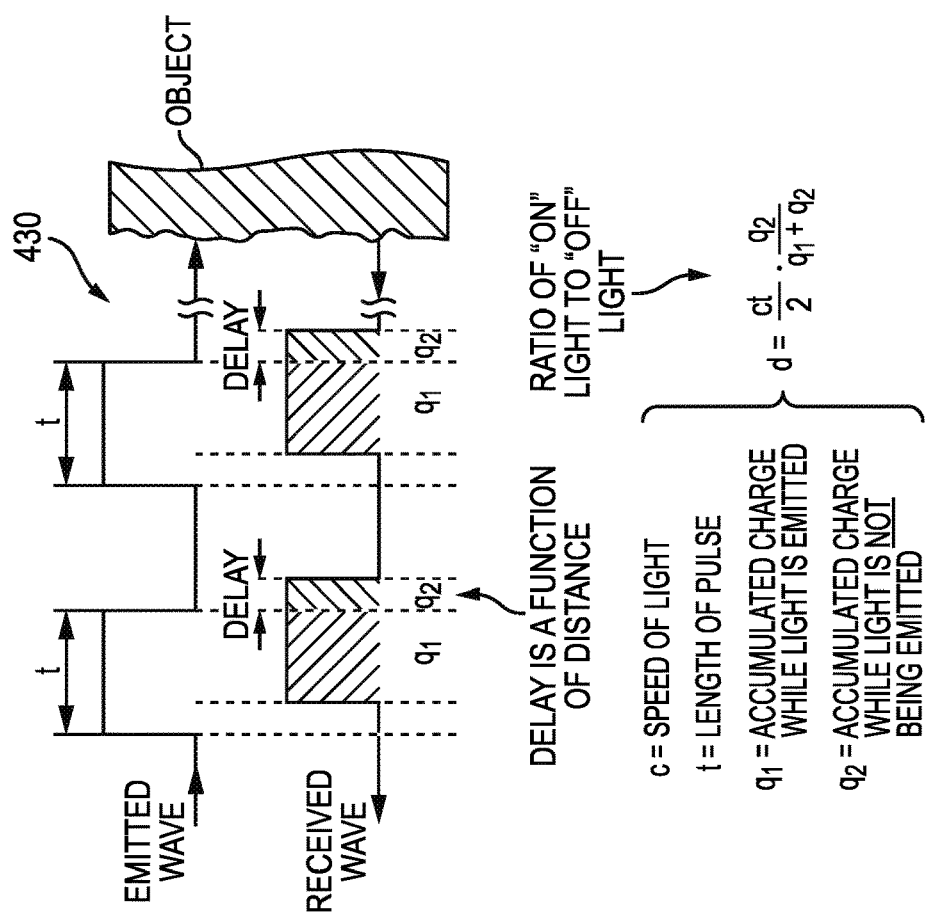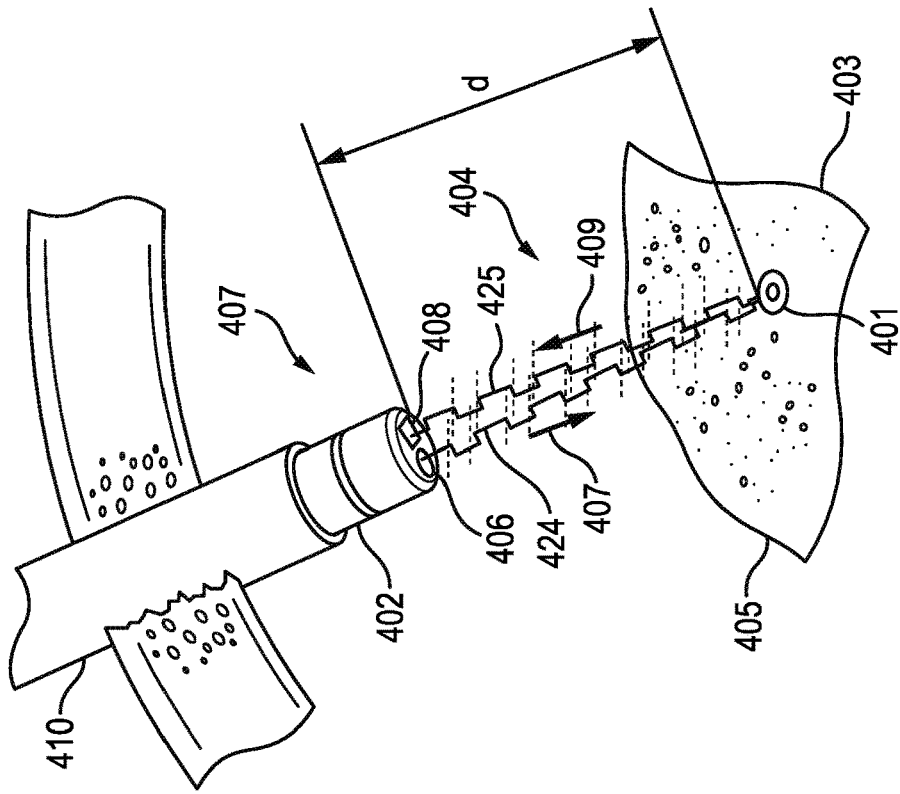

INSTRUMENT CONTROL SURGICAL IMAGING SYSTEMS

CROSS-REFERENCE TO RELATED APPLICATIONS

This application claims priority to U.S. Provisional Patent Application No. 63/249,980 filed on Sep. 29, 2021, and entitled "Cooperative Access," the disclosure of which is incorporated herein by reference in its entirety.

FIELD

The present invention relates generally to surgical systems and methods of using the same for anchoring, cooperative endoscopic and laparoscopic access and tissue manipulation, etc.

BACKGROUND

Surgical systems often incorporate an imaging system, which can allow medical practitioners to view a surgical site and/or one or more portions thereof on one or more displays, (e.g., a monitor, a computer tablet screen, etc.). The display(s) can be local and/or remote to a surgical theater. The imaging system can include a scope with a camera that views the surgical site and transmits the view to the one or more displays viewable by medical practitioner(s).

Imaging systems can be limited by the information that they are able to recognize and/or convey to the medical practitioner(s). For example, certain concealed structures, physical contours, and/or dimensions within a three-dimensional space may be unrecognizable intraoperatively by certain imaging systems. For another example, certain imaging systems may be incapable of communicating and/or conveying certain information to the medical practitioner(s) intraoperatively.

Accordingly, there remains a need for improved surgical imaging.

SUMMARY

Surgical systems for endoscopic and laparoscopic surgical procedures are provided. In one exemplary embodiment, a surgical system includes a first scope device, a second scope device, a tracking device, and a controller. The first scope device is configured to be at least partially disposed within at least one of a natural body lumen and an organ and configured to transmit image data of a first scene within a field of view of the first scope device. The second scope device is configured to be at least partially disposed outside of the at least one of the natural body lumen and the organ and to transmit image data of a second scene within a field of view of the second scope device, the second scene being different than the first scene. The tracking device is associated with one of the first scope device or the second scope device and configured to transmit a signal indicative of a location of the one of the first scope device or the second scope device relative to the other one of the first scope device or the second scope device. The controller is configured to receive (i) the transmitted image data of the first and second scenes and (ii) the transmitted signal, to determine, based on the transmitted signal, a relative distance between the first scope device and the second scope device, and to provide, based on the transmitted image data and relative distance between the first and second scopes, a merged image of at least a portion of at least the first scope device and the second scope device in a single scene. At least one of the first scope device and the second scope device in the merged image is a representative depiction thereof.

The first and second scope devices can have a variety of configurations. In some embodiments, the first scope device and the second scope device can each be illustrated as a representative depiction thereof in the merged image. In certain embodiments, the first scope device can be an endoscope and the second scope device can be a laparoscope.

In some embodiments, the first scene cannot include the second scope device, and the second scene cannot include the first scope device.

In some embodiments, the surgical system can include a first display that can be configured to display the first scene and a second display that can be configured to display the second scene. In such embodiments, at least one of the first display and the second display can be further configured to display the single scene. In such embodiments, the surgical system can include a third display that can be configured to display the single scene.

The tracking device can have a variety of configurations. In some embodiments, the tracking device can be associated with the first scope device. In other embodiments, the tracking device can be associated with the second scope device.

In some embodiments, the signal can be further indicative of an orientation of the first scope device within one of the natural body lumen and the organ relative to the second scope device, and the controller can be further configured to determine, based on the transmitted signal, a relative orientation of the first scope device. In certain embodiments, the signal can be further indicative of an orientation of the second scope device positioned outside of the at least one of the natural body lumen and the organ relative to the first scope device, and the controller can be further configured to determine, based on the transmitted signal, a relative orientation of the second scope device.

The controller can have a variety of configurations. In some embodiments, the controller can be further configured to determine, based on at least the transmitted image data, at least one of a location and an orientation of at least one instrument positioned outside of the at least one natural body lumen and the organ relative to the first scope device, in which at least a portion of the at least one instrument can be illustrated as an actual depiction or representative depiction thereof in the merged image. In certain embodiments, the controller can be further configured to (i) receive an additional signal that is indicative of at least one of a location and an orientation of at least one instrument positioned outside of the at least one natural body lumen and the organ relative to the second scope device, (ii) to determine, based on the transmitted additional signal, at least one of a relative location and a relative orientation of the at least one instrument, in which at least a portion of the at least one instrument can be illustrated as an actual depiction or representative depiction thereof in the merged image.

Methods of operating a surgical system are also provided. In one exemplary embodiment, a method includes transmitting, by a first scope device, image data of a first scene within a field of view of the first scope device while at least a portion of the first device is positioned within at least one of a natural body lumen and an organ, transmitting, by a second scope device, image data of a second scene within a field of view of the second scope device while the second scope device is positioned outside of the at least one of the natural body lumen and the organ, the second scene being different than the first scene, and transmitting, by a tracking device, a signal indicative of a location of one of the positioned first scope device or second scope device relative to the other positioned first scope device or second scope device. The method further includes receiving, by a controller, the transmitted image data of the first and second scenes and the transmitted signals of the location of the first and second scope devices, and determining, by the controller and based on the transmitted signal, a relative distance between the first scope device and the second scope device. The method further includes generating, by the controller and based on the transmitted image data and the relative distance between the first and second scope devices, a merged image of at least a portion of at least the first scope device and the second scope device in a single scene, in which at least one of the first scope device and the second scope device in the single scene is a representative depiction thereof.

In some embodiments, the method can include illustrating a representative depiction of the first scope device in the merged image, and illustrating a representative depiction of the second scope device in the merged image.

In some embodiments, the method can include displaying the first scene on a first display, and displaying the second scene on a second display.

In some embodiments, the method can include displaying the single scene on at least one of the first display and the second display.

In some embodiments, the method can include transmitting, by the tracking device, a signal indicative of an orientation of the one of the first scope device or the second scope device relative to the other one of the first scope device or the second scope device.

In some embodiments, the method can include determining, by the controller and based on the transmitted image data, at least one of a position and an orientation of at least one or more instruments positioned outside of the at least one natural body lumen and the organ relative to the first scope device.

BRIEF DESCRIPTION OF DRAWINGS

The present invention is described by way of reference to the accompanying figures which are as follows:

FIG. 15 is a schematic view of one embodiment of a near infrared (NIR) time-of-flight measurement system being utilized intraoperatively;

FIG. 16 shows a time-of-flight timing diagram for the system of FIG. 15;

DETAILED DESCRIPTION

Figure 1:
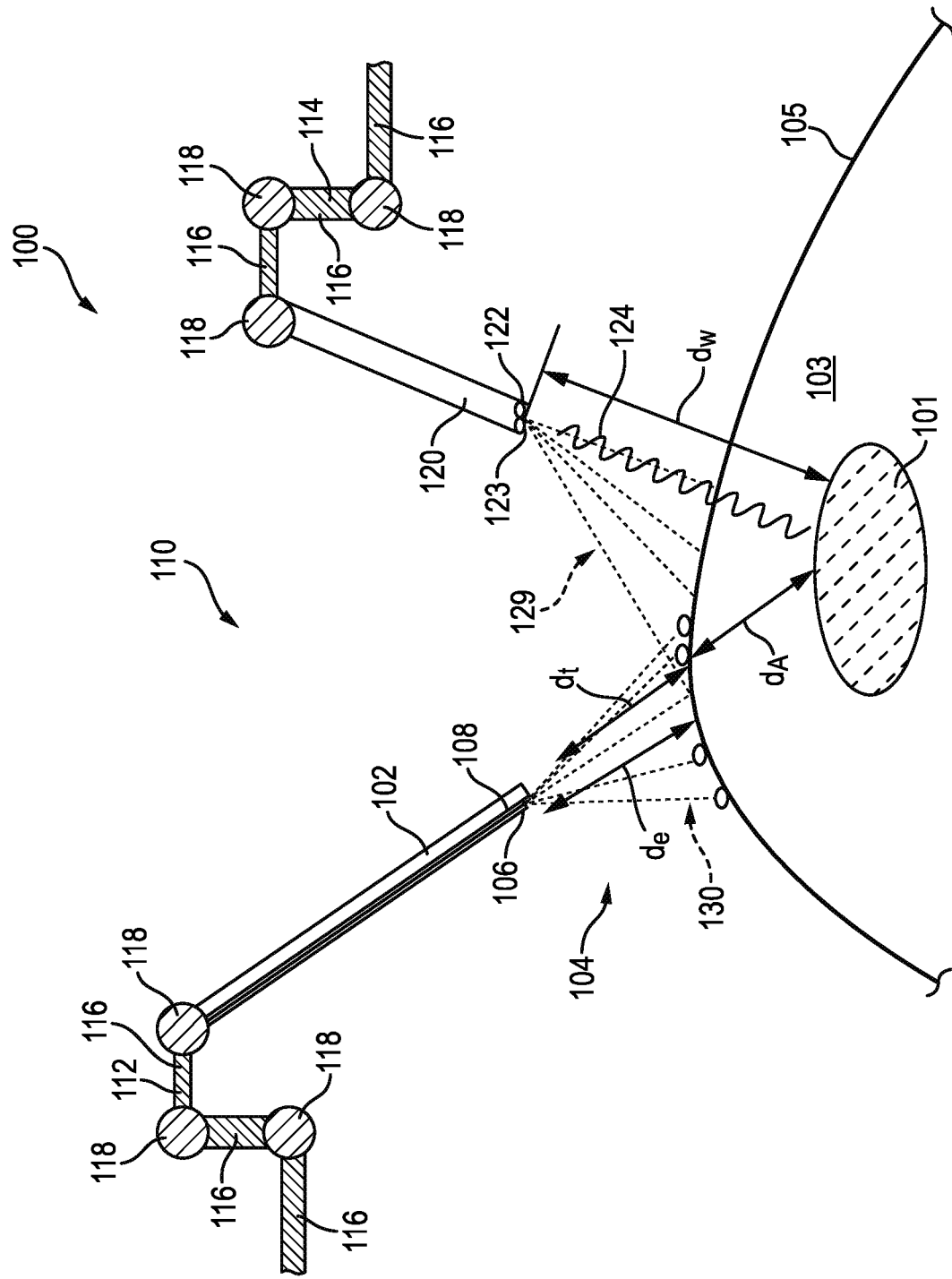
FIG. 1 is a schematic view of one embodiment of a surgical visualization system.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Surgical Visualization

In general, a surgical visualization system is configured to leverage "digital surgery" to obtain additional information about a patient's anatomy and/or a surgical procedure. The surgical visualization system is further configured to convey data to one or more medical practitioners in a helpful manner. Various aspects of the present disclosure provide improved visualization of the patient's anatomy and/or the surgical procedure, and/or use visualization to provide improved control of a surgical tool (also referred to herein as a "surgical device" or a "surgical instrument").

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization systems described herein can be used in combination with a robotic surgical system, surgical visualization systems are not limited to use with a robotic surgical system. In certain instances, surgical visualization using a surgical visualization system can occur without robotics and/or with limited and/or optional robotic assistance. Similarly, digital surgery can occur without robotics and/or with limited and/or optional robotic assistance.

In certain instances, a surgical system that incorporates a surgical visualization system may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, a surgical fastener, a clip, a tack, a bougie, a band, a plate, and other foreign structures. Critical structures can be determined on a patient-by-patient and/or a procedure-by-procedure basis. Smart dissection technology may provide, for example, improved intraoperative guidance for dissection and/or may enable smarter decisions with critical anatomy detection and avoidance technology.

A surgical system incorporating a surgical visualization system may enable smart anastomosis technologies that provide more consistent anastomoses at optimal location(s) with improved workflow. Cancer localization technologies may be improved with a surgical visualization platform. For example, cancer localization technologies can identify and track a cancer location, orientation, and its margins. In certain instances, the cancer localization technologies may compensate for movement of a surgical instrument, a patient, and/or the patient's anatomy during a surgical procedure in order to provide guidance back to the point of interest for medical practitioner(s).

A surgical visualization system may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies may be utilized without ionizing radiation and/or contrast agents. With respect to lymph node diagnostics and mapping, a surgical visualization platform may, for example, preoperatively locate, map, and ideally diagnose the lymph system and/or lymph nodes involved in cancerous diagnosis and staging.

During a surgical procedure, information available to a medical practitioner via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move pre-operatively (e.g., before a surgical procedure but after a preoperative scan) and/or intraoperatively. In such instances, the medical practitioner can be unable to accurately determine the location of a critical structure intraoperatively.

When the position of a critical structure is uncertain and/or when the proximity between the critical structure and a surgical tool is unknown, a medical practitioner's decision-making process can be inhibited. For example, a medical practitioner may avoid certain areas in order to avoid inadvertent dissection of a critical structure; however, the avoided area may be unnecessarily large and/or at least partially misplaced. Due to uncertainty and/or overly/excessive exercises in caution, the medical practitioner may not access certain desired regions. For example, excess caution may cause a medical practitioner to leave a portion of a tumor and/or other undesirable tissue in an effort to avoid a critical structure even if the critical structure is not in the particular area and/or would not be negatively impacted by the medical practitioner working in that particular area. In certain instances, surgical results can be improved with increased knowledge and/or certainty, which can allow a surgeon to be more accurate and, in certain instances, less conservative/more aggressive with respect to particular anatomical areas.

A surgical visualization system can allow for intraoperative identification and avoidance of critical structures. The surgical visualization system may thus enable enhanced intraoperative decision making and improved surgical outcomes. The surgical visualization system can provide advanced visualization capabilities beyond what a medical practitioner sees with the "naked eye" and/or beyond what an imaging system can recognize and/or convey to the medical practitioner. The surgical visualization system can augment and enhance what a medical practitioner is able to know prior to tissue treatment (e.g., dissection, etc.) and, thus, may improve outcomes in various instances. As a result, the medical practitioner can confidently maintain momentum throughout the surgical procedure knowing that the surgical visualization system is tracking a critical structure, which may be approached during dissection, for example. The surgical visualization system can provide an indication to the medical practitioner in sufficient time for the medical practitioner to pause and/or slow down the surgical procedure and evaluate the proximity to the critical structure to prevent inadvertent damage thereto. The surgical visualization system can provide an ideal, optimized, and/or customizable amount of information to the medical practitioner to allow the medical practitioner to move confidently and/or quickly through tissue while avoiding inadvertent damage to healthy tissue and/or critical structure(s) and, thus, to minimize the risk of harm resulting from the surgical procedure.

Surgical visualization systems are described in detail below. In general, a surgical visualization system can include a first light emitter configured to emit a plurality of spectral waves, a second light emitter configured to emit a light pattern, and a receiver, or sensor, configured to detect visible light, molecular responses to the spectral waves (spectral imaging), and/or the light pattern. The surgical visualization system can also include an imaging system and a control circuit in signal communication with the receiver and the imaging system. Based on output from the receiver, the control circuit can determine a geometric surface map, e.g., three-dimensional surface topography, of the visible surfaces at the surgical site and a distance with respect to the surgical site, such as a distance to an at least partially concealed structure. The imaging system can convey the geometric surface map and the distance to a medical practitioner. In such instances, an augmented view of the surgical site provided to the medical practitioner can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of a surgical tool to the visible and obstructing tissue and/or to the at least partially concealed structure and/or a depth of the concealed structure below the visible surface of the obstructing tissue. For example, the visualization system can determine a distance with respect to the augmented line on the surface of the visible tissue and convey the distance to the imaging system.

Throughout the present disclosure, any reference to "light," unless specifically in reference to visible light, can include electromagnetic radiation (EMR) or photons in the visible and/or non-visible portions of the EMR wavelength spectrum. The visible spectrum, sometimes referred to as the optical spectrum or luminous spectrum, is that portion of the electromagnetic spectrum that is visible to (e.g., can be detected by) the human eye and may be referred to as "visible light" or simply "light." A typical human eye will respond to wavelengths in air that are from about 380 nm to about 750 nm. The invisible spectrum (e.g., the non-luminous spectrum) is that portion of the electromagnetic spectrum that lies below and above the visible spectrum. The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

FIG. 1 illustrates one embodiment of a surgical visualization system 100. The surgical visualization system 100 is configured to create a visual representation of a critical structure 101 within an anatomical field. The critical structure 101 can include a single critical structure or a plurality of critical structures. As discussed herein, the critical structure 101 can be any of a variety of structures, such as an anatomical structure, e.g., a ureter, an artery such as a superior mesenteric artery, a vein such as a portal vein, a nerve such as a phrenic nerve, a vessel, a tumor, or other anatomical structure, or a foreign structure, e.g., a surgical device, a surgical fastener, a surgical clip, a surgical tack, a bougie, a surgical band, a surgical plate, or other foreign structure. As discussed herein, the critical structure 101 can be identified on a patient-by-patient and/or a procedure-by-procedure basis. Embodiments of critical structures and of identifying critical structures using a visualization system are further described in U.S. Pat. No. 10,792,034 entitled "Visualization Of Surgical Devices" issued Oct. 6, 2020, which is hereby incorporated by reference in its entirety.

In some instances, the critical structure 101 can be embedded in tissue 103. The tissue 103 can be any of a variety of tissues, such as fat, connective tissue, adhesions, and/or organs. Stated differently, the critical structure 101 may be positioned below a surface 105 of the tissue 103. In such instances, the tissue 103 conceals the critical structure 101 from the medical practitioner's "naked eye" view. The tissue 103 also obscures the critical structure 101 from the view of an imaging device 120 of the surgical visualization system 100. Instead of being fully obscured, the critical structure 101 can be partially obscured from the view of the medical practitioner and/or the imaging device 120.

The surgical visualization system 100 can be used for clinical analysis and/or medical intervention. In certain instances, the surgical visualization system 100 can be used intraoperatively to provide real-time information to the medical practitioner during a surgical procedure, such as real-time information regarding proximity data, dimensions, and/or distances. A person skilled in the art will appreciate that information may not be precisely real time but nevertheless be considered to be real time for any of a variety of reasons, such as time delay induced by data transmission, time delay induced by data processing, and/or sensitivity of measurement equipment. The surgical visualization system 100 is configured for intraoperative identification of critical structure(s) and/or to facilitate the avoidance of the critical structure(s) 101 by a surgical device. For example, by identifying the critical structure 101, a medical practitioner can avoid maneuvering a surgical device around the critical structure 101 and/or a region in a predefined proximity of the critical structure 101 during a surgical procedure. For another example, by identifying the critical structure 101, a medical practitioner can avoid dissection of and/or near the critical structure 101, thereby helping to prevent damage to the critical structure 101 and/or helping to prevent a surgical device being used by the medical practitioner from being damaged by the critical structure 101.

The surgical visualization system 100 is configured to incorporate tissue identification and geometric surface mapping in combination with the surgical visualization system's distance sensor system 104. In combination, these features of the surgical visualization system 100 can determine a position of a critical structure 101 within the anatomical field and/or the proximity of a surgical device 102 to the surface 105 of visible tissue 103 and/or to the critical structure 101. Moreover, the surgical visualization system 100 includes an imaging system that includes the imaging device 120 configured to provide real-time views of the surgical site. The imaging device 120 can include, for example, a spectral camera (e.g., a hyperspectral camera, multispectral camera, or selective spectral camera), which is configured to detect reflected spectral waveforms and generate a spectral cube of images based on the molecular response to the different wavelengths. Views from the imaging device 120 can be provided in real time to a medical practitioner, such as on a display (e.g., a monitor, a computer tablet screen, etc.). The displayed views can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intra-operatively provide advanced data synthesis and integrated information to the medical practitioner.

The imaging device 120 can be configured to detect visible light, spectral light waves (visible or invisible), and a structured light pattern (visible or invisible). Examples of the imaging device 120 includes scopes, e.g., an endoscope, an arthroscope, an angioscope, a bronchoscope, a choledochoscope, a colonoscope, a cytoscope, a duodenoscope, an enteroscope, an esophagogastro-duodenoscope (gastroscope), a laryngoscope, a nasopharyngo-neproscope, a sigmoidoscope, a thoracoscope, an ureteroscope, or an exoscope. Scopes can be particularly useful in minimally invasive surgical procedures. In open surgery applications, the imaging device 120 may not include a scope.

The tissue identification subsystem can be achieved with a spectral imaging system. The spectral imaging system can rely on imaging such as hyperspectral imaging, multispectral imaging, or selective spectral imaging. Embodiments of hyperspectral imaging of tissue are further described in U.S. Pat. No. 9,274,047 entitled "System And Method For Gross Anatomic Pathology Using Hyperspectral Imaging" issued Mar. 1, 2016, which is hereby incorporated by reference in its entirety.

The surface mapping subsystem can be achieved with a light pattern system. Various surface mapping techniques using a light pattern (or structured light) for surface mapping can be utilized in the surgical visualization systems described herein. Structured light is the process of projecting a known pattern (often a grid or horizontal bars) on to a surface. In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Embodiments of surface mapping and a surgical system including a light source and a projector for projecting a light pattern are further described in U.S. Pat. Pub. No. 2017/0055819 entitled "Set Comprising A Surgical Instrument" published Mar. 2, 2017, U.S. Pat. Pub. No. 2017/0251900 entitled "Depiction System" published Sep. 7, 2017, and U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, which are hereby incorporated by reference in their entireties.

The distance determining system can be incorporated into the surface mapping system. For example, structured light can be utilized to generate a three-dimensional (3D) virtual model of the visible surface 105 and determine various distances with respect to the visible surface 105. Additionally or alternatively, the distance determining system can rely on time-of-flight measurements to determine one or more distances to the identified tissue (or other structures) at the surgical site.

The surgical visualization system 100 also includes a surgical device 102. The surgical device 102 can be any suitable surgical device. Examples of the surgical device 102 includes a surgical dissector, a surgical stapler, a surgical grasper, a clip applier, a smoke evacuator, a surgical energy device (e.g., mono-polar probes, bi-polar probes, ablation probes, an ultrasound device, an ultrasonic end effector, etc.), etc. In some embodiments, the surgical device 102 includes an end effector having opposing jaws that extend from a distal end of a shaft of the surgical device 102 and that are configured to engage tissue therebetween.

The surgical visualization system 100 can be configured to identify the critical structure 101 and a proximity of the surgical device 102 to the critical structure 101. The imaging device 120 of the surgical visualization system 100 is configured to detect light at various wavelengths, such as visible light, spectral light waves (visible or invisible), and a structured light pattern (visible or invisible). The imaging device 120 can include a plurality of lenses, sensors, and/or receivers for detecting the different signals. For example, the imaging device 120 can be a hyperspectral, multispectral, or selective spectral camera, as described herein. The imaging device 120 can include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional (3D) image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, a field of view of the imaging device 120 can overlap with a pattern of light (structured light) on the surface 105 of the tissue 103, as shown in FIG. 1.

As in this illustrated embodiment, the surgical visualization system 100 can be incorporated into a robotic surgical system 110. The robotic surgical system 110 can have a variety of configurations, as discussed herein. In this illustrated embodiment, the robotic surgical system 110 includes a first robotic arm 112 and a second robotic arm 114. The robotic arms 112, 114 each include rigid structural members 116 and joints 118, which can include servomotor controls. The first robotic arm 112 is configured to maneuver the surgical device 102, and the second robotic arm 114 is configured to maneuver the imaging device 120. A robotic control unit of the robotic surgical system 110 is configured to issue control motions to the first and second robotic arms 112, 114, which can affect the surgical device 102 and the imaging device 120, respectively.

In some embodiments, one or more of the robotic arms 112, 114 can be separate from the main robotic system 110 used in the surgical procedure. For example, at least one of the robotic arms 112, 114 can be positioned and registered to a particular coordinate system without a servomotor control. For example, a closed-loop control system and/or a plurality of sensors for the robotic arms 112, 114 can control and/or register the position of the robotic arm(s) 112, 114 relative to the particular coordinate system. Similarly, the position of the surgical device 102 and the imaging device 120 can be registered relative to a particular coordinate system.

Examples of robotic surgical systems include the Ottava™ robotic-assisted surgery system (Johnson & Johnson of New Brunswick, NJ), da Vinci® surgical systems (Intuitive Surgical, Inc. of Sunnyvale, CA), the Hugo™ robotic-assisted surgery system (Medtronic PLC of Minneapolis, MN), the Versius® surgical robotic system (CMR Surgical Ltd of Cambridge, UK), and the Monarch® platform (Auris Health, Inc. of Redwood City, CA). Embodiments of various robotic surgical systems and using robotic surgical systems are further described in U.S. Pat. Pub. No. 2018/0177556 entitled "Flexible Instrument Insertion Using An Adaptive Force Threshold" filed Dec. 28, 2016, U.S. Pat. Pub. No. 2020/0000530 entitled "Systems And Techniques For Providing Multiple Perspectives During Medical Procedures" filed Apr. 16, 2019, U.S. Pat. Pub. No. 2020/0170720 entitled "Image-Based Branch Detection And Mapping For Navigation" filed Feb. 7, 2020, U.S. Pat. Pub. No. 2020/0188043 entitled "Surgical Robotics System" filed Dec. 9, 2019, U.S. Pat. Pub. No. 2020/0085516 entitled "Systems And Methods For Concomitant Medical Procedures" filed Sep. 3, 2019, U.S. Pat. No. 8,831,782 entitled "Patient-Side Surgeon Interface For A Teleoperated Surgical Instrument" filed Jul. 15, 2013, and Intl. Pat. Pub. No. WO 2014151621 entitled "Hyperdexterous Surgical System" filed Mar. 13, 2014, which are hereby incorporated by reference in their entireties.

The surgical visualization system 100 also includes an emitter 106. The emitter 106 is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120. In one aspect, the projected light array 130 is employed by the surgical visualization system 100 to determine the shape defined by the surface 105 of the tissue 103 and/or motion of the surface 105 intraoperatively. The imaging device 120 is configured to detect the projected light arrays 130 reflected from the surface 105 to determine the topography of the surface 105 and various distances with respect to the surface 105.

As in this illustrated embodiment, the imaging device 120 can include an optical waveform emitter 123, such as by being mounted on or otherwise attached on the imaging device 120. The optical waveform emitter 123 is configured to emit electromagnetic radiation 124 (near-infrared (NIR) photons) that can penetrate the surface 105 of the tissue 103 and reach the critical structure 101. The imaging device 120 and the optical waveform emitter 123 can be positionable by the robotic arm 114. The optical waveform emitter 123 is mounted on or otherwise on the imaging device 122 but in other embodiments can be positioned on a separate surgical device from the imaging device 120. A corresponding waveform sensor 122 (e.g., an image sensor, spectrometer, or vibrational sensor) of the imaging device 120 is configured to detect the effect of the electromagnetic radiation received by the waveform sensor 122. The wavelengths of the electromagnetic radiation 124 emitted by the optical waveform emitter 123 are configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 can be variable. The waveform sensor 122 and optical waveform emitter 123 can be inclusive of a multispectral imaging system and/or a selective spectral imaging system, for example. In other instances, the waveform sensor 122 and optical waveform emitter 123 can be inclusive of a photoacoustic imaging system, for example.

The distance sensor system 104 of the surgical visualization system 100 is configured to determine one or more distances at the surgical site. The distance sensor system 104 can be a time-of-flight distance sensor system that includes an emitter, such as the emitter 106 as in this illustrated embodiment, and that includes a receiver 108. In other instances, the time-of-flight emitter can be separate from the structured light emitter. The emitter 106 can include a very tiny laser source, and the receiver 108 can include a matching sensor. The distance sensor system 104 is configured to detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104.

The receiver 108 of the distance sensor system 104 is positioned on the surgical device 102 in this illustrated embodiment, but in other embodiments the receiver 108 can be mounted on a separate surgical device instead of the surgical device 102. For example, the receiver 108 can be mounted on a cannula or trocar through which the surgical device 102 extends to reach the surgical site. In still other embodiments, the receiver 108 for the distance sensor system 104 can be mounted on a separate robotically-controlled arm of the robotic system 110 (e.g., on the second robotic arm 114) than the first robotic arm 112 to which the surgical device 102 is coupled, can be mounted on a movable arm that is operated by another robot, or be mounted to an operating room (OR) table or fixture. In some embodiments, the imaging device 120 includes the receiver 108 to allow for determining the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the distance sensor system 104. The three-dimensional position of the receiver 108 can be known and/or registered to the robot coordinate plane intraoperatively.

As in this illustrated embodiment, the position of the emitter 106 of the distance sensor system 104 can be controlled by the first robotic arm 112, and the position of the receiver 108 of the distance sensor system 104 can be controlled by the second robotic arm 114. In other embodiments, the surgical visualization system 100 can be utilized apart from a robotic system. In such instances, the distance sensor system 104 can be independent of the robotic system.

In FIG. 1, $d_e$ is emitter-to-tissue distance from the emitter 106 to the surface 105 of the tissue 103, and $d_t$ is device-to-tissue distance from a distal end of the surgical device 102 to the surface 105 of the tissue 103. The distance sensor system 104 is configured to determine the emitter-to-tissue distance $d_e$. The device-to-tissue distance $d_t$ is obtainable from the known position of the emitter 106 on the surgical device 102, e.g., on a shaft thereof proximal to the surgical device's distal end, relative to the distal end of the surgical device 102. In other words, when the distance between the emitter 106 and the distal end of the surgical device 102 is known, the device-to-tissue distance $d_t$ can be determined from the emitter-to-tissue distance $d_e$. In some embodiments, the shaft of the surgical device 102 can include one or more articulation joints and can be articulatable with respect to the emitter 106 and jaws at the distal end of the surgical device 102. The articulation configuration can include a multi-joint vertebrae-like structure, for example. In some embodiments, a three-dimensional camera can be utilized to triangulate one or more distances to the surface 105.

In FIG. 1, $d_w$ is camera-to-critical structure distance from the optical waveform emitter 123 located on the imaging device 120 to the surface of the critical structure 101, and $d_A$ is a depth of the critical structure 101 below the surface 105 of the tissue 103 (e.g., the distance between the portion of the surface 105 closest to the surgical device 102 and the critical structure 101). The time-of-flight of the optical waveforms emitted from the optical waveform emitter 123 located on the imaging device 120 are configured to determine the camera-to-critical structure distance $d_w$.

Figure 2:
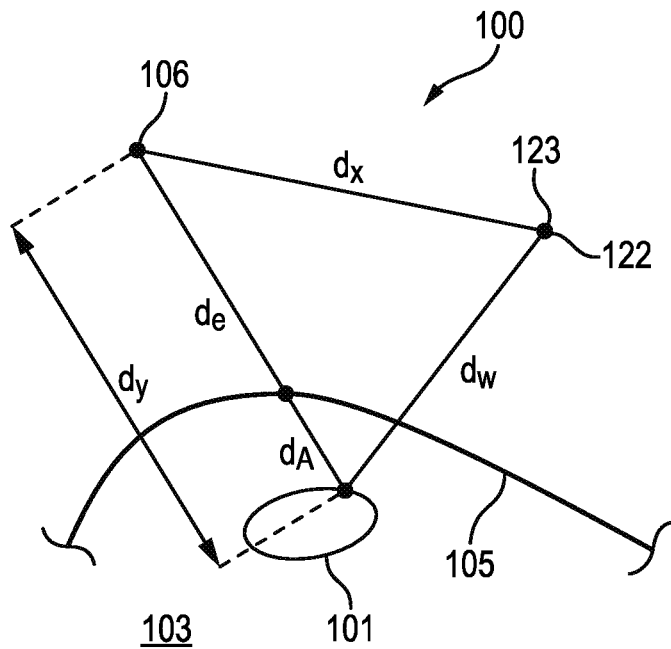
FIG. 2 is a schematic view of triangularization between a surgical device, an imaging device, and a critical structure of FIG. 1.

As shown in FIG. 2, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$. Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, the distance $d_A$ can be determined from an ultrasound, a registered magnetic resonance imaging (MRI), or computerized tomography (CT) scan. In still other instances, the distance $d_A$ can be determined with spectral imaging because the detection signal received by the imaging device 120 can vary based on the type of material, e.g., type of the tissue 103. For example, fat can decrease the detection signal in a first way, or a first amount, and collagen can decrease the detection signal in a different, second way, or a second amount.

Figure 3:
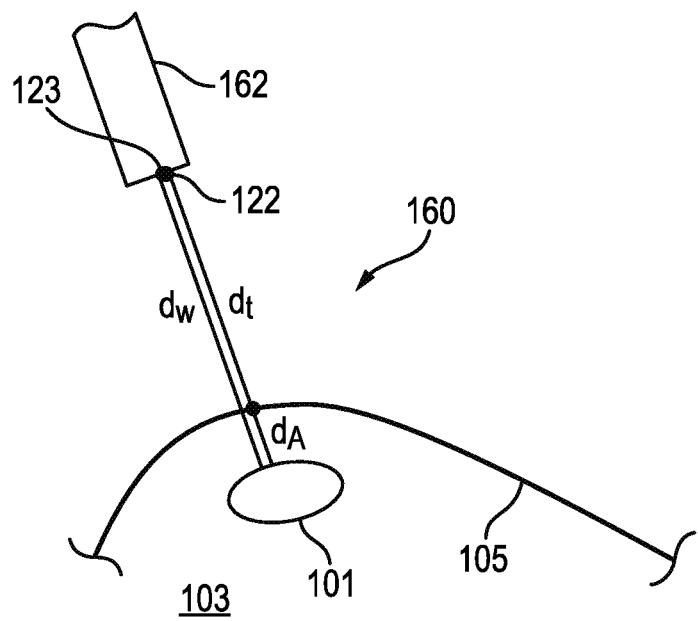
FIG. 3 is a schematic view of another embodiment of a surgical visualization system.

In another embodiment of a surgical visualization system 160 illustrated in FIG. 3, a surgical device 162, and not the imaging device 120, includes the optical waveform emitter 123 and the waveform sensor 122 that is configured to detect the reflected waveforms. The optical waveform emitter 123 is configured to emit waveforms for determining the distances $d_t$ and $d_w$ from a common device, such as the surgical device 162, as described herein. In such instances, the distance $d_A$ from the surface 105 of the tissue 103 to the surface of the critical structure 101 can be determined as follows:

$$d_A = d_w - d_t$$

Figure 4:
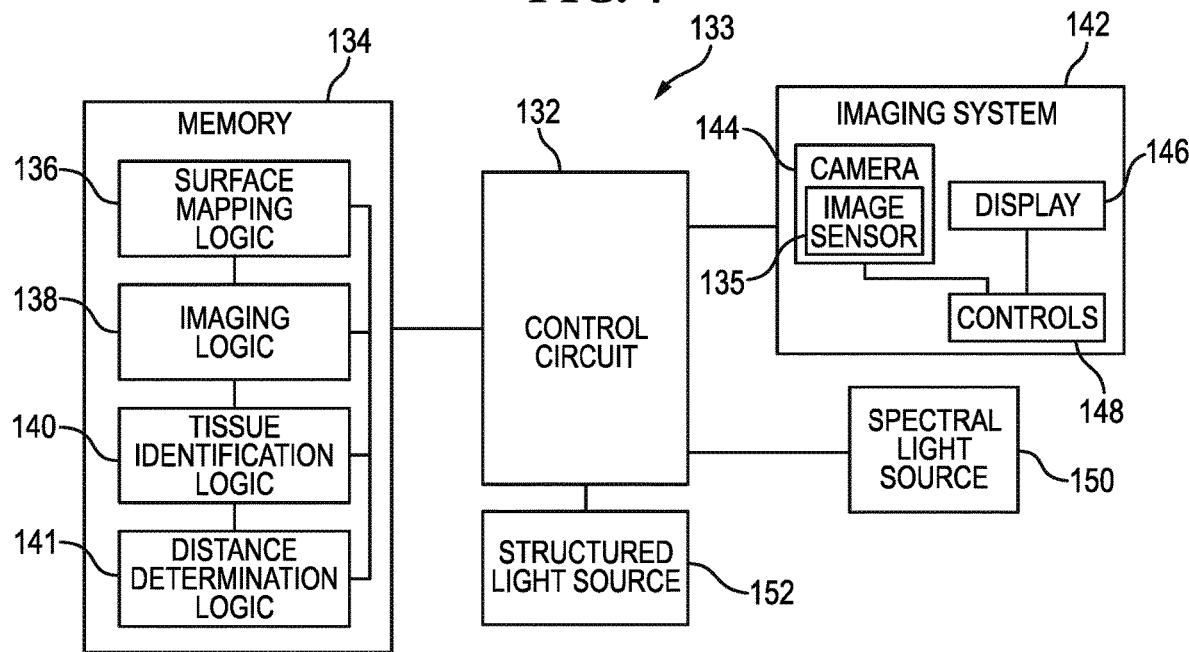
FIG. 4 is a schematic view of one embodiment of a control system for a surgical visualization system.

The surgical visualization system 100 includes a control system configured to control various aspects of the surgical visualization system 100. FIG. 4 illustrates one embodiment of a control system 133 that can be utilized as the control system of the surgical visualization system 100 (or other surgical visualization system described herein). The control system 133 includes a control circuit 132 configured to be in signal communication with a memory 134. The memory 134 is configured to store instructions executable by the control circuit 132, such as instructions to determine and/or recognize critical structures (e.g., the critical structure 101 of FIG. 1), instructions to determine and/or compute one or more distances and/or three-dimensional digital representations, and instructions to communicate information to a medical practitioner. As in this illustrated embodiment, the memory 134 can store surface mapping logic 136, imaging logic 138, tissue identification logic 140, and distance determining logic 141, although the memory 134 can store any combinations of the logics 136, 138, 140, 141 and/or can combine various logics together. The control system 133 also includes an imaging system 142 including a camera 144 (e.g., the imaging system including the imaging device 120 of FIG. 1), a display 146 (e.g., a monitor, a computer tablet screen, etc.), and controls 148 of the camera 144 and the display 146. The camera 144 includes an image sensor 135 (e.g., the waveform sensor 122) configured to receive signals from various light sources emitting light at various visible and invisible spectra (e.g., visible light, spectral imagers, three-dimensional lens, etc.). The display 146 is configured to depict real, virtual, and/or virtually-augmented images and/or information to a medical practitioner.

In an exemplary embodiment, the image sensor 135 is a solid-state electronic device containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of the image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths in a range of about 350 nm to about 1050 nm, such as in a range of about 400 nm to about 1000 nm. A person skilled in the art will appreciate that a value may not be precisely at a value but nevertheless considered to be about that value for any of a variety of reasons, such as sensitivity of measurement equipment and manufacturing tolerances. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g., Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes an emitter (e.g., the emitter 106) including a spectral light source 150 and a structured light source 152 each operably coupled to the control circuit 133. A single source can be pulsed to emit wavelengths of light in the spectral light source 150 range and wavelengths of light in the structured light source 152 range. Alternatively, a single light source can be pulsed to provide light in the invisible spectrum (e.g., infrared spectral light) and wavelengths of light on the visible spectrum. The spectral light source 150 can be, for example, a hyperspectral light source, a multispectral light source, and/or a selective spectral light source. The tissue identification logic 140 is configured to identify critical structure(s) (e.g., the critical structure 101 of FIG. 1) via data from the spectral light source 150 received by the image sensor 135 of the camera 144. The surface mapping logic 136 is configured to determine the surface contours of the visible tissue (e.g., the tissue 103) based on reflected structured light. With time-of-flight measurements, the distance determining logic 141 is configured to determine one or more distance(s) to the visible tissue and/or the critical structure. Output from each of the surface mapping logic 136, the tissue identification logic 140, and the distance determining logic 141 is configured to be provided to the imaging logic 138, and combined, blended, and/or overlaid by the imaging logic 138 to be conveyed to a medical practitioner via the display 146 of the imaging system 142.

Figure 5:
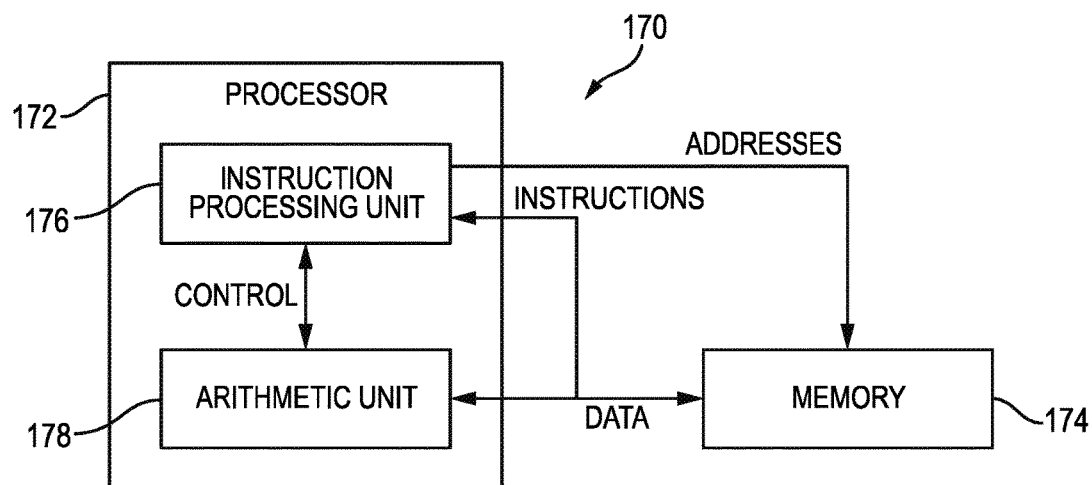
FIG. 5 is a schematic view of one embodiment of a control circuit of a control system for a surgical visualization system.

The control circuit 132 can have a variety of configurations. FIG. 5 illustrates one embodiment of a control circuit 170 that can be used as the control circuit 132 configured to control aspects of the surgical visualization system 100. The control circuit 170 is configured to implement various processes described herein. The control circuit 170 includes a microcontroller that includes a processor 172 (e.g., a microprocessor or microcontroller) operably coupled to a memory 174. The memory 174 is configured to store machine-executable instructions that, when executed by the processor 172, cause the processor 172 to execute machine instructions to implement various processes described herein. The processor 172 can be any one of a number of single-core or multicore processors known in the art. The memory 174 can include volatile and non-volatile storage media. The processor 172 includes an instruction processing unit 176 and an arithmetic unit 178. The instruction processing unit 176 is configured to receive instructions from the memory 174.

Figure 6:
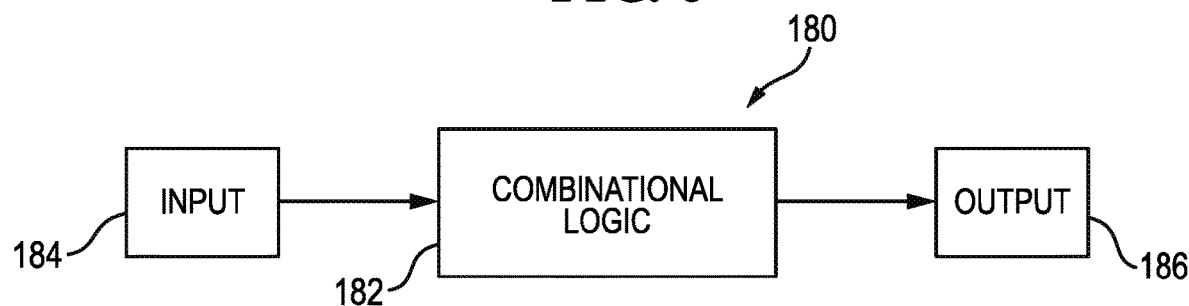
FIG. 6 is a schematic view of one embodiment of a combinational logic circuit of a surgical visualization system.

The surface mapping logic 136, the imaging logic 138, the tissue identification logic 140, and the distance determining logic 141 can have a variety of configurations. FIG. 6 illustrates one embodiment of a combinational logic circuit 180 configured to control aspects of the surgical visualization system 100 using logic such as one or more of the surface mapping logic 136, the imaging logic 138, the tissue identification logic 140, and the distance determining logic 141. The combinational logic circuit 180 includes a finite state machine that includes a combinational logic 182 configured to receive data associated with a surgical device (e.g. the surgical device 102 and/or the imaging device 120) at an input 184, process the data by the combinational logic 182, and provide an output 184 to a control circuit (e.g., the control circuit 132).

Figure 7:
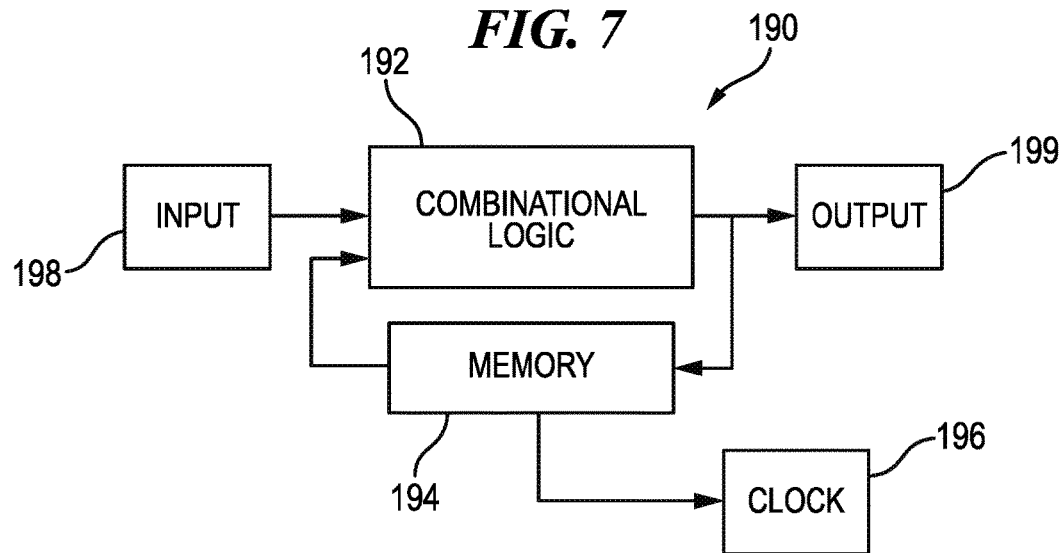
FIG. 7 is a schematic view of one embodiment of a sequential logic circuit of a surgical visualization system.

FIG. 7 illustrates one embodiment of a sequential logic circuit 190 configured to control aspects of the surgical visualization system 100 using logic such as one or more of the surface mapping logic 136, the imaging logic 138, the tissue identification logic 140, and the distance determining logic 141. The sequential logic circuit 190 includes a finite state machine that includes a combinational logic 192, a memory 194, and a clock 196. The memory 194 is configured to store a current state of the finite state machine. The sequential logic circuit 190 can be synchronous or asynchronous. The combinational logic 192 is configured to receive data associated with a surgical device (e.g. the surgical device 102 and/or the imaging device 120) at an input 426, process the data by the combinational logic 192, and provide an output 499 to a control circuit (e.g., the control circuit 132). In some embodiments, the sequential logic circuit 190 can include a combination of a processor (e.g., processor 172 of FIG. 5) and a finite state machine to implement various processes herein. In some embodiments, the finite state machine can include a combination of a combinational logic circuit (e.g., the combinational logic circuit 192 of FIG. 7) and the sequential logic circuit 190.

Figure 8:
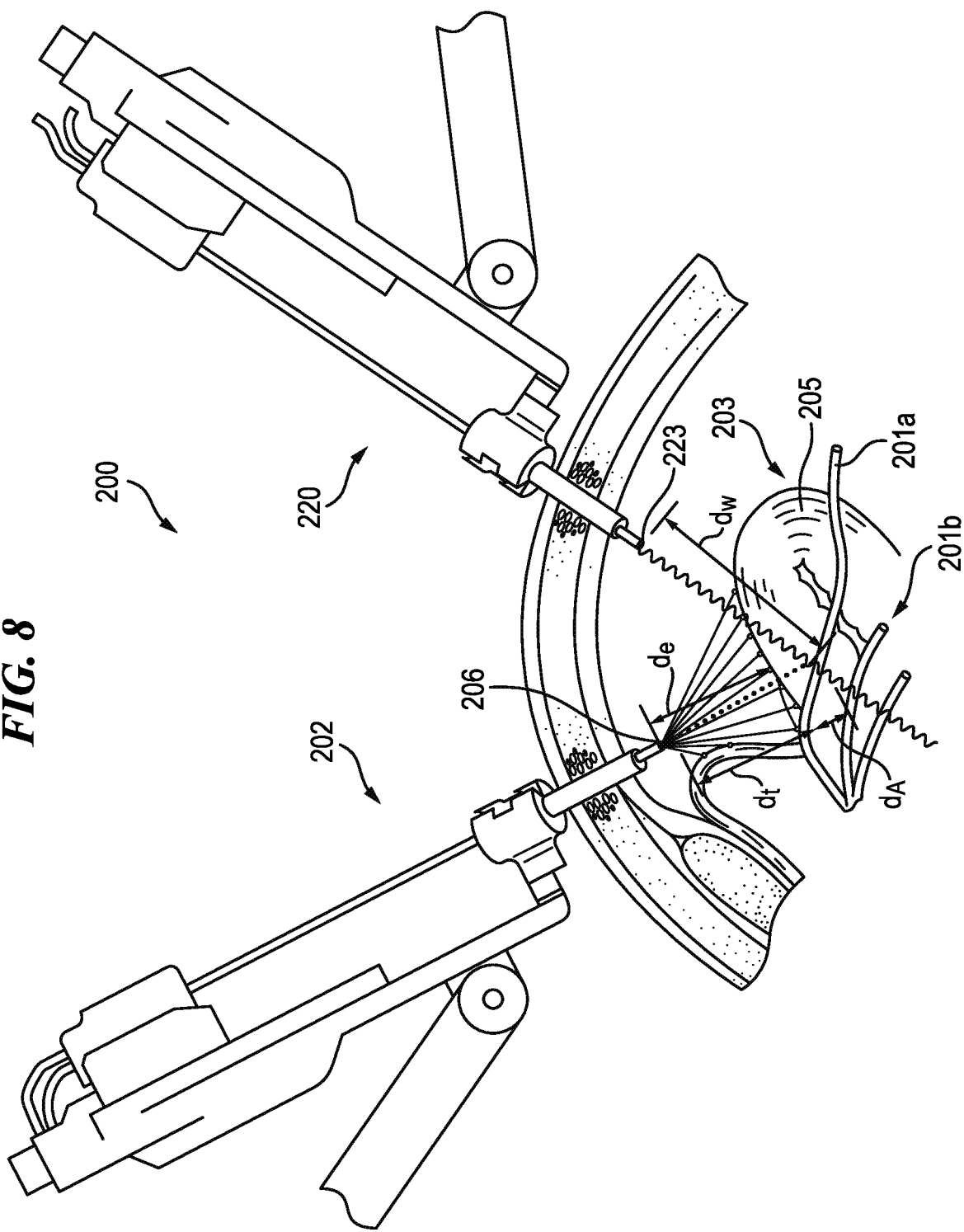
FIG. 8 is a schematic view of yet another embodiment of a surgical visualization system.

FIG. 8 illustrates another embodiment of a surgical visualization system 200. The surgical visualization system 200 is generally configured and used similar to the surgical visualization system 100 of FIG. 1, e.g., includes a surgical device 202 and an imaging device 220. The imaging device 220 includes a spectral light emitter 223 configured to emit spectral light in a plurality of wavelengths to obtain a spectral image of hidden structures, for example. The imaging device 220 can also include a three-dimensional camera and associated electronic processing circuits. The surgical visualization system 200 is shown being utilized intraoperatively to identify and facilitate avoidance of certain critical structures, such as a ureter 201a and vessels 201b, in an organ 203 (a uterus in this embodiment) that are not visible on a surface 205 of the organ 203.

The surgical visualization system 200 is configured to determine an emitter-to-tissue distance $d_e$ from an emitter 206 on the surgical device 202 to the surface 205 of the uterus 203 via structured light. The surgical visualization system 200 is configured to extrapolate a device-to-tissue distance $d_t$ from the surgical device 202 to the surface 205 of the uterus 203 based on the emitter-to-tissue distance $d_e$. The surgical visualization system 200 is also configured to determine a tissue-to-ureter distance $d_A$ from the ureter 201a to the surface 205 and a camera-to-ureter distance $d_w$ from the imaging device 220 to the ureter 201a. As described herein, e.g., with respect to the surgical visualization system 100 of FIG. 1, the surgical visualization system 200 is configured to determine the distance $d_w$ with spectral imaging and time-of-flight sensors, for example. In various embodiments, the surgical visualization system 200 can determine (e.g., triangulate) the tissue-to-ureter distance $d_A$ (or depth) based on other distances and/or the surface mapping logic described herein.

Figure 9:
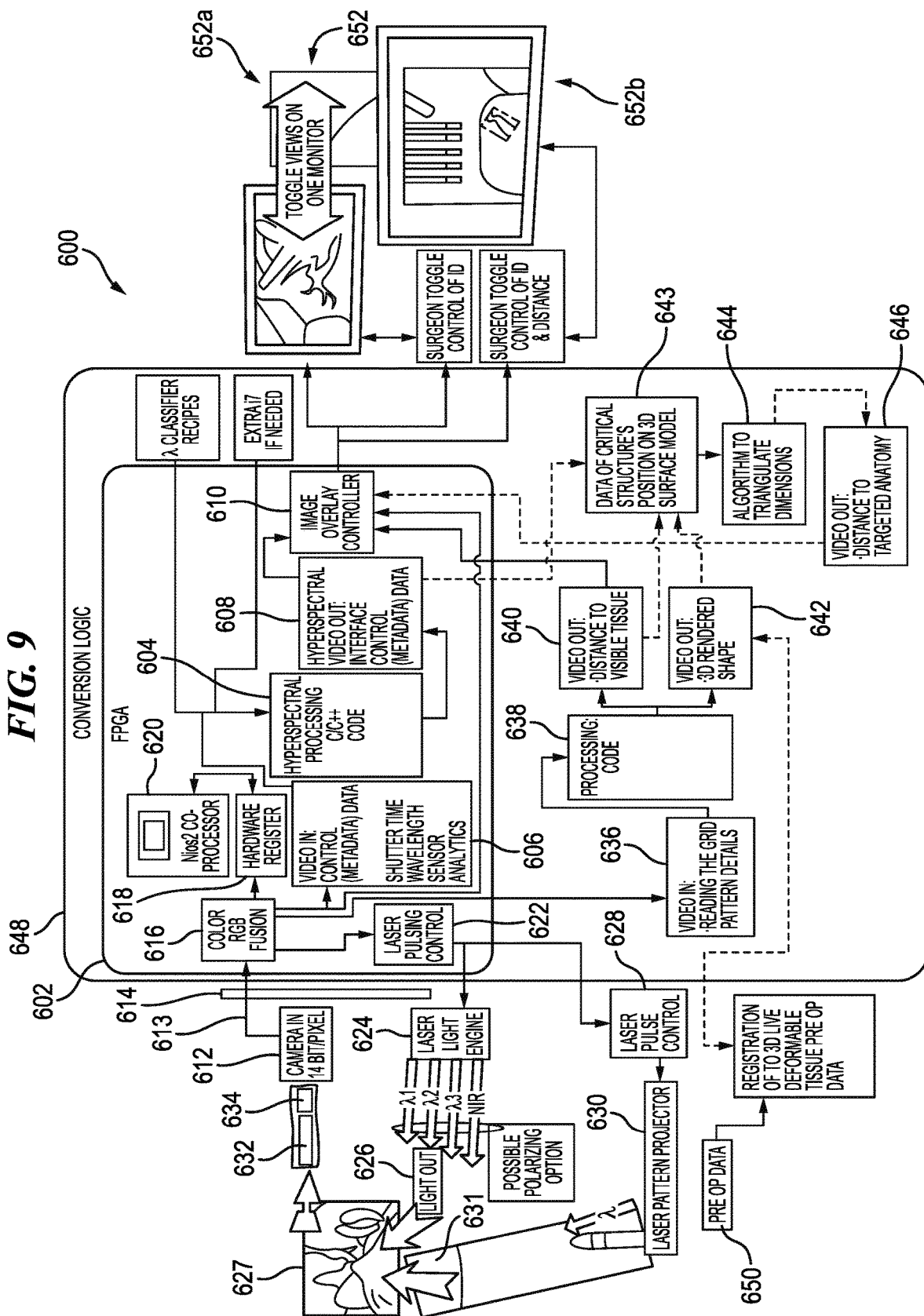
FIG. 9 is a schematic view of another embodiment of a control system for a surgical visualization system.

As mentioned above, a surgical visualization system includes a control system configured to control various aspects of the surgical visualization system. The control system can have a variety of configurations. FIG. 9 illustrates one embodiment of a control system 600 for a surgical visualization system, such as the surgical visualization system 100 of FIG. 1, the surgical visualization system 200 of FIG. 8, or other surgical visualization system described herein. The control system 600 is a conversion system that integrates spectral signature tissue identification and structured light tissue positioning to identify a critical structure, especially when those structure(s) are obscured by tissue, e.g., by fat, connective tissue, blood tissue, and/or organ(s), and/or by blood, and/or to detect tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 configured to convert tissue data to usable information for surgeons and/or other medical practitioners. For example, variable reflectance based on wavelengths with respect to obscuring material can be utilized to identify the critical structure in the anatomy. Moreover, the control system 600 is configured to combine the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various embodiments, the control system 600 is configured to provide warnings to a medical practitioner when in the proximity of one or more critical structures. Various algorithms can be employed to guide robotic automation and semi-automated approaches based on the surgical procedure and proximity to the critical structure(s).

A projected array of lights is employed by the control system 600 to determine tissue shape and motion intraoperatively. Alternatively, flash Lidar may be utilized for surface mapping of the tissue.

The control system 600 is configured to detect the critical structure, which as mentioned above can include one or more critical structures, and provide an image overlay of the critical structure and measure the distance to the surface of the visible tissue and the distance to the embedded/buried critical structure(s). The control system 600 can measure the distance to the surface of the visible tissue or detect the critical structure and provide an image overlay of the critical structure.

The control system 600 includes a spectral control circuit 602. The spectral control circuit 602 can be a field programmable gate array (FPGA) or another suitable circuit configuration, such as the configurations described with respect to FIG. 6, FIG. 7, and FIG. 8. The spectral control circuit 602 includes a processor 604 configured to receive video input signals from a video input processor 606. The processor 604 can be configured for hyperspectral processing and can utilize C/C++ code, for example. The video input processor 606 is configured to receive video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 is configured to provides the video output signal to an image overlay controller 610.

The video input processor 606 is operatively coupled to a camera 612 at the patient side via a patient isolation circuit 614. The camera 612 includes a solid state image sensor 634. The patient isolation circuit 614 can include a plurality of transformers so that the patient is isolated from other circuits in the system. The camera 612 is configured to receive intraoperative images through optics 632 and the image sensor 634. The image sensor 634 can include a CMOS image sensor, for example, or can include another image sensor technology, such as those discussed herein in connection with FIG. 4. The camera 612 is configured to output 613 images in 14 bit/pixel signals. A person skilled in the art will appreciate that higher or lower pixel resolutions can be employed. The isolated camera output signal 613 is provided to a color RGB fusion circuit 616, which in this illustrated embodiment employs a hardware register 618 and a Nios2 co-processor 620 configured to process the camera output signal 613. A color RGB fusion output signal is provided to the video input processor 606 and a laser pulsing control circuit 622.

The laser pulsing control circuit 622 is configured to control a laser light engine 624. The laser light engine 624 is configured to output light in a plurality of wavelengths ($\lambda 1, \lambda 2, \lambda 3 \ldots \lambda n$) including near infrared (NIR). The laser light engine 624 can operate in a plurality of modes. For example, the laser light engine 624 can operate in two modes. In a first mode, e.g., a normal operating mode, the laser light engine 624 is configured to output an illuminating signal. In a second mode, e.g., an identification mode, the laser light engine 624 is configured to output RGBG and NIR light. In various embodiments, the laser light engine 624 can operate in a polarizing mode.

Light output 626 from the laser light engine 624 is configured to illuminate targeted anatomy in an intraoperative surgical site 627. The laser pulsing control circuit 622 is also configured to control a laser pulse controller 628 for a laser pattern projector 630 configured to project a laser light pattern 631, such as a grid or pattern of lines and/or dots, at a predetermined wavelength ($\lambda 2$) on an operative tissue or organ at the surgical site 627. The camera 612 is configured to receive the patterned light as well as the reflected light output through the camera optics 632. The image sensor 634 is configured to convert the received light into a digital signal.

The color RGB fusion circuit 616 is also configured to output signals to the image overlay controller 610 and a video input module 636 for reading the laser light pattern 631 projected onto the targeted anatomy at the surgical site 627 by the laser pattern projector 630. A processing module 638 is configured to process the laser light pattern 631 and output a first video output signal 640 representative of the distance to the visible tissue at the surgical site 627. The data is provided to the image overlay controller 610. The processing module 638 is also configured to output a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 is configured to determine the distance (e.g., distance $d_A$ of FIG. 1) to a buried critical structure (e.g., via triangularization algorithms 644), and the distance to the buried critical structure can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650, such as from a CT or MRI scan, can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Embodiments of registration of preoperative data are further described in U.S. Pat. Pub. No. 2020/0015907 entitled "Integration Of Imaging Data" filed Sep. 11, 2018, which is hereby incorporated by reference herein in its entirety.

The video monitors 652 are configured to output the integrated/augmented views from the image overlay controller 610. A medical practitioner can select and/or toggle between different views on one or more displays. On a first display 652a, which is a monitor in this illustrated embodiment, the medical practitioner can toggle between (A) a view in which a three-dimensional rendering of the visible tissue is depicted and (B) an augmented view in which one or more hidden critical structures are depicted over the three-dimensional rendering of the visible tissue. On a second display 652b, which is a monitor in this illustrated embodiment, the medical practitioner can toggle on distance measurements to one or more hidden critical structures and/or the surface of visible tissue, for example.

The various surgical visualization systems described herein can be utilized to visualize various different types of tissues and/or anatomical structures, including tissues and/or anatomical structures that may be obscured from being visualized by EMR in the visible portion of the spectrum. The surgical visualization system can utilize a spectral imaging system, as mentioned above, which can be configured to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be configured to characterize the tissue type of the tissue being visualized based upon the particular combination of constituent materials.

Figure 10:
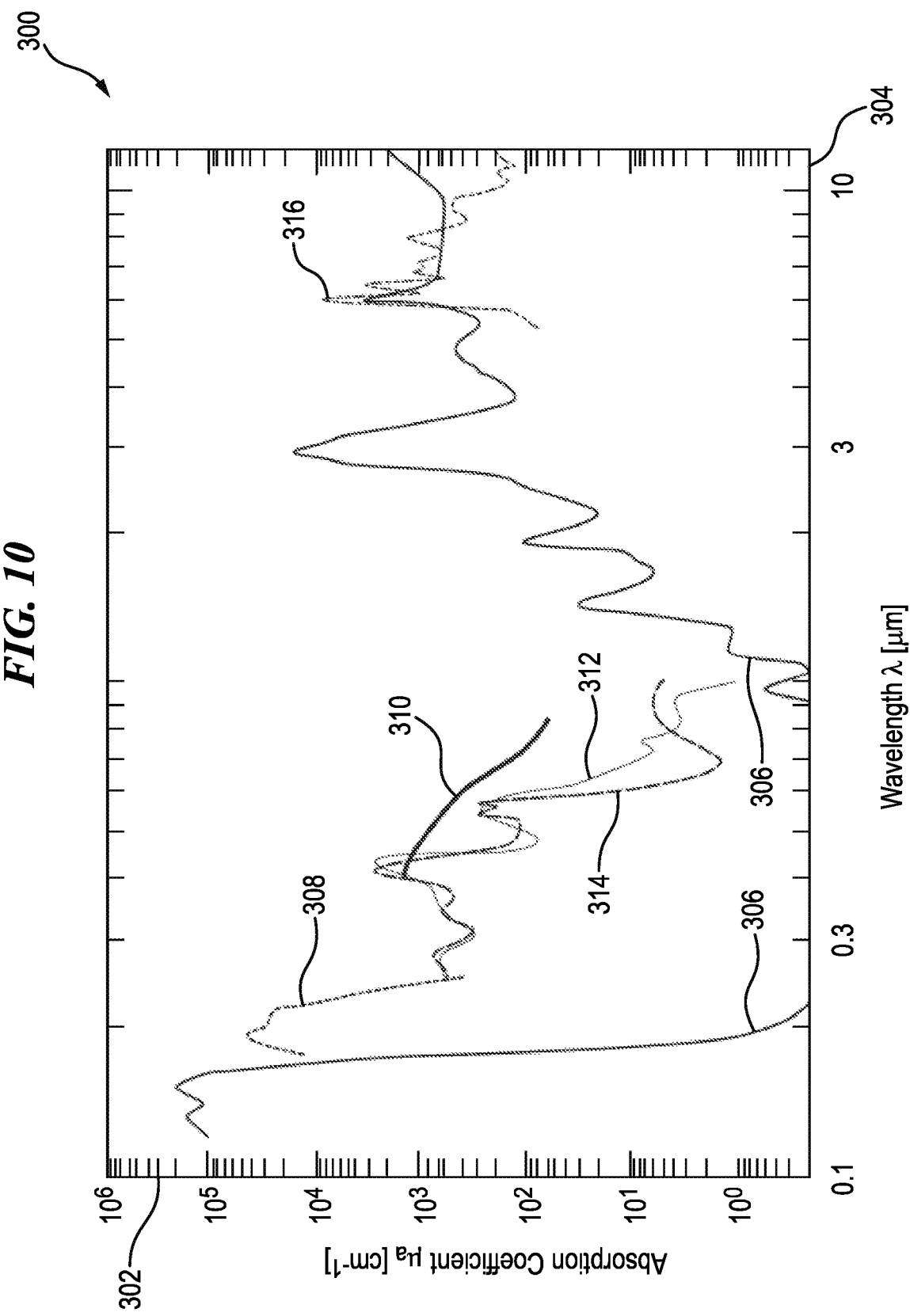
FIG. 10 is a graph showing wavelength versus absorption coefficient for various biological materials.

FIG. 10 shows a graph 300 depicting how the absorption coefficient of various biological materials varies across the EMR wavelength spectrum. In the graph 300, the vertical axis 302 represents absorption coefficient of the biological material in $cm^{-1}$, and the horizontal axis 304 represents EMR wavelength in µm. A first line 306 in the graph 300 represents the absorption coefficient of water at various EMR wavelengths, a second line 308 represents the absorption coefficient of protein at various EMR wavelengths, a third line 310 represents the absorption coefficient of melanin at various EMR wavelengths, a fourth line 312 represents the absorption coefficient of deoxygenated hemoglobin at various EMR wavelengths, a fifth line 314 represents the absorption coefficient of oxygenated hemoglobin at various EMR wavelengths, and a sixth line 316 represents the absorption coefficient of collagen at various EMR wavelengths. Different tissue types have different combinations of constituent materials and, therefore, the tissue type(s)

being visualized by a surgical visualization system can be identified and differentiated between according to the particular combination of detected constituent materials. Accordingly, a spectral imaging system of a surgical visualization system can be configured to emit EMR at a number of different wavelengths, determine the constituent materials of the tissue based on the detected absorption EMR absorption response at the different wavelengths, and then characterize the tissue type based on the particular detected combination of constituent materials.

Figure 11:
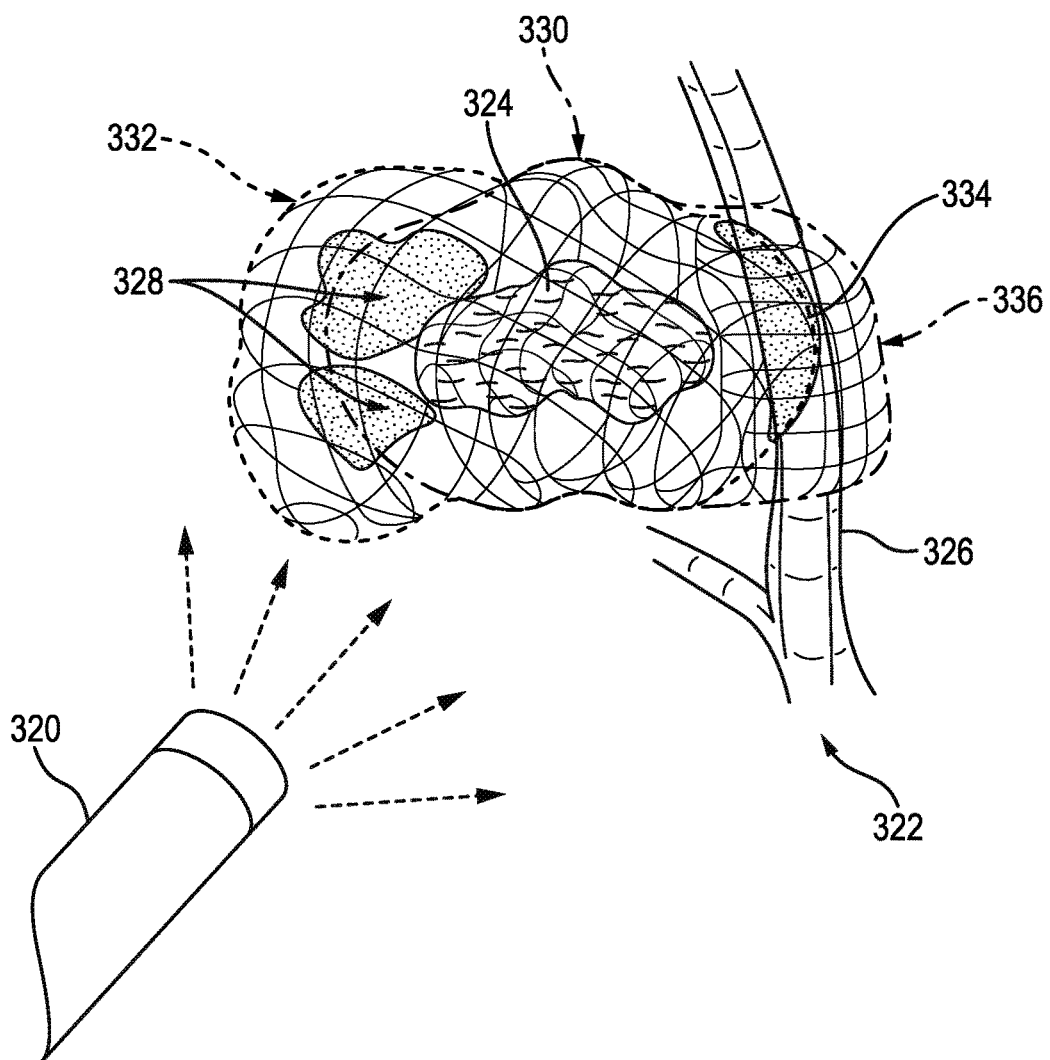
FIG. 11 is a schematic view of one embodiment of a spectral emitter visualizing a surgical site.

FIG. 11 shows an embodiment of the utilization of spectral imaging techniques to visualize different tissue types and/or anatomical structures. In FIG. 11, a spectral emitter 320 (e.g., the spectral light source 150 of FIG. 4) is being utilized by an imaging system to visualize a surgical site 322. The EMR emitted by the spectral emitter 320 and reflected from the tissues and/or structures at the surgical site 322 is received by an image sensor (e.g., the image sensor 135 of FIG. 4) to visualize the tissues and/or structures, which can be either visible (e.g., be located at a surface of the surgical site 322) or obscured (e.g., underlay other tissue and/or structures at the surgical site 322). In this embodiment, an imaging system (e.g., the imaging system 142 of FIG. 4) visualizes a tumor 324, an artery 326, and various abnormalities 328 (e.g., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system (e.g., the display 146 of the imaging system 142 of FIG. 4), on a primary display (e.g., the primary display 819 of FIG. 19), on a non-sterile display (e.g., the non-sterile displays 807, 809 of FIG. 19), on a display of a surgical hub (e.g., the display of the surgical hub 806 of FIG. 19), on a device/instrument display, and/or on another display.

The imaging system can be configured to tailor or update the displayed surgical site visualization according to the identified tissue and/or structure types. For example, as shown in FIG. 11, the imaging system can display a margin 330 associated with the tumor 324 being visualized on a display screen associated with or coupled to the imaging system, on a primary display, on a non-sterile display, on a display of a surgical hub, on a device/instrument display, and/or on another display. The margin 330 can indicate the area or amount of tissue that should be excised to ensure complete removal of the tumor 324. The surgical visualization system's control system (e.g., the control system 133 of FIG. 4) can be configured to control or update the dimensions of the margin 330 based on the tissues and/or structures identified by the imaging system. In this illustrated embodiment, the imaging system has identified multiple abnormalities 328 within the field of view (FOV). Accordingly, the control system can adjust the displayed margin 330 to a first updated margin 332 having sufficient dimensions to encompass the abnormalities 328. Further, the imaging system has also identified the artery 326 partially overlapping with the initially displayed margin 330 (as indicated by a highlighted region 334 of the artery 326). Accordingly, the control system can adjust the displayed margin to a second updated margin 336 having sufficient dimensions to encompass the relevant portion of the artery 326.

Figure 12:
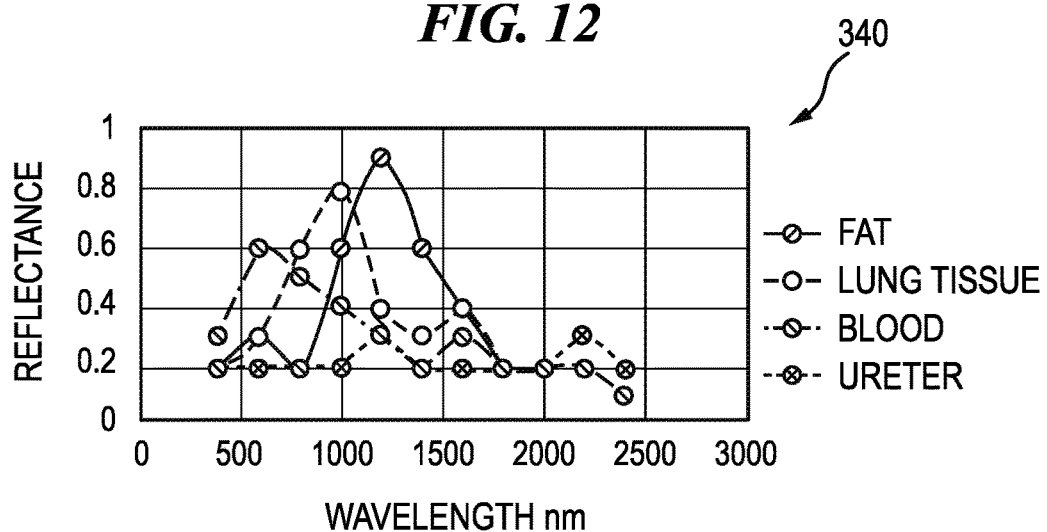
FIG. 12 is a graph depicting illustrative hyperspectral identifying signatures to differentiate a ureter from obscurants.
Figure 13:
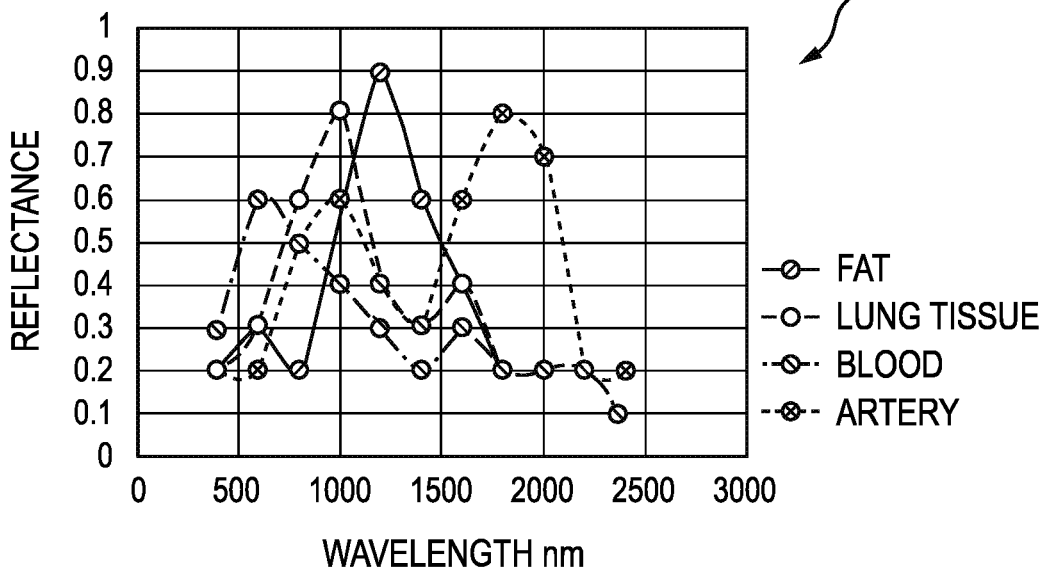
FIG. 13 is a graph depicting illustrative hyperspectral identifying signatures to differentiate an artery from obscurants.
Figure 14:
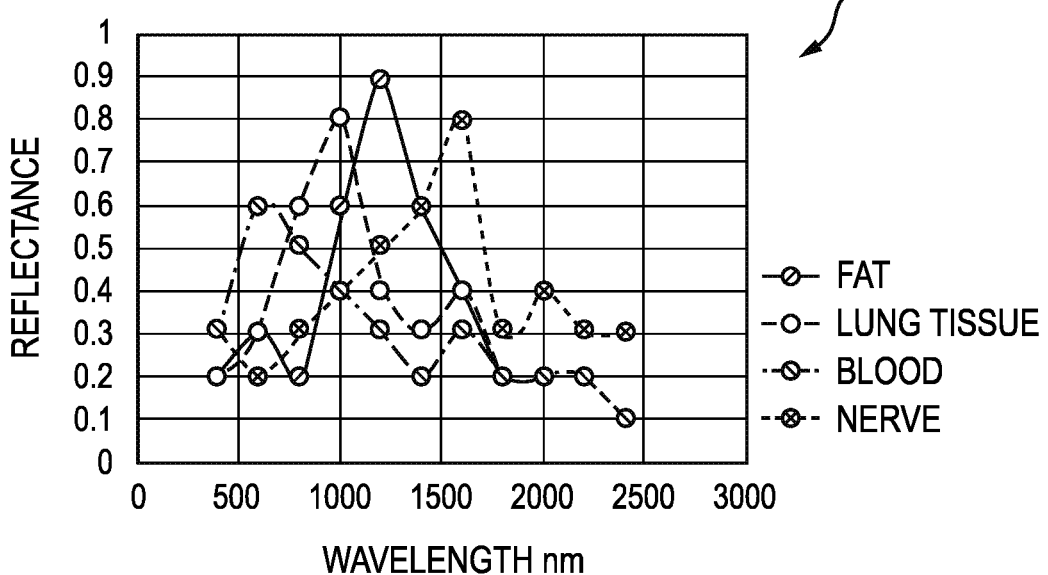
FIG. 14 is a graph depicting illustrative hyperspectral identifying signatures to differentiate a nerve from obscurants.

Tissues and/or structures can also be imaged or characterized according to their reflective characteristics, in addition to or in lieu of their absorptive characteristics described above with respect to FIG. 10 and FIG. 11, across the EMR wavelength spectrum. For example, FIG. 12, FIG. 13, and FIG. 14 illustrate various graphs of reflectance of different types of tissues or structures across different EMR wavelengths. FIG. 12 is a graphical representation 340 of an illustrative ureter signature versus obscurants. FIG. 13 is a graphical representation 342 of an illustrative artery signature versus obscurants. FIG. 14 is a graphical representation 344 of an illustrative nerve signature versus obscurants. The plots in FIG. 12, FIG. 13, and FIG. 14 represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

Select wavelengths for spectral imaging can be identified and utilized based on the anticipated critical structures and/or obscurants at a surgical site (e.g., "selective spectral" imaging). By utilizing selective spectral imaging, the amount of time required to obtain the spectral image can be minimized such that the information can be obtained in real-time and utilized intraoperatively. The wavelengths can be selected by a medical practitioner or by a control circuit based on input by a user, e.g., a medical practitioner. In certain instances, the wavelengths can be selected based on machine learning and/or big data accessible to the control circuit via, e.g., a cloud or surgical hub.

FIG. 15 illustrates one embodiment of spectral imaging to tissue being utilized intraoperatively to measure a distance between a waveform emitter and a critical structure that is obscured by tissue. FIG. 15 shows an embodiment of a time-of-flight sensor system 404 utilizing waveforms 424, 425. The time-of-flight sensor system 404 can be incorporated into a surgical visualization system, e.g., as the sensor system 104 of the surgical visualization system 100 of FIG. 1. The time-of-flight sensor system 404 includes a waveform emitter 406 and a waveform receiver 408 on the same surgical device 402 (e.g., the emitter 106 and the receiver 108 on the same surgical device 102 of FIG. 1). The emitted wave 400 extends to a critical structure 401 (e.g., the critical structure 101 of FIG. 1) from the emitter 406, and the received wave 425 is reflected back to by the receiver 408 from the critical structure 401. The surgical device 402 in this illustrated embodiment is positioned through a trocar 410 that extends into a cavity 407 in a patient. Although the trocar 410 is used in this in this illustrated embodiment, other trocars or other access devices can be used, or no access device may be used.

The waveforms 424, 425 are configured to penetrate obscuring tissue 403, such as by having wavelengths in the NIR or SWIR spectrum of wavelengths. A spectral signal (e.g., hyperspectral, multispectral, or selective spectral) or a photoacoustic signal is emitted from the emitter 406, as shown by a first arrow 407 pointing distally, and can penetrate the tissue 403 in which the critical structure 401 is concealed. The emitted waveform 424 is reflected by the critical structure 401, as shown by a second arrow 409 pointing proximally. The received waveform 425 can be delayed due to a distance d between a distal end of the surgical device 402 and the critical structure 401. The waveforms 424, 425 can be selected to target the critical structure 401 within the tissue 403 based on the spectral signature of the critical structure 401, as described herein. The emitter 406 is configured to provide a binary signal on and off, as shown in FIG. 16, for example, which can be measured by the receiver 408.

Based on the delay between the emitted wave 424 and the received wave 425, the time-of-flight sensor system 404 is configured to determine the distance d. A time-of-flight timing diagram 430 for the emitter 406 and the receiver 408 of FIG. 15 is shown in FIG. 16. The delay is a function of the distance d and the distance d is given by:

$$d = \frac{ct}{2} \cdot \frac{q_2}{q_1 + q_2}$$

where c=the speed of light; t=length of pulse; q1=accumulated charge while light is emitted; and q2=accumulated charge while light is not being emitted.

The time-of-flight of the waveforms 424, 425 corresponds to the distance d in FIG. 15. In various instances, additional emitters/receivers and/or pulsing signals from the emitter 406 can be configured to emit a non-penetrating signal. The non-penetrating signal can be configured to determine the distance from the emitter 406 to the surface 405 of the obscuring tissue 403. In various instances, a depth of the critical structure 401 can be determined by:

$$d_A = d_w - d_t$$

where $d_A$=the depth of the critical structure 401; $d_w$=the distance from the emitter 406 to the critical structure 401 (d in FIG. 15); and $d_t$=the distance from the emitter 406 (on the distal end of the surgical device 402) to the surface 405 of the obscuring tissue 403.

Figure 17:
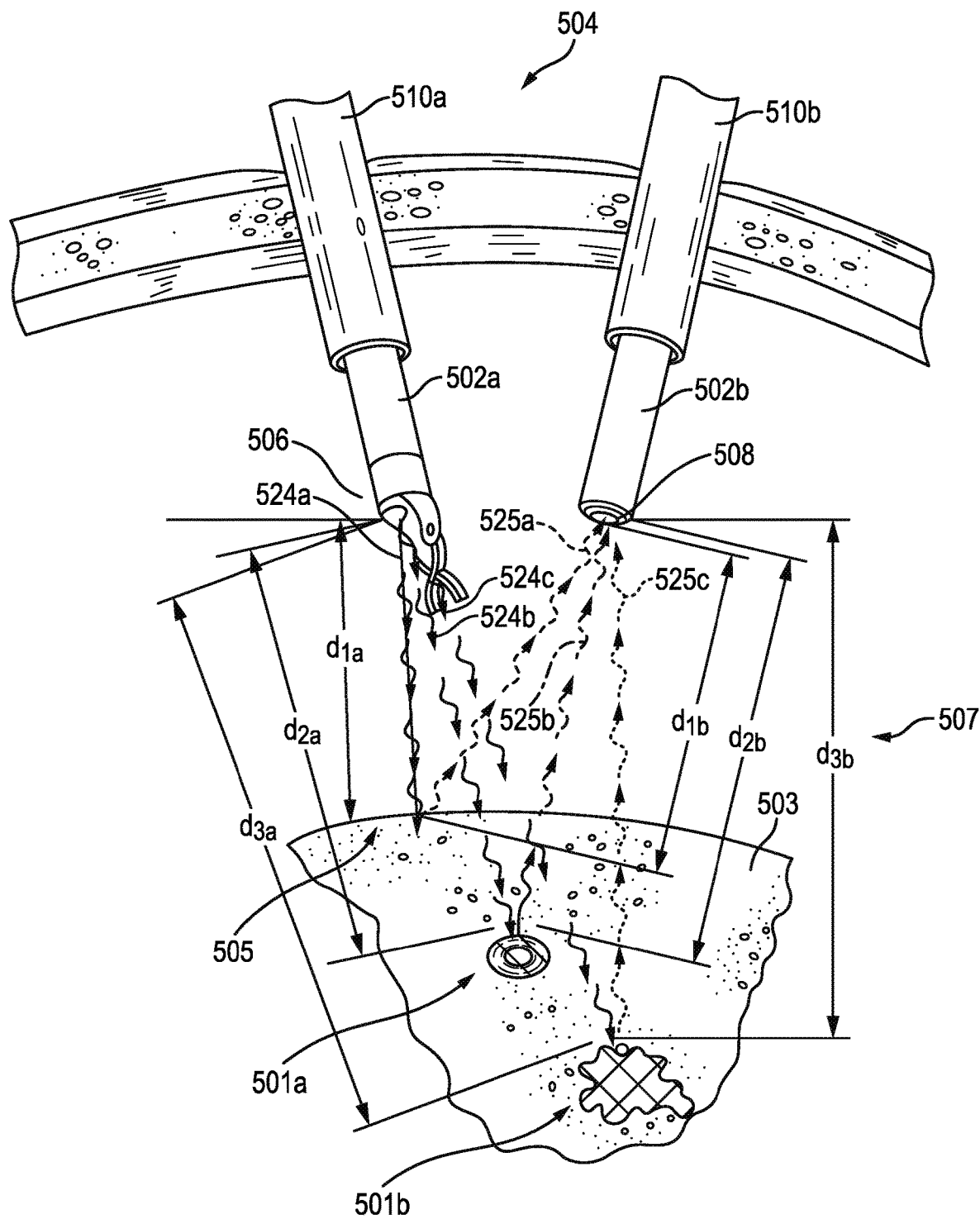
FIG. 17 is a schematic view of another embodiment of a near infrared (NIR) time-of-flight measurement system being utilized intraoperatively.

FIG. 17 illustrates another embodiment of a time-of-flight sensor system 504 utilizing waves 524a, 524b, 524c, 525a, 525b, 525c is shown. The time-of-flight sensor system 504 can be incorporated into a surgical visualization system, e.g., as the sensor system 104 of the surgical visualization system 100 of FIG. 1. The time-of-flight sensor system 504 includes a waveform emitter 506 and a waveform receiver 508 (e.g., the emitter 106 and the receiver 108 of FIG. 1). The waveform emitter 506 is positioned on a first surgical device 502a (e.g., the surgical device 102 of FIG. 1), and the waveform receiver 508 is positioned on a second surgical device 502b. The surgical devices 502a, 502b are positioned through first and second trocars 510a, 510b, respectively, which extend into a cavity 507 in a patient. Although the trocars 510a, 510b are used in this in this illustrated embodiment, other trocars or other access devices can be used, or no access device may be used. The emitted waves 524a, 524b, 524c extend toward a surgical site from the emitter 506, and the received waves 525a, 525b, 525c are reflected back to the receiver 508 from various structures and/or surfaces at the surgical site.

The different emitted waves 524a, 524b, 524c are configured to target different types of material at the surgical site. For example, the wave 524a targets obscuring tissue 503, the wave 524b targets a first critical structure 501a (e.g., the critical structure 101 of FIG. 1), which is a vessel in this illustrated embodiment, and the wave 524c targets a second critical structure 501b (e.g., the critical structure 101 of FIG. 1), which is a cancerous tumor in this illustrated embodiment. The wavelengths of the waves 524a, 524b, 524c can be in the visible light, NIR, or SWIR spectrum of wavelengths. For example, visible light can be reflected off a surface 505 of the tissue 503, and NIR and/or SWIR waveforms can penetrate the surface 505 of the tissue 503. In various aspects, as described herein, a spectral signal (e.g., hyperspectral, multispectral, or selective spectral) or a photoacoustic signal can be emitted from the emitter 506. The waves 524b, 524c can be selected to target the critical structures 501a, 501b within the tissue 503 based on the spectral signature of the critical structure 501a, 501b, as described herein. Photoacoustic imaging is further described in various U.S. patent applications, which are incorporated by reference herein in the present disclosure.

The emitted waves 524a, 524b, 524c are reflected off the targeted material, namely the surface 505, the first critical structure 501a, and the second structure 501b, respectively. The received waveforms 525a, 525b, 525c can be delayed due to distances $d_{1a}$, $d_{2a}$, $d_{3a}$, $d_{1b}$, $d_{2b}$, $d_{2c}$.

In the time-of-flight sensor system 504, in which the emitter 506 and the receiver 508 are independently positionable (e.g., on separate surgical devices 502a, 502b and/or controlled by separate robotic arms), the various distances $d_{1a}$, $d_{2a}$, $d_{3a}$, $d_{1b}$, $d_{2b}$, $d_{2c}$ can be calculated from the known position of the emitter 506 and the receiver 508. For example, the positions can be known when the surgical devices 502a, 502b are robotically-controlled. Knowledge of the positions of the emitter 506 and the receiver 508, as well as the time of the photon stream to target a certain tissue and the information received by the receiver 508 of that particular response can allow a determination of the distances $d_{1a}$, $d_{2a}$, $d_{3a}$, $d_{1b}$, $d_{2b}$, $d_{2c}$. In one aspect, the distance to the obscured critical structures 501a, 501b can be triangulated using penetrating wavelengths. Because the speed of light is constant for any wavelength of visible or invisible light, the time-of-flight sensor system 504 can determine the various distances.

In a view provided to the medical practitioner, such as on a display, the receiver 508 can be rotated such that a center of mass of the target structure in the resulting images remains constant, e.g., in a plane perpendicular to an axis of a select target structure 503, 501a, or 501b. Such an orientation can quickly communicate one or more relevant distances and/or perspectives with respect to the target structure. For example, as shown in FIG. 17, the surgical site is displayed from a viewpoint in which the critical structure 501a is perpendicular to the viewing plane (e.g., the vessel is oriented in/out of the page). Such an orientation can be default setting; however, the view can be rotated or otherwise adjusted by a medical practitioner. In certain instances, the medical practitioner can toggle between different surfaces and/or target structures that define the viewpoint of the surgical site provided by the imaging system.

As in this illustrated embodiment, the receiver 508 can be mounted on the trocar 510b (or other access device) through which the surgical device 502b is positioned. In other embodiments, the receiver 508 can be mounted on a separate robotic arm for which the three-dimensional position is known. In various instances, the receiver 508 can be mounted on a movable arm that is separate from a robotic surgical system that controls the surgical device 502a or can be mounted to an operating room (OR) table or fixture that is intraoperatively registerable to the robot coordinate plane. In such instances, the position of the emitter 506 and the receiver 508 can be registerable to the same coordinate plane such that the distances can be triangulated from outputs from the time-of-flight sensor system 504.

Combining time-of-flight sensor systems and near-infrared spectroscopy (NIRS), termed TOF-NIRS, which is capable of measuring the time-resolved profiles of NIR light with nanosecond resolution can be found in "Time-Of-Flight Near-Infrared Spectroscopy For Nondestructive Measurement Of Internal Quality In Grapefruit," Journal of the American Society for Horticultural Science, May 2013 vol. 138 no. 3 225-228, which is hereby incorporated by reference in its entirety.

Embodiments of visualization systems and aspects and uses thereof are described further in U.S. Pat. Pub. No. 2020/0015923 entitled "Surgical Visualization Platform" filed Sep. 11, 2018, U.S. Pat. Pub. No. 2020/0015900 entitled "Controlling An Emitter Assembly Pulse Sequence" filed Sep. 11, 2018, U.S. Pat. Pub. No. 2020/0015668 entitled "Singular EMR Source Emitter Assembly" filed Sep. 11, 2018, U.S. Pat. Pub. No. 2020/0015925 entitled "Combination Emitter And Camera Assembly" filed Sep. 11, 2018, U.S. Pat. Pub. No. 2020/00015899 entitled "Surgical Visualization With Proximity Tracking Features" filed Sep. 11, 2018, U.S. Pat. Pub. No. 2020/00015903 entitled "Surgical Visualization Of Multiple Targets" filed Sep. 11, 2018, U.S. Pat. No. 10,792,034 entitled "Visualization Of Surgical Devices" filed Sep. 11, 2018, U.S. Pat. Pub. No. 2020/0015897 entitled "Operative Communication Of Light" filed Sep. 11, 2018, U.S. Pat. Pub. No. 2020/0015924 entitled "Robotic Light Projection Tools" filed Sep. 11, 2018, U.S. Pat. Pub. No. 2020/0015898 entitled "Surgical Visualization Feedback System" filed Sep. 11, 2018, U.S. Pat. Pub. No. 2020/0015906 entitled "Surgical Visualization And Monitoring" filed Sep. 11, 2018, U.S. Pat. Pub. No. 2020/0015907 entitled "Integration Of Imaging Data" filed Sep. 11, 2018, U.S. Pat. No. 10,925,598 entitled "Robotically-Assisted Surgical Suturing Systems" filed Sep. 11, 2018, U.S. Pat. Pub. No. 2020/0015901 entitled "Safety Logic For Surgical Suturing Systems" filed Sep. 11, 2018, U.S. Pat. Pub. No. 2020/0015914 entitled "Robotic Systems With Separate Photoacoustic Receivers" filed Sep. 11, 2018, U.S. Pat. Pub. No. 2020/0015902 entitled "Force Sensor Through Structured Light Deflection" filed Sep. 11, 2018, U.S. Pat. Pub. No. 2019/0201136 entitled "Method Of Hub Communication" filed Dec. 4, 2018, U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, U.S. patent application Ser. No. 16/729,807 entitled "Method Of Using Imaging Devices In Surgery" filed Dec. 30, 2019, U.S. Prov. Pat. App. No. 63/249,652 entitled "Surgical Devices, Systems, and Methods Using Fiducial Identification and Tracking" filed on Sep. 29, 2021, U.S. Prov. Pat. App. No. 63/249,658 entitled "Surgical Devices, Systems, and Methods for Control of One Visualization with Another" filed on Sep. 29, 2021, U.S. Prov. Pat. App. No. 63/249,870 entitled "Methods and Systems for Controlling Cooperative Surgical Instruments" filed on Sep. 29, 2021, U.S. Prov. Pat. App. No. 63/249,881 entitled "Methods and Systems for Controlling Cooperative Surgical Instruments with Variable Surgical Site Access Trajectories" filed on Sep. 29, 2021, U.S. Prov. Pat. App. No. 63/249,877 entitled "Methods and Systems for Controlling Cooperative Surgical Instruments" filed on Sep. 29, 2021, and U.S. Prov. Pat. App. No. 63/249,980 entitled "Cooperative Access" filed on Sep. 29, 2021, which are hereby incorporated by reference in their entireties.

Surgical Hubs

The various visualization or imaging systems described herein can be incorporated into a system that includes a surgical hub. In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as one or more surgical instruments that are used to conduct medical procedures on patients and/or one or more visualization systems that are used during performance of medical procedures. The surgical hubs provide a wide array of functionality to improve the outcomes of medical procedures. The data generated by the various surgical devices, visualization systems, and surgical hubs about the patient and the medical procedure may be transmitted to the cloud-based medical analytics system. This data may then be aggregated with similar data gathered from many other surgical hubs, visualization systems, and surgical instruments located at other medical facilities. Various patterns and correlations may be found through the cloud-based analytics system analyzing the collected data. Improvements in the techniques used to generate the data may be generated as a result, and these improvements may then be disseminated to the various surgical hubs, visualization systems, and surgical instruments. Due to the interconnectedness of all of the aforementioned components, improvements in medical procedures and practices may be found that otherwise may not be found if the many components were not so interconnected.

Examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0201046 entitled "Method For Controlling Smart Energy Devices" filed Dec. 4, 2018, U.S. Pat. Pub. No. 2019/0201114 entitled "Adaptive Control Program Updates For Surgical Hubs" filed Mar. 29, 2018, U.S. Pat. Pub. No. 2019/0201140 entitled "Surgical Hub Situational Awareness" filed Mar. 29, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0206555 entitled "Cloud-based Medical Analytics For Customization And Recommendations To A User" filed Mar. 29, 2018, and U.S. Pat. Pub. No. 2019/0207857 entitled "Surgical Network Determination Of Prioritization Of Communication, Interaction, Or Processing Based On System Or Device Needs" filed Nov. 6, 2018, which are hereby incorporated by reference in their entireties.

Figure 18:
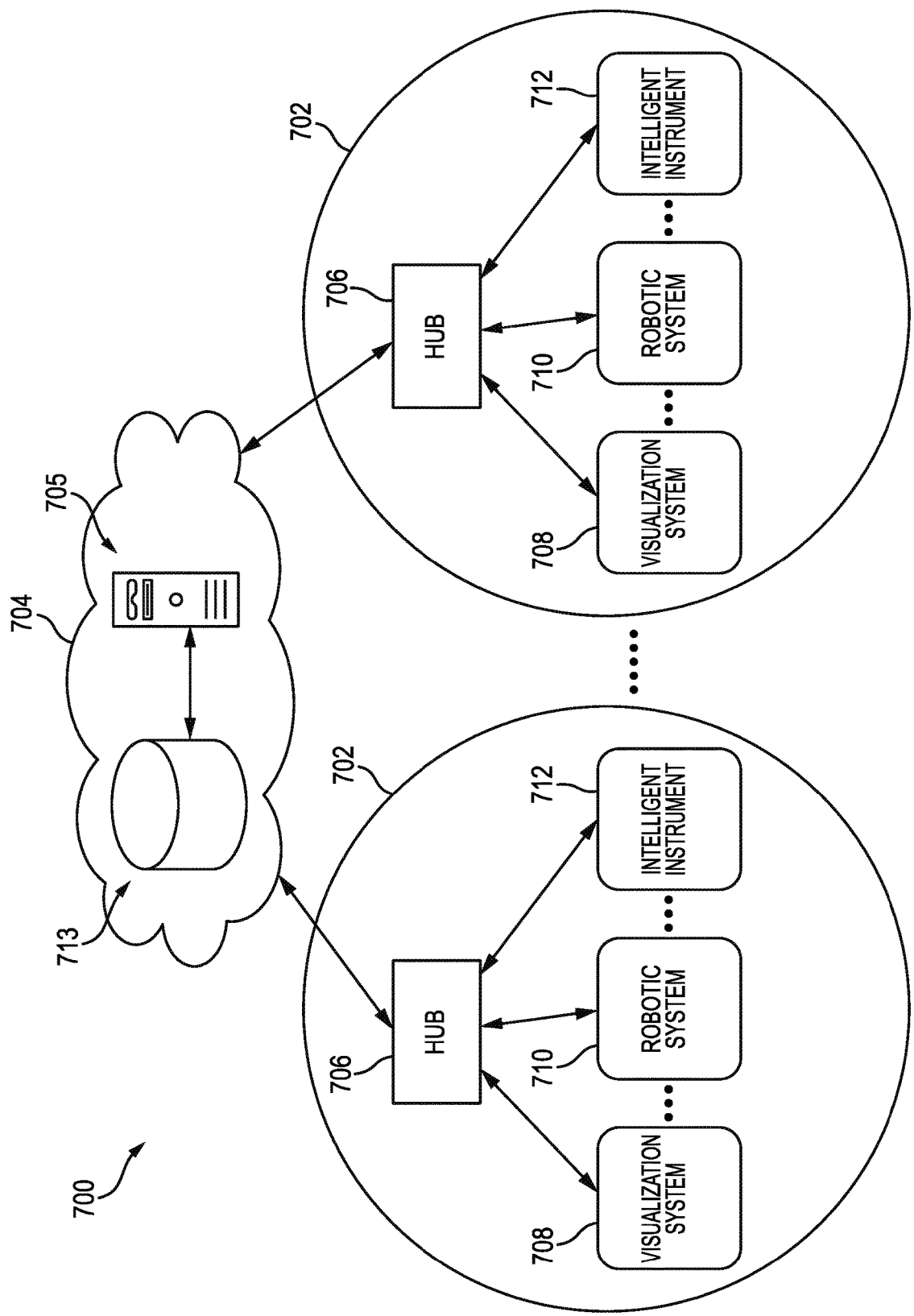
FIG. 18 is a schematic view of one embodiment of a computer-implemented interactive surgical system.

FIG. 18 illustrates one embodiment of a computer-implemented interactive surgical system 700 that includes one or more surgical systems 702 and a cloud-based system (e.g., a cloud 704 that can include a remote server 713 coupled to a storage device 705). Each surgical system 702 includes at least one surgical hub 706 in communication with the cloud 704. In one example, as illustrated in FIG. 18, the surgical system 702 includes a visualization system 708, a robotic system 710, and an intelligent (or "smart") surgical instrument 712, which are configured to communicate with one another and/or the hub 706. The intelligent surgical instrument 712 can include imaging device(s). The surgical system 702 can include an M number of hubs 706, an N number of visualization systems 708, an O number of robotic systems 710, and a P number of intelligent surgical instruments 712, where M, N, O, and P are integers greater than or equal to one that may or may not be equal to any one or more of each other. Various exemplary intelligent surgical instruments and robotic systems are described herein.

Data received by a surgical hub from a surgical visualization system can be used in any of a variety of ways. In an exemplary embodiment, the surgical hub can receive data from a surgical visualization system in use with a patient in a surgical setting, e.g., in use in an operating room during performance of a surgical procedure. The surgical hub can use the received data in any of one or more ways, as discussed herein.

The surgical hub can be configured to analyze received data in real time with use of the surgical visualization system and adjust control one or more of the surgical visualization system and/or one or more intelligent surgical instruments in use with the patient based on the analysis of the received data. Such adjustment can include, for example, adjusting one or operational control parameters of intelligent surgical instrument(s), causing one or more sensors of one or more intelligent surgical instruments to take a measurement to help gain an understanding of the patient's current physiological condition, and/or current operational status of an intelligent surgical instrument, and other adjustments. Controlling and adjusting operation of intelligent surgical instruments is discussed further below. Examples of operational control parameters of an intelligent surgical instrument include motor speed, cutting element speed, time, duration, level of energy application, and light emission. Examples of surgical hubs and of controlling and adjusting intelligent surgical instrument operation are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019, and in U.S. patent application Ser. No. 17/068,857 entitled "Adaptive Responses From Smart Packaging Of Drug Delivery Absorbable Adjuncts" filed Oct. 13, 2020, U.S. patent application Ser. No. 17/068,858 entitled "Drug Administration Devices That Communicate With Surgical Hubs" filed Oct. 13, 2020, U.S. patent application Ser. No. 17/068,859 entitled "Controlling Operation Of Drug Administration Devices Using Surgical Hubs" filed Oct. 13, 2020, U.S. patent application Ser. No. 17/068,863 entitled "Patient Monitoring Using Drug Administration Devices" filed Oct. 13, 2020, U.S. patent application Ser. No. 17/068,865 entitled "Monitoring And Communicating Information Using Drug Administration Devices" filed Oct. 13, 2020, and U.S. patent application Ser. No. 17/068,867 entitled "Aggregating And Analyzing Drug Administration Data" filed Oct. 13, 2020, which are hereby incorporated by reference in their entireties.

The surgical hub can be configured to cause visualization of the received data to be provided in the surgical setting on a display so that a medical practitioner in the surgical setting can view the data and thereby receive an understanding of the operation of the imaging device(s) in use in the surgical setting. Such information provided via visualization can include text and/or images.

Figure 19:
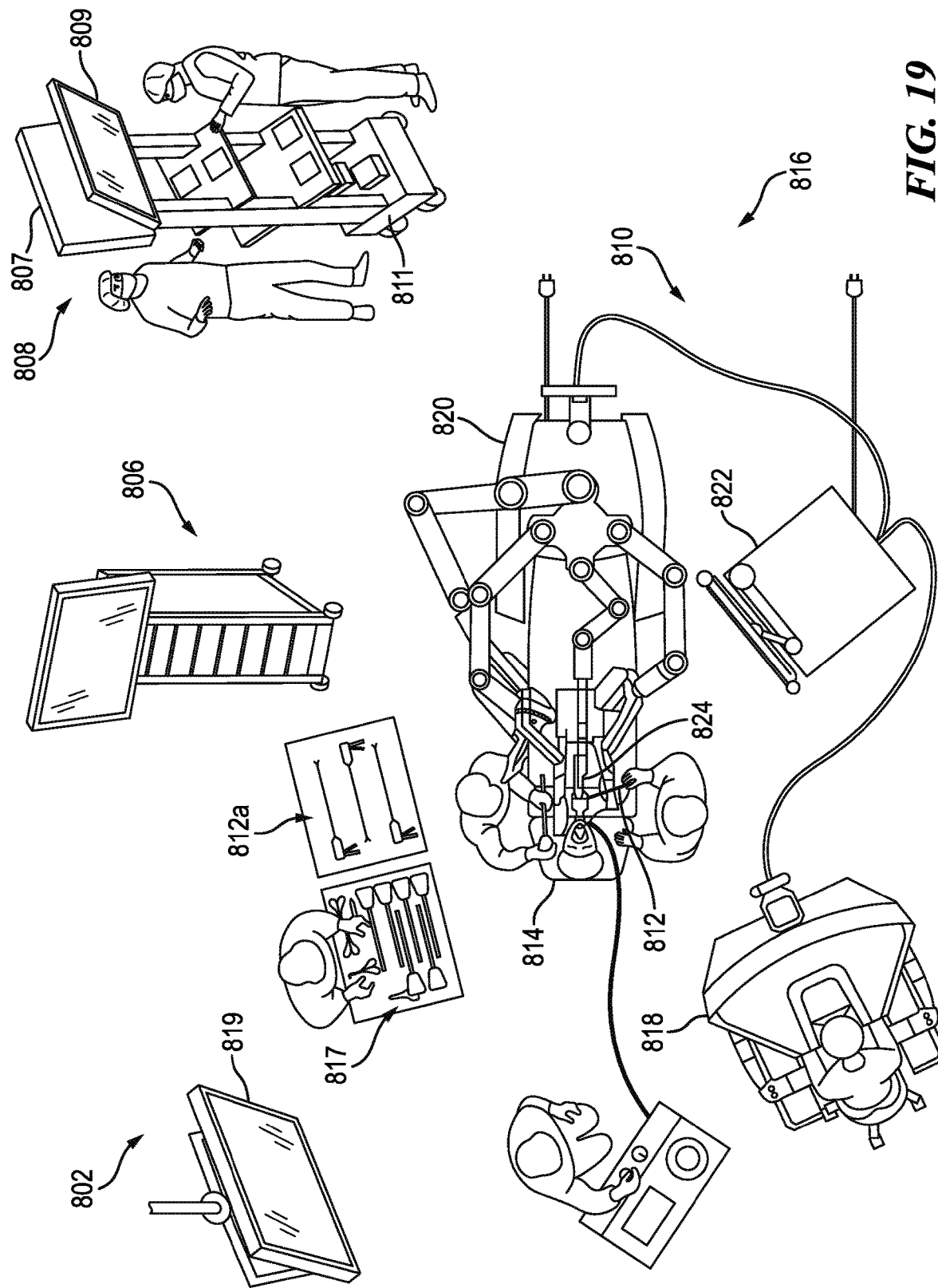
FIG. 19 is a schematic view of one embodiment a surgical system being used to perform a surgical procedure in an operating room.

FIG. 19 illustrates one embodiment of a surgical system 802 including a surgical hub 806 (e.g., the surgical hub 706 of FIG. 18 or other surgical hub described herein), a robotic surgical system 810 (e.g., the robotic surgical system 110 of FIG. 1 or other robotic surgical system herein), and a visualization system 808 (e.g., the visualization system 100 of FIG. 1 or other visualization system described herein). The surgical hub 806 can be in communication with a cloud, as discussed herein. FIG. 19 shows the surgical system 802 being used to perform a surgical procedure on a patient who is lying down on an operating table 814 in a surgical operating room 816. The robotic system 810 includes a surgeon's console 818, a patient side cart 820 (surgical robot), and a robotic system surgical hub 822. The robotic system surgical hub 822 is generally configured similar to the surgical hub 822 and can be in communication with a cloud. In some embodiments, the robotic system surgical hub 822 and the surgical hub 806 can be combined. The patient side cart 820 can manipulate an intelligent surgical tool 812 through a minimally invasive incision in the body of the patient while a medical practitioner, e.g., a surgeon, nurse, and/or other medical practitioner, views the surgical site through the surgeon's console 818. An image of the surgical site can be obtained by an imaging device 824 (e.g., the imaging device 120 of FIG. 1 or other imaging device described herein), which can be manipulated by the patient side cart 820 to orient the imaging device 824. The robotic system surgical hub 822 can be used to process the images of the surgical site for subsequent display to the surgeon through the surgeon's console 818.

A primary display 819 is positioned in the sterile field of the operating room 816 and is configured to be visible to an operator at the operating table 814. In addition, as in this illustrated embodiment, a visualization tower 818 can positioned outside the sterile field. The visualization tower 818 includes a first non-sterile display 807 and a second non-sterile display 809, which face away from each other. The visualization system 808, guided by the surgical hub 806, is configured to utilize the displays 807, 809, 819 to coordinate information flow to medical practitioners inside and outside the sterile field. For example, the surgical hub 806 can cause the visualization system 808 to display a snapshot and/or a video of a surgical site, as obtained by the imaging device 824, on one or both of the non-sterile displays 807, 809, while maintaining a live feed of the surgical site on the primary display 819. The snapshot and/or video on the non-sterile display 807 and/or 809 can permit a non-sterile medical practitioner to perform a diagnostic step relevant to the surgical procedure, for example.

The surgical hub 806 is configured to route a diagnostic input or feedback entered by a non-sterile medical practitioner at the visualization tower 818 to the primary display 819 within the sterile field, where it can be viewed by a sterile medical practitioner at the operating table 814. For example, the input can be in the form of a modification to the snapshot and/or video displayed on the non-sterile display 807 and/or 809, which can be routed to the primary display 819 by the surgical hub 806.

The surgical hub 806 is configured to coordinate information flow to a display of the intelligent surgical instrument 812, as is described in various U.S. Patent Applications that are incorporated by reference herein in the present disclosure. A diagnostic input or feedback entered by a non-sterile operator at the visualization tower 818 can be routed by the surgical hub 806 to the display 819 within the sterile field, where it can be viewed by the operator of the surgical instrument 812 and/or by other medical practitioner(s) in the sterile field.

The intelligent surgical instrument 812 and the imaging device 824, which is also an intelligent surgical tool, is being used with the patient in the surgical procedure as part of the surgical system 802. Other intelligent surgical instruments 812a that can be used in the surgical procedure, e.g., that can be removably coupled to the patient side cart 820 and be in communication with the robotic surgical system 810 and the surgical hub 806, are also shown in FIG. 19 as being available. Non-intelligent (or "dumb") surgical instruments 817, e.g., scissors, trocars, cannulas, scalpels, etc., that cannot be in communication with the robotic surgical system 810 and the surgical hub 806 are also shown in FIG. 19 as being available for use.

Operating Intelligent Surgical Instruments

An intelligent surgical device can have an algorithm stored thereon, e.g., in a memory thereof, configured to be executable on board the intelligent surgical device, e.g., by a processor thereof, to control operation of the intelligent surgical device. In some embodiments, instead of or in addition to being stored on the intelligent surgical device, the algorithm can be stored on a surgical hub, e.g., in a memory thereof, that is configured to communicate with the intelligent surgical device.

The algorithm is stored in the form of one or more sets of pluralities of data points defining and/or representing instructions, notifications, signals, etc. to control functions of the intelligent surgical device. In some embodiments, data gathered by the intelligent surgical device can be used by the intelligent surgical device, e.g., by a processor of the intelligent surgical device, to change at least one variable parameter of the algorithm. As discussed above, a surgical hub can be in communication with an intelligent surgical device, so data gathered by the intelligent surgical device can be communicated to the surgical hub and/or data gathered by another device in communication with the surgical hub can be communicated to the surgical hub, and data can be communicated from the surgical hub to the intelligent surgical device. Thus, instead of or in addition to the intelligent surgical device being configured to change a stored variable parameter, the surgical hub can be configured to communicate the changed at least one variable, alone or as part of the algorithm, to the intelligent surgical device and/or the surgical hub can communicate an instruction to the intelligent surgical device to change the at least one variable as determined by the surgical hub.

The at least one variable parameter is among the algorithm's data points, e.g., are included in instructions for operating the intelligent surgical device, and are thus each able to be changed by changing one or more of the stored pluralities of data points of the algorithm. After the at least one variable parameter has been changed, subsequent execution of the algorithm is according to the changed algorithm. As such, operation of the intelligent surgical device over time can be managed for a patient to increase the beneficial results use of the intelligent surgical device by taking into consideration actual situations of the patient and actual conditions and/or results of the surgical procedure in which the intelligent surgical device is being used. Changing the at least one variable parameter is automated to improve patient outcomes. Thus, the intelligent surgical device can be configured to provide personalized medicine based on the patient and the patient's surrounding conditions to provide a smart system. In a surgical setting in which the intelligent surgical device is being used during performance of a surgical procedure, automated changing of the at least one variable parameter may allow for the intelligent surgical device to be controlled based on data gathered during the performance of the surgical procedure, which may help ensure that the intelligent surgical device is used efficiently and correctly and/or may help reduce chances of patient harm by harming a critical anatomical structure.

The at least one variable parameter can be any of a variety of different operational parameters. Examples of variable parameters include motor speed, motor torque, energy level, energy application duration, tissue compression rate, jaw closure rate, cutting element speed, load threshold, etc.

Figure 20:
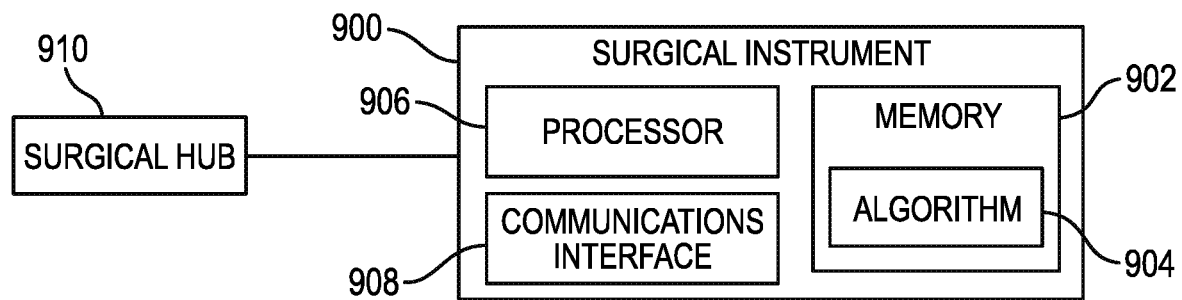
FIG. 20 is a schematic view of one embodiment of a surgical system including a smart surgical instrument and a surgical hub.

FIG. 20 illustrates one embodiment of an intelligent surgical instrument 900 including a memory 902 having an algorithm 904 stored therein that includes at least one variable parameter. The algorithm 904 can be a single algorithm or can include a plurality of algorithms, e.g., separate algorithms for different aspects of the surgical instrument's operation, where each algorithm includes at least one variable parameter. The intelligent surgical instrument 900 can be the surgical device 102 of FIG. 1, the imaging device 120 of FIG. 1, the surgical device 202 of FIG. 8, the imaging device 220 of FIG. 8, the surgical device 402 of FIG. 15, the surgical device 502a of FIG. 17, the surgical device 502b of FIG. 17, the surgical device 712 of FIG. 18, the surgical device 812 of FIG. 19, the imaging device 824 of FIG. 19, or other intelligent surgical instrument. The surgical instrument 900 also includes a processor 906 configured to execute the algorithm 904 to control operation of at least one aspect of the surgical instrument 900. To execute the algorithm 904, the processor 906 is configured to run a program stored in the memory 902 to access a plurality of data points of the algorithm 904 in the memory 902.

The surgical instrument 900 also includes a communications interface 908, e.g., a wireless transceiver or other wired or wireless communications interface, configured to communicate with another device, such as a surgical hub 910. The communications interface 908 can be configured to allow one-way communication, such as providing data to a remote server (e.g., a cloud server or other server) and/or to a local, surgical hub server, and/or receiving instructions or commands from a remote server and/or a local, surgical hub server, or two-way communication, such as providing information, messages, data, etc. regarding the surgical instrument 900 and/or data stored thereon and receiving instructions, such as from a doctor; a remote server regarding updates to software; a local, surgical hub server regarding updates to software; etc.

The surgical instrument 900 is simplified in FIG. 20 and can include additional components, e.g., a bus system, a handle, a elongate shaft having an end effector at a distal end thereof, a power source, etc. The processor 906 can also be configured to execute instructions stored in the memory 902 to control the device 900 generally, including other electrical components thereof such as the communications interface 908, an audio speaker, a user interface, etc.

The processor 906 is configured to change at least one variable parameter of the algorithm 904 such that a subsequent execution of the algorithm 904 will be in accordance with the changed at least one variable parameter. To change the at least one variable parameter of the algorithm 904, the processor 906 is configured to modify or update the data point(s) of the at least one variable parameter in the memory 902. The processor 906 can be configured to change the at least one variable parameter of the algorithm 904 in real time with use of the surgical device 900 during performance of a surgical procedure, which may accommodate real time conditions.

Additionally or alternatively to the processor 906 changing the at least one variable parameter, the processor 906 can be configured to change the algorithm 904 and/or at least one variable parameter of the algorithm 904 in response to an instruction received from the surgical hub 910. In some embodiments, the processor 906 is configured to change the at least one variable parameter only after communicating with the surgical hub 910 and receiving an instruction therefrom, which may help ensure coordinated action of the surgical instrument 900 with other aspects of the surgical procedure in which the surgical instrument 900 is being used.

In an exemplary embodiment, the processor 906 executes the algorithm 904 to control operation of the surgical instrument 900, changes the at least one variable parameter of the algorithm 904 based on real time data, and executes the algorithm 904 after changing the at least one variable parameter to control operation of the surgical instrument 900.

Figure 21:
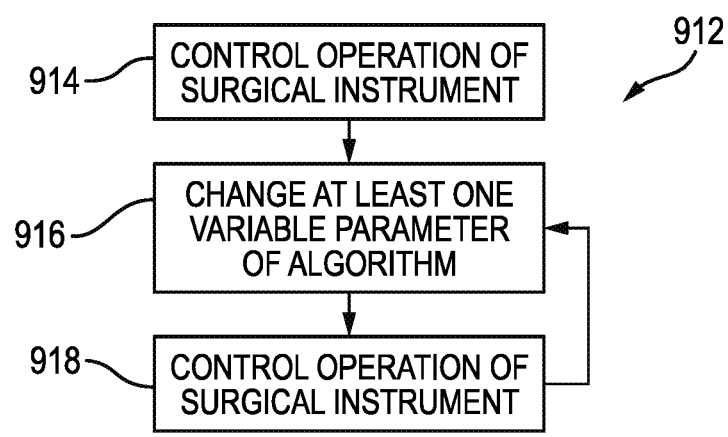
FIG. 21 is a flowchart showing a method of controlling the smart surgical instrument of FIG. 20.

FIG. 21 illustrates one embodiment of a method 912 of using of the surgical instrument 900 including a change of at least one variable parameter of the algorithm 904. The processor 906 controls 914 operation of the surgical instrument 900 by executing the algorithm 904 stored in the memory 902. Based on any of this subsequently known data and/or subsequently gathered data, the processor 904 changes 916 the at least one variable parameter of the algorithm 904 as discussed above. After changing the at least one variable parameter, the processor 906 controls 918 operation of the surgical instrument 900 by executing the algorithm 904, now with the changed at least one variable parameter. The processor 904 can change 916 the at least one variable parameter any number of times during performance of a surgical procedure, e.g., zero, one, two, three, etc. During any part of the method 912, the surgical instrument 900 can communicate with one or more computer systems, e.g., the surgical hub 910, a remote server such as a cloud server, etc., using the communications interface 908 to provide data thereto and/or receive instructions therefrom.

Situational Awareness

Operation of an intelligent surgical instrument can be altered based on situational awareness of the patient. The operation of the intelligent surgical instrument can be altered manually, such as by a user of the intelligent surgical instrument handling the instrument differently, providing a different input to the instrument, ceasing use of the instrument, etc. Additionally or alternatively, the operation of an intelligent surgical instrument can be changed automatically by an algorithm of the instrument being changed, e.g., by changing at least one variable parameter of the algorithm. As mentioned above, the algorithm can be adjusted automatically without user input requesting the change. Automating the adjustment during performance of a surgical procedure may help save time, may allow medical practitioners to focus on other aspects of the surgical procedure, and/or may ease the process of using the surgical instrument for a medical practitioner, which each may improve patient outcomes, such as by avoiding a critical structure, controlling the surgical instrument with consideration of a tissue type the instrument is being used on and/or near, etc.

The visualization systems described herein can be utilized as part of a situational awareness system that can be embodied or executed by a surgical hub, e.g., the surgical hub 706, the surgical hub 806, or other surgical hub described herein. In particular, characterizing, identifying, and/or visualizing surgical instruments (including their positions, orientations, and actions), tissues, structures, users, and/or other things located within the surgical field or the operating theater can provide contextual data that can be utilized by a situational awareness system to infer various information, such as a type of surgical procedure or a step thereof being performed, a type of tissue(s) and/or structure(s) being manipulated by a surgeon or other medical practitioner, and other information. The contextual data can then be utilized by the situational awareness system to provide alerts to a user, suggest subsequent steps or actions for the user to undertake, prepare surgical devices in anticipation for their use (e.g., activate an electrosurgical generator in anticipation of an electrosurgical instrument being utilized in a subsequent step of the surgical procedure, etc.), control operation of intelligent surgical instruments (e.g., customize surgical instrument operational parameters of an algorithm as discussed further below), and so on.

Although an intelligent surgical device including an algorithm that responds to sensed data, e.g., by having at least one variable parameter of the algorithm changed, can be an improvement over a "dumb" device that operates without accounting for sensed data, some sensed data can be incomplete or inconclusive when considered in isolation, e.g., without the context of the type of surgical procedure being performed or the type of tissue that is being operated on.

Without knowing the procedural context (e.g., knowing the type of tissue being operated on or the type of procedure being performed), the algorithm may control the surgical device incorrectly or sub-optimally given the particular context-free sensed data. For example, the optimal manner for an algorithm to control a surgical instrument in response to a particular sensed parameter can vary according to the particular tissue type being operated on. This is due to the fact that different tissue types have different properties (e.g., resistance to tearing, ease of being cut, etc.) and thus respond differently to actions taken by surgical instruments. Therefore, it may be desirable for a surgical instrument to take different actions even when the same measurement for a particular parameter is sensed. As one example, the optimal manner in which to control a surgical stapler in response to the surgical stapler sensing an unexpectedly high force to close its end effector will vary depending upon whether the tissue type is susceptible or resistant to tearing. For tissues that are susceptible to tearing, such as lung tissue, the surgical instrument's control algorithm would optimally ramp down the motor in response to an unexpectedly high force to close to avoid tearing the tissue, e.g., change a variable parameter controlling motor speed or torque so the motor is slower. For tissues that are resistant to tearing, such as stomach tissue, the instrument's algorithm would optimally ramp up the motor in response to an unexpectedly high force to close to ensure that the end effector is clamped properly on the tissue, e.g., change a variable parameter controlling motor speed or torque so the motor is faster. Without knowing whether lung or stomach tissue has been clamped, the algorithm may be sub-optimally changed or not changed at all.

A surgical hub can be configured to derive information about a surgical procedure being performed based on data received from various data sources and then control modular devices accordingly. In other words, the surgical hub can be configured to infer information about the surgical procedure from received data and then control the modular devices operably coupled to the surgical hub based upon the inferred context of the surgical procedure. Modular devices can include any surgical device that is controllable by a situational awareness system, such as visualization system devices (e.g., a camera, a display screen, etc.), smart surgical instruments (e.g., an ultrasonic surgical instrument, an electrosurgical instrument, a surgical stapler, smoke evacuators, scopes, etc.). A modular device can include sensor(s)s configured to detect parameters associated with a patient with which the device is being used and/or associated with the modular device itself.

The contextual information derived or inferred from the received data can include, for example, a type of surgical procedure being performed, a particular step of the surgical procedure that the surgeon (or other medical practitioner) is performing, a type of tissue being operated on, or a body cavity that is the subject of the surgical procedure. The situational awareness system of the surgical hub can be configured to derive the contextual information from the data received from the data sources in a variety of different ways. In an exemplary embodiment, the contextual information received by the situational awareness system of the surgical hub is associated with a particular control adjustment or set of control adjustments for one or more modular devices. The control adjustments each correspond to a variable parameter. In one example, the situational awareness system includes a pattern recognition system, or machine learning system (e.g., an artificial neural network), that has been trained on training data to correlate various inputs (e.g., data from databases, patient monitoring devices, and/or modular devices) to corresponding contextual information regarding a surgical procedure. In other words, a machine learning system can be trained to accurately derive contextual information regarding a surgical procedure from the provided inputs. In another example, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling at least one modular device. In another example, the situational awareness system includes a further machine learning system, lookup table, or other such system, which generates or retrieves one or more control adjustments for one or more modular devices when provided the contextual information as input.

A surgical hub including a situational awareness system may provide any number of benefits for a surgical system. One benefit includes improving the interpretation of sensed and collected data, which would in turn improve the processing accuracy and/or the usage of the data during the course of a surgical procedure. Another benefit is that the situational awareness system for the surgical hub may improve surgical procedure outcomes by allowing for adjustment of surgical instruments (and other modular devices) for the particular context of each surgical procedure (such as adjusting to different tissue types) and validating actions during a surgical procedure. Yet another benefit is that the situational awareness system may improve surgeon's and/or other medical practitioners' efficiency in performing surgical procedures by automatically suggesting next steps, providing data, and adjusting displays and other modular devices in the surgical theater according to the specific context of the procedure. Another benefit includes proactively and automatically controlling modular devices according to the particular step of the surgical procedure that is being performed to reduce the number of times that medical practitioners are required to interact with or control the surgical system during the course of a surgical procedure, such as by a situationally aware surgical hub proactively activating a generator to which an RF electrosurgical instrument is connected if it determines that a subsequent step of the procedure requires the use of the instrument. Proactively activating the energy source allows the instrument to be ready for use a soon as the preceding step of the procedure is completed.

For example, a situationally aware surgical hub can be configured to determine what type of tissue is being operated on. Therefore, when an unexpectedly high force to close a surgical instrument's end effector is detected, the situationally aware surgical hub can be configured to correctly ramp up or ramp down a motor of the surgical instrument for the type of tissue, e.g., by changing or causing change of at least one variable parameter of an algorithm for the surgical instrument regarding motor speed or torque.

For another example, a type of tissue being operated can affect adjustments that are made to compression rate and load thresholds of a surgical stapler for a particular tissue gap measurement. A situationally aware surgical hub can be configured to infer whether a surgical procedure being performed is a thoracic or an abdominal procedure, allowing the surgical hub to determine whether the tissue clamped by an end effector of the surgical stapler is lung tissue (for a thoracic procedure) or stomach tissue (for an abdominal procedure). The surgical hub can then be configured to cause adjustment of the compression rate and load thresholds of the surgical stapler appropriately for the type of tissue, e.g., by changing or causing change of at least one variable parameter of an algorithm for the surgical stapler regarding compression rate and load threshold.

As yet another example, a type of body cavity being operated in during an insufflation procedure can affect the function of a smoke evacuator. A situationally aware surgical hub can be configured to determine whether the surgical site is under pressure (by determining that the surgical procedure is utilizing insufflation) and determine the procedure type. As a procedure type is generally performed in a specific body cavity, the surgical hub can be configured to control a motor rate of the smoke evacuator appropriately for the body cavity being operated in, e.g., by changing or causing change of at least one variable parameter of an algorithm for the smoke evacuator regarding motor rate. Thus, a situationally aware surgical hub may provide a consistent amount of smoke evacuation for both thoracic and abdominal procedures.

As yet another example, a type of procedure being performed can affect the optimal energy level for an ultrasonic surgical instrument or radio frequency (RF) electrosurgical instrument to operate at. Arthroscopic procedures, for example, require higher energy levels because an end effector of the ultrasonic surgical instrument or RF electrosurgical instrument is immersed in fluid. A situationally aware surgical hub can be configured to determine whether the surgical procedure is an arthroscopic procedure. The surgical hub can be configured to adjust an RF power level or an ultrasonic amplitude of the generator (e.g., adjust energy level) to compensate for the fluid filled environment, e.g., by changing or causing change of at least one variable parameter of an algorithm for the instrument and/or a generator regarding energy level. Relatedly, a type of tissue being operated on can affect the optimal energy level for an ultrasonic surgical instrument or RF electrosurgical instrument to operate at. A situationally aware surgical hub can be configured to determine what type of surgical procedure is being performed and then customize the energy level for the ultrasonic surgical instrument or RF electrosurgical instrument, respectively, according to the expected tissue profile for the surgical procedure, e.g., by changing or causing change of at least one variable parameter of an algorithm for the instrument and/or a generator regarding energy level. Furthermore, a situationally aware surgical hub can be configured to adjust the energy level for the ultrasonic surgical instrument or RF electrosurgical instrument throughout the course of a surgical procedure, rather than just on a procedure-by-procedure basis. A situationally aware surgical hub can be configured to determine what step of the surgical procedure is being performed or will subsequently be performed and then update the control algorithm(s) for the generator and/or ultrasonic surgical instrument or RF electrosurgical instrument to set the energy level at a value appropriate for the expected tissue type according to the surgical procedure step.

As another example, a situationally aware surgical hub can be configured to determine whether the current or subsequent step of a surgical procedure requires a different view or degree of magnification on a display according to feature(s) at the surgical site that the surgeon and/or other medical practitioner is expected to need to view. The surgical hub can be configured to proactively change the displayed view (supplied by, e.g., an imaging device for a visualization system) accordingly so that the display automatically adjusts throughout the surgical procedure.

As yet another example, a situationally aware surgical hub can be configured to determine which step of a surgical procedure is being performed or will subsequently be performed and whether particular data or comparisons between data will be required for that step of the surgical procedure. The surgical hub can be configured to automatically call up data screens based upon the step of the surgical procedure being performed, without waiting for the surgeon or other medical practitioner to ask for the particular information.

As another example, a situationally aware surgical hub can be configured to determine whether a surgeon and/or other medical practitioner is making an error or otherwise deviating from an expected course of action during the course of a surgical procedure, e.g., as provided in a preoperative surgical plan. For example, the surgical hub can be configured to determine a type of surgical procedure being performed, retrieve a corresponding list of steps or order of equipment usage (e.g., from a memory), and then compare the steps being performed or the equipment being used during the course of the surgical procedure to the expected steps or equipment for the type of surgical procedure that the surgical hub determined is being performed. The surgical hub can be configured to provide an alert (visual, audible, and/or tactile) indicating that an unexpected action is being performed or an unexpected device is being utilized at the particular step in the surgical procedure.

In certain instances, operation of a robotic surgical system, such as any of the various robotic surgical systems described herein, can be controlled by the surgical hub based on its situational awareness and/or feedback from the components thereof and/or based on information from a cloud (e.g., the cloud 713 of FIG. 18).

Embodiments of situational awareness systems and using situational awareness systems during performance of a surgical procedure are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019.

Integrated Anchoring Elements

In certain embodiments, surgical anchoring systems that are configured for endoluminal access and enable non-traumatic retraction or manipulation of the surgical site to improve access thereto (e.g., visual and/or operational purposes). Unlike conventional systems (e.g., systems that use laparoscopically arranged instruments, such as graspers, to grasp the fragile exterior tissue surfaces of an organ), the present surgical anchoring systems are designed to manipulate the organ using anchor members, which not only have a larger surface area than conventional graspers, but are also configured to apply a manipulation force to an inner tissue layer of an organ, which is typically tougher and less fragile than the organ's outer tissue layer(s). This inner manipulation force can increase the mobilization of an organ at a treatment site to thereby improve access and movement (e.g., for dissection and resection) without damaging the exterior tissue layer of an organ or reducing blood flow to the treatment site. The organ can include multiple natural body lumens (e.g., bronchioles of a lung), whereas in other embodiments, the organ includes a single natural body lumen (e.g., a colon).

In one exemplary embodiment, the surgical anchor systems can include a surgical instrument configured for endoluminal access (e.g., an endoscope) that includes an outer sleeve defining a working channel therethrough and at least one channel arm configured to extend through the working channel. The at least one channel arm includes at least one anchor member coupled to the at least one channel arm and configured to move between expanded and unexpanded states, and at least one control actuator extending along the at least one channel arm and operatively coupled to the at least one anchor member. The at least one control actuator is also operatively coupled to a drive system that is configured to control motion of the at least one channel arm. The at least one anchor member can be configured to be at least partially disposed within a natural body lumen such that, when in the expanded state, the at least one anchor member can contact an inner surface of the natural body lumen and therefore anchor the at least one channel arm to the natural body lumen. As a result, the motion of the channel arm can selectively manipulate the natural body lumen anchored thereto (e.g., internally manipulate) and consequently, the organ which is associated with the natural body lumen.

In another exemplary embodiment, the surgical anchoring systems can include a surgical instrument configured for endoluminal access (e.g., an endoscope) that includes dual coupled deployable fixation elements. The dual coupled deployable fixation elements are configured to interact with both a fixed anatomical location and a moveable anatomical location to manipulate and reposition an organ. The surgical instrument can include a first deployable fixation element that is deployed at a natural body orifice of the organ, which acts as a fixed anatomical location. The surgical instrument can include a second deployable fixation element that is deployed at a moveable anatomical location spaced apart from the fixed anatomical location. The surgical instrument can be configured to manipulate and reposition the organ to improve access and visibility from the opposite side of the organ wall. Due to the coupling of the first deployable fixation element to a fixed anatomical location, the forces and restraints of the fixed anatomical location can be communicated to the second first deployable fixation element to allow for induced lateral forces and movements to the organ.

The term "expanded" is intended to mean that the anchor member(s) has/have increased in size in a desired amount through mechanical means or fluid pressure. These terms are not intended to mean that the anchor member(s) is/are necessarily entirely or 100% filled with a fluid when the anchor member(s) are "expanded" (however, such embodiments are within the scope of the term "filled"). Similarly, the term "unexpanded" does not necessarily mean that the anchor member(s) is/are entirely empty or at 0 pressure. There may be some fluid and the anchor member(s) may have a non-zero pressure in an "unexpanded" state. An "uninflated" anchor member(s) is/are intended to mean that the anchor member(s) is/are mechanically collapsed to a smaller size than the expanded size, or does/do not include fluid in an amount or at a pressure that would be desired after the anchor member(s) is/are filled.

An exemplary surgical anchoring system can include a variety of features as described herein and illustrated in the drawings. However, a person skilled in the art will appreciate that the surgical anchoring systems can include only some of these features and/or it can include a variety of other features known in the art. The surgical anchoring systems described herein are merely intended to represent certain exemplary embodiments. Moreover, while the surgical anchoring systems are shown and described in connection with a lung and a colon, a person skilled in the art will appreciate that these surgical anchoring systems can be used in connection with any other suitable natural body lumens or organs.

A lung resection (e.g., a lobectomy) is a surgical procedure in which all or part (e.g., one or more lobes) of the lung is removed. The purpose of performing a lung resection is to treat a damaged or diseased lung as a result of, for example, lung cancer, emphysema, or bronchiectasis. During a lung resection, the lung or lungs are first deflated, and thereafter one or more incisions are made on the patient's side between the ribs to reach the lungs laparoscopically. Instruments, such as graspers and a laparoscope, are inserted through the incision. Once the infected or damaged area of the lung is identified, the area is dissected from the lung and removed from the one or more incisions. The dissected area and the one or more incisions can be closed, for example, with a surgical stapler or stiches.

Since the lung is deflated during surgery, the lung, or certain portions thereof, may need to be mobilized to allow the instruments to reach the surgical site. This mobilization can be carried out by grasping the outer tissue layer of the lung with graspers and applying a force to the lung through the graspers. However, the pleura and parenchyma of the lung are very fragile and therefore can be easily ripped or torn under the applied force. Additionally, during mobilization, the graspers can cut off blood supply to one or more areas of the lung.

Figure 22:
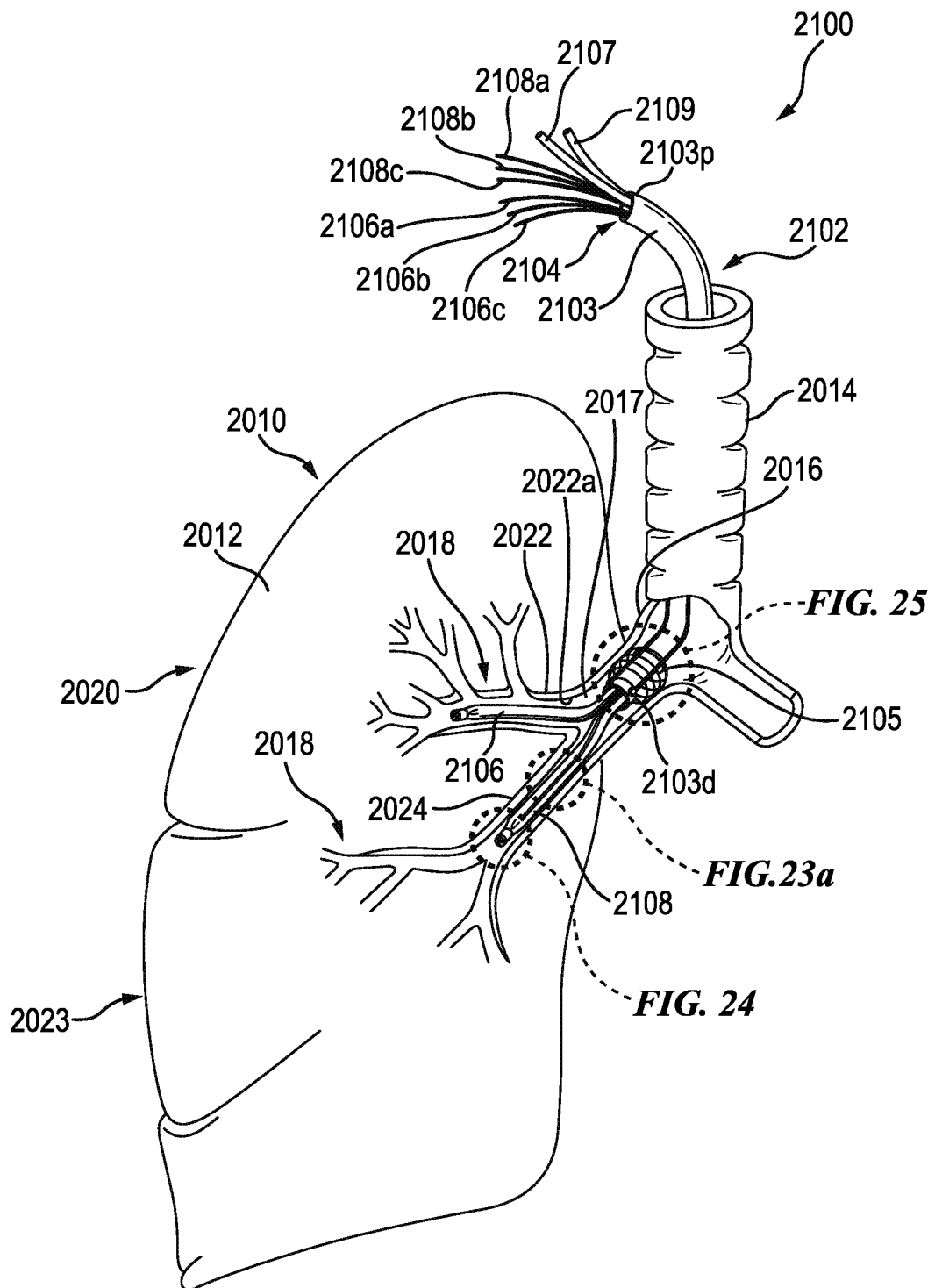
FIG. 22 is a schematic view of one embodiment of a surgical anchoring system having an outer sleeve and channel arms that extend through the outer sleeve in which the channel arms include respective anchor members, showing the surgical anchoring system inserted through a throat and into a lung with a portion the outer sleeve passing through the throat and into the lung and the channel arms extending through the outer sleeve and into respective portions of the lung with the respective anchor members in an unexpanded state.

FIG. 22 illustrates an exemplary embodiment of a surgical anchoring system 2100 that is configured for endoluminal access into a lung 2010. As will be described in more detail below, the surgical anchoring system 2100 is used to manipulate a lung 2010 through contact with a natural body lumen (e.g., first bronchiole 2022) within the lung 2010. For purposes of simplicity, certain components of the surgical anchoring system 2100 and the lung 2010 are not illustrated.

As shown, the lung 2010 includes an outer tissue surface 2012, a trachea 2014, a right bronchus 2016, and bronchioles 2018. The trachea 2014, right bronchus 2016, and the bronchioles 2018 are in fluid communication with each other. Additionally, the lung 2010 includes an upper lobe 2020, which includes first bronchiole 2022, and a middle lobe 2023, which includes second bronchiole 2024. As illustrated in FIG. 22, the lung 2010 is in an inflated state while the surgical anchoring system 2100 is initially inserted into the lung 2010. When operating in the thoracic cavity, the lung 2010 is collapsed to provide sufficient working space between the rib cage and the lungs such that laparoscopically arranged instruments can access and manipulate the lung 2010. In use, as described in more detail below, the surgical anchoring system 2100 can manipulate (e.g., mobilize) a portion of the lung 2010.

The surgical anchoring system 2100 includes a surgical instrument 2102 configured for endoluminal access through the trachea 2014 and into the lung 2010. The surgical instrument can have a variety of configurations. For example, in this illustrated embodiment, the surgical instrument 2102 includes an outer sleeve 2103 and first and second channel arms 2106, 2108. While two channel arms 2106, 2108 are illustrated, in other embodiments, the surgical instrument can include a single channel arm or more than two channel arms. The outer sleeve 2103 is configured to be inserted through a patient's mouth (not shown) and down the trachea 2014. The outer sleeve 2103 includes a working channel 2104 that is configured to allow the first and second channel arms 2106, 2108 to be inserted through the outer sleeve 2103 and access the lung 2010. As such, the first and second channel arms 2106, 2108 can be configured to move independently of the working channel 2014.

Figure 23A:
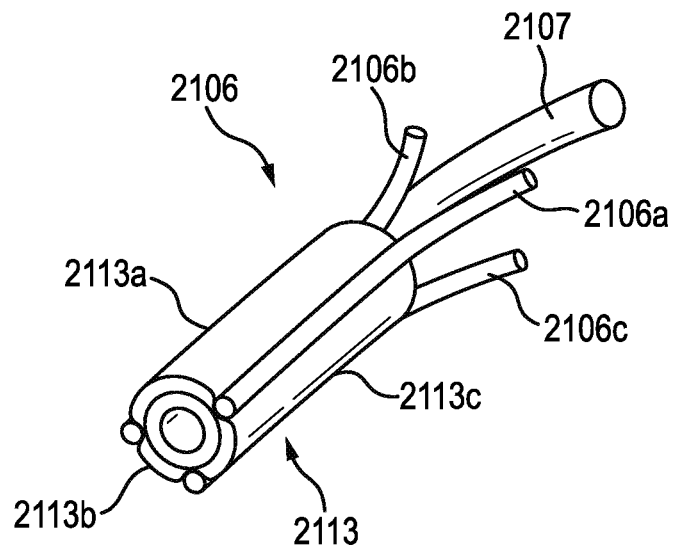
FIG. 23A is a magnified view of a portion of one of the channel arms of the surgical anchoring system of FIG. 22 with the lung removed and a portion of the respective anchor members.
Figure 23B:
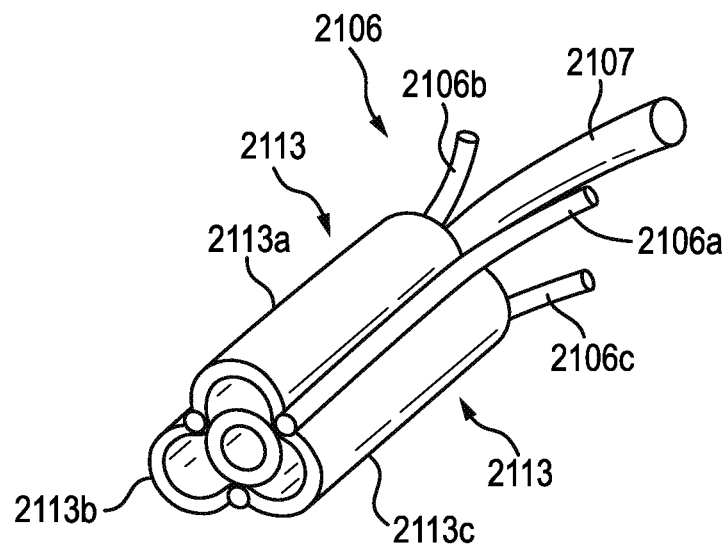
FIG. 23B is the channel arm of FIG. 23A, showing the anchor members in an expanded state.
Figure 24:
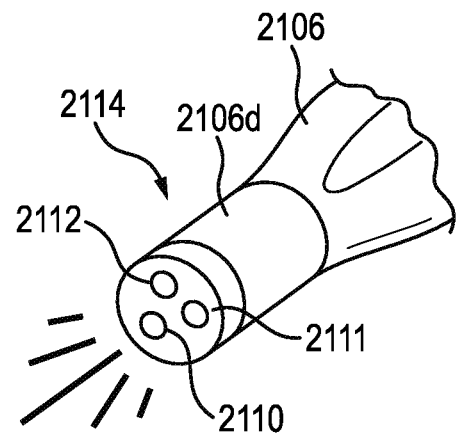
FIG. 24 is a magnified view of a distal end of a channel arm of the surgical anchoring system of FIG. 22 with the lung removed.

Each of the first and second channel arms 2106, 2108 can include at least one anchor member coupled to the at least one channel arm and configured to move between expanded and unexpanded states. When in the expanded state, the at least one anchor member is configured to be at least partially disposed within a second natural body lumen, the second natural body lumen being in communication with a first natural body lumen that the outer sleeve is partially disposed within. In this illustrated embodiment, a first anchor member 2113 (see FIG. 23A, FIG. 23B, and FIG. 24) is coupled to first channel arm 2106 and a second anchor member 2115 (see FIG. 26) is coupled to the second channel arm 2108 Further, as shown in FIG. 22 and FIG. 23, the first natural body lumen is the right bronchus 2016 and the second natural body lumen is the first bronchiole 2022.

Further, each of the first and second channel arms 2106, 2108 also include control actuators and a fluid tube which extend along the length of the channel arms and further extends from the proximal end 2103p of the outer sleeve 2103. As shown in FIG. 22, the first channel arm 2106 includes three control actuators 2106a, 2106b, 2106c and a first fluid tube 2107. The second channel arm 2108 includes three control actuators 2108a, 2108b, 2108c and a second fluid tube 2109. As described in more detail below, the control actuators of each control arm are configured to allow for manipulation of the lung 2010, and the fluid tubes 2107, 2109 are configured to provide a fluid to the first and second anchor members 2113, 2115 coupled to the first and second channel arms 2106, 2108.

Figure 26:
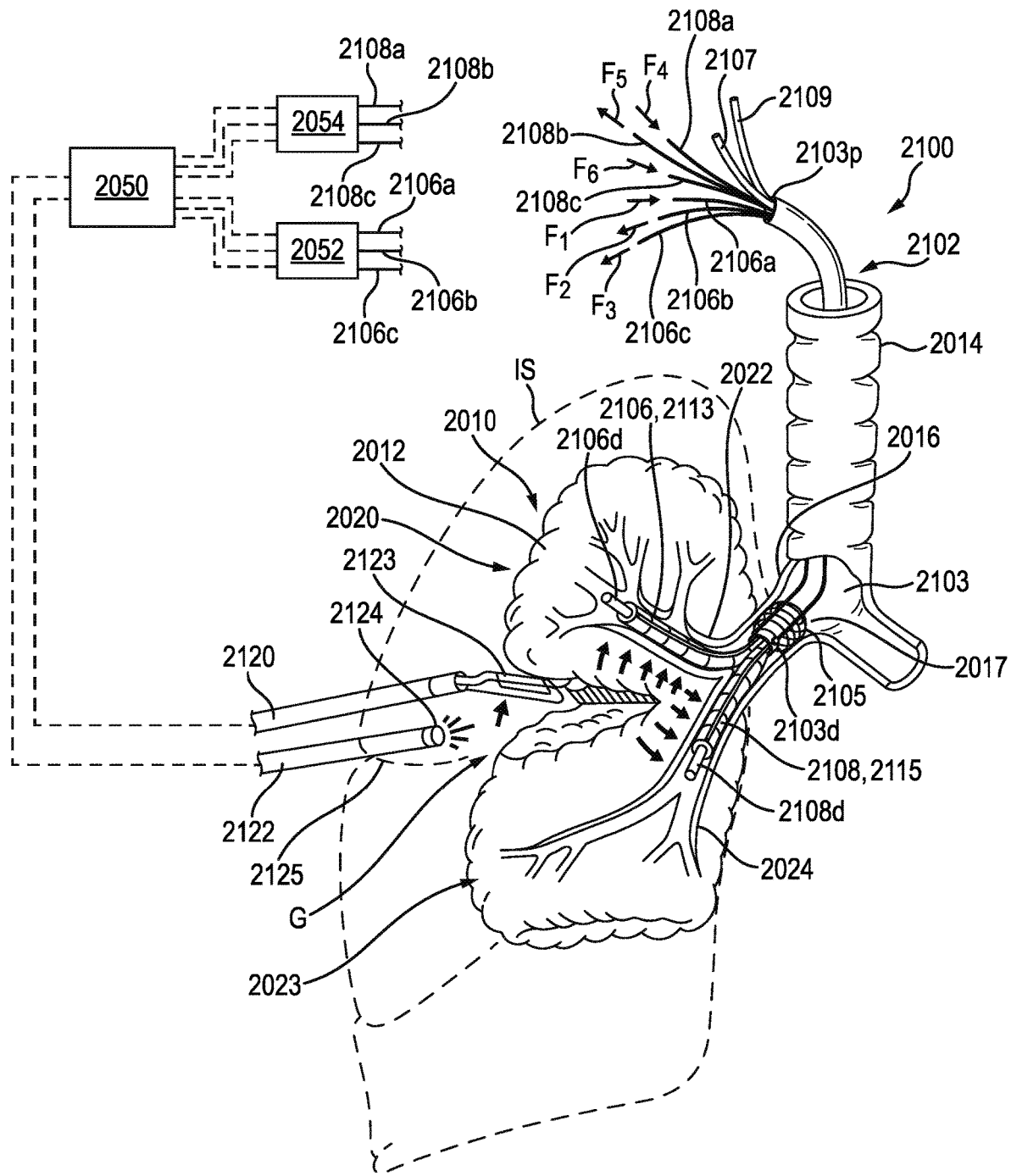
FIG. 26 is a schematic view of the surgical anchoring system of FIG. 22, showing the anchor members in an expanded state while manipulating the lung from an intraluminal space and from an extraluminal space using laparoscopically inserted instruments.

In use, as shown in FIG. 22, the outer sleeve 2103 is passed into the trachea 2014 through a patient's mouth (not shown). With the outer sleeve in position, the anchor member 2105 moves to an expanded state, where the anchor member 2105 at least partially contacts an internal surface 2017 of the right bronchus 2016. By contacting the inner surface 2017, the outer sleeve 2103 is fixated to the trachea 2014 and the right bronchus 2016. The first channel arm 2106 is passed into the lung 2010 through the right bronchus 2016 via the outer sleeve 2105, and into the first bronchiole 2022 of the upper lobe 2020, and the second channel arm 2108 is passed into the lung 2010 through the right bronchus 2016, and into the second bronchiole 2024 of the middle lobe 2023. Once the first and second channel arms 2106, 2108 are properly positioned within the first and second bronchi 2022, 2024, respectively, the first and second anchor member 2113, 2115 can be expanded to at least partially contact the inner surface of the bronchioles 2022, 2024. For sake of simplicity, the following description is with respect to the first anchor member 2113. A person skilled in the art will understand, however, that the following discussion is also appliactuator to the second anchor member 2115, which as shown in FIG. 26 is structurally similar to that of the first anchor member 2113. A detailed partial view of the first anchor member 2113 is illustrated in an unexpanded state (FIG. 23A) and in an expanded state (FIG. 23B).

As shown, the first anchor member 2113 is arranged distal to the distal end 2103d of the outer sleeve 2103 such that the first anchor member 2113 can be positioned within the first bronchiole 2022. The first anchor member 2113 is configured to move between an unexpanded state (FIG. 23A) and an expanded state (FIG. 23B). The first anchor member 2113 can have a variety of configurations. For example, in some embodiments, the first anchor member can be an inflatable balloon, whereas in other embodiments, the first anchor member can be a mechanically expandable stent.

As illustrated in FIG. 23A and FIG. 23B, the first anchor member 2113 includes three bladders 2113a, 2113b, 2113c arranged about an outer surface of the first fluid tube 2107. The bladders 2113a, 2113b, 2113c are separated from one another (e.g., by control actuators 2106a, 2106b, and 2106c arranged between the bladders 2113a, 2113b, 2113c). The bladders 2113a, 2113b, 2113c are expanded by the ingress of fluid through the first fluid tube 2107, which is in fluid communication with each bladder 2113a, 2113b, 2113c, and unexpanded through the egress of fluid from the bladders 2113a, 2113b, 2113c through the first fluid tube 2107. In some embodiments, each bladder 2113a, 2113b, 2113c extends along the length of the first channel arm 2106. Alternatively, in certain embodiments, the bladders 2113a, 2113b, 2113c are arranged along only a portion of the length of the first channel arm 2106.

Figure 25:
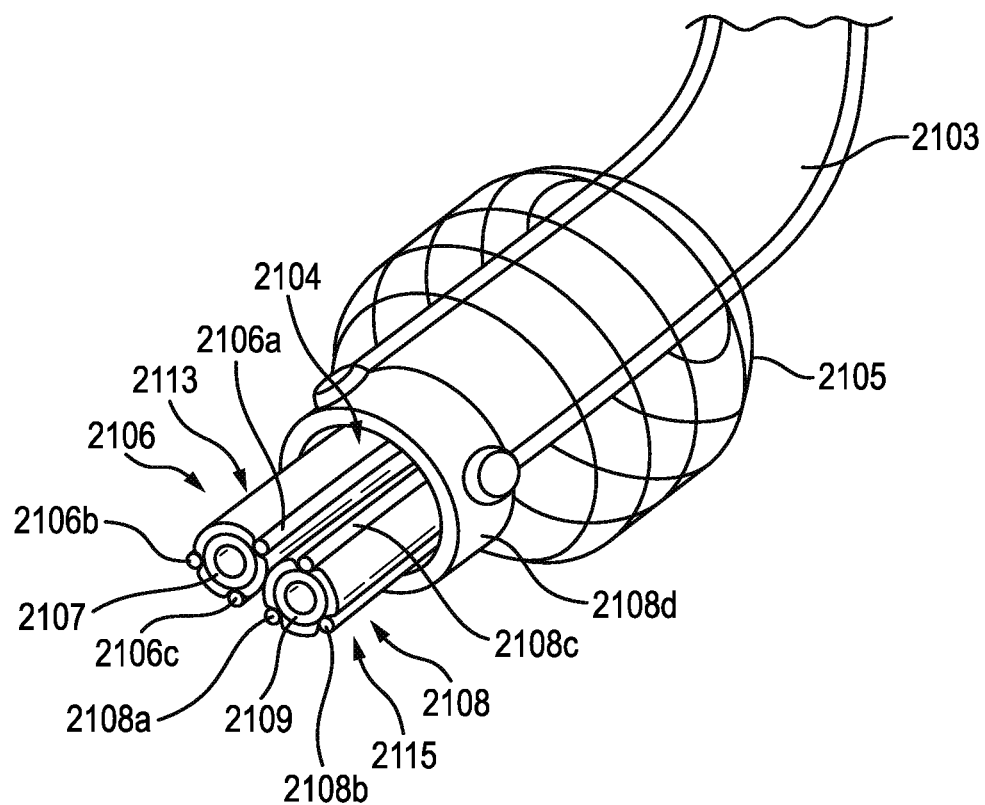
FIG. 25 is a magnified view of a portion of the surgical anchoring system of FIG. 22 with the lung removed.

Alternatively, or in addition, at least one of the first and second channel arms 2106, 2108 can include an optical sensor. By way of example, FIG. 25 illustrates a partial view of a distal end 2106d of the first channel arm 2106. As shown, the distal end 2106d of the channel arm 2106 can include a scope 2114 with an optical sensor 2110 arranged thereon. The optical sensor 2110 can be configured to allow a user to determine the location of the first channel arm 2106 within the lung 2010 and to help the user position the distal tip 2106d into the desired bronchiole, such as first bronchiole 2022. Views from the optical sensor 2110 can be provided in real time to a user (e.g., a surgeon), such as on a display (e.g., a monitor, a computer tablet screen, etc.). The scope 2114 can also include a light 2111 and a working channel and/or a fluid channel 2112 that is configured to allow for the insertion and extraction of a surgical instrument and/or for the ingress and egress of a surgical instrument or fluid to the treatment site within the lung 2010. A person skilled in the art will appreciate that the second channel arm can alternatively or in addition include a scope that is similar to scope 2114 in FIG. 25.

In some embodiments, the outer sleeve 2103 can include additional elements. For example, as shown in FIG. 22, and in more detail in FIG. 25, the outer sleeve 2103 includes an anchor member 2105 arranged proximate to a distal end 2103*d* of the outer sleeve 2103. In other embodiments, the anchor member 2105 can be arranged at the distal end 2103*d*.

A detailed partial view of the distal end 2130*d* of the outer sleeve 2103 and the channel arms 2106, 2108 is illustrated in FIG. 25. As shown, the channel arms 2106, 2108 extend outward from the distal end 2103*d* of the outer sleeve 2103. In some embodiments, the channel arms 2106, 2108 can move relative to each other, and the outer sleeve 2103. As stated above, an anchor member 2105 is arranged on the outer sleeve 2103. The anchor member 2105 is configured to move between expanded and unexpanded states. In an expanded state, the anchor member 2105 is configured to at least partially contact an internal surface 2017 of the right bronchus 2016. By contacting the inner surface 2017, the outer sleeve 2103 can be fixated to the trachea 2014 and the right bronchus 2016. This fixation can allow for a manipulation force (e.g., twisting force) to be applied to the lung 2010 through the channel arms 2106, 2108. As a result, the lung 2010 can be mobilized relative to the trachea 2014 and the right bronchus 2016.

Increasing of the distribution of forces applied to the lung 2010 and reducing the tissue interaction pressure can be achieved by increasing the internal surface area in which the anchor members interact with. The anchor elements are configured to expand to the internal diameter of the bronchus. By spreading to the full internal diameter, and having the channel arms extended from the distal end of the outer sleeve, the surgical anchoring system acts as a skeleton system within the lung. By moving the outer sleeve and/or channel arms, the bronchioles or bronchus are moved, thereby moving the lung. Since the outer sleeve and anchoring elements are spread out over a large area, the forces applied to the lung are not concentrated, compared to manipulating the lung with small graspers from the laparoscopic side. Additionally the cartridge rings and wall strength of the bronchus make it more ideal for instrument interaction for gross lung movement or repositioning without collateral damage to the surrounding softer and more fragile pleura and parenchyma.

In an example embodiment, bifurcating and extending a portion of the surgical anchor system down two separate distal branches from the outer sleeve 2103 can be used to better hold a larger, more triangulated area of the lung 2010. Additionally, a portion of the outer sleeve 2103 can expand in addition to the channel arms 2106, 2108 extending from the working channel. Additionally the outer sleeve 2103 can include radial expandable elements that would provide additional contact area within the trachea 2014 that would allow the surgical anchoring system 2100 to completely control both the flexion, but also twist, expansion, and/or compression of the lung 2010. This would enable the surgical anchoring system 2100 to guide the lung to the correct location and position within the thoracic cavity, but also to control the shape of the lung so that a dissection and/or transection could be done from the thoracic cavity side.

The anchor member 2105 can have a variety of configurations. For example, in some embodiments, the anchor member 2105 can be an inflatable anchoring balloon. In embodiments where the anchor member 2105 is an inflatable anchoring balloon, the anchor member 2105 is configured to expand or collapse through the ingress or egress of a fluid passing through a fluid tube (not shown) in fluid communication with the anchor member 2105. The fluid tube extends along the length of the outer sleeve 2103 and can be controlled outside of a patient's body. In other embodiments, the anchor member 2105 can be a mechanically expandable stent.

With the channel arms 2106, 2108 properly arranged within the bronchioles 2022, 2024, the lung 2010 is collapsed. This results in the lung considerably shrinking in size relative to its size in its inflated state. The lung 2010 as illustrated in FIG. 26 is in a collapsed state, with the previous inflated state being represented as a dashed-line border IS. In use, when in the expanded state as shown in FIG. 26, the first anchor member 2113 is configured to at least partially contact the internal surface 2022*a* of the first bronchiole 2022. This contact fixates the first anchor member 2113 to the first bronchiole 2022, and thereby the lung 2010. The first anchor member 2113 can alternate between its unexpanded and expanded states by passing fluid into or removing fluid from the bladders 2113*a*, 2113*b*, 2113*c* through the fluid tube 2107 that passes through the length of the channel arm 2106. The fluid passed into or out of the bladders 2113*a*, 2113*b*, 2113*c* can be any suitable fluid (e.g., saline, carbon dioxide gas, and the like). A proximal-most end (not shown) of the fluid tube 2107 is configured to couple to fluid system that can be used to control the ingress or egress of fluid into the bladders 2113*a*, 2113*b*, 2113*c*. The fluid system can include a pump and a fluid reservoir. The pump creates a pressure which pushes the fluid into the bladders 2113*a*, 2113*b*, 2113*c*, to expand the bladders 2113*a*, 2113*b*, 2113*c*, and creates a suction that draws the fluid from the bladders 2113*a*, 2113*b*, 2113*c* in order to collapse the bladders 2113*a*, 2113*b*, 2113*c*. A person skilled in the art will appreciate that the second anchor member 2115 can be moved between an expanded and unexpanded state within the second bronchiole 2024 in a similar way as discussed above with respect to the first anchor member 2113.

Further, in use other surgical instruments 2120, 2122 can be introduced laparoscopically within the thoracic cavity in order to visualize and/or operate on the lung 2010 from the extraluminal space. The surgical instruments 2120, 2122 can include a variety of surgical tools, such as graspers 2123, optical sensors 2124, and/or electrosurgical tool 2125. In an exemplary embodiment, where the surgical instrument 2122 is or includes an optical sensor 2124, a user (e.g., a surgeon) can visually inspect the collapsed lung 2010 (FIG. 26) to perform an incision on the lung 2010 using the graspers 2123 or the electrosurgical tool 2125.

Moreover, in use, with the anchor members 2113, 2115 in expanded states, manipulation forces can be applied to the lung 2010 through the control actuators 2106*a*, 2106*b*, 2106*c*, 2108*a*, 2108*b*, 2108*c*. In some embodiments, the surgical anchoring system 2100 includes a controller 2050 that is configured to coordinate a motion of the channel arms 2106, 2108 within the bronchioles 2022, 2024 and a motion of at least one instrument 2120, 2122 outside of the lung 2010 to prevent tearing of the bronchioles 2022, 2024 or the exterior tissue surface 2012 of the lung 2010. The controller 2050 can be communicatively coupled to the robotic arms (not shown) which the instruments 2120, 2122 are connected to, and to actuators 2052, 2054. The actuator 2052 is configured to apply the manipulation forces $F_1$, $F_2$, $F_3$ to control actuators 2106*a*, 2106*b*, 2106*c*, and the actuator 2054 is configured to apply the manipulation forces $F_4$, $F_5$, $F_6$ to control actuators 2108*a*, 2108*b*, 2108*c*.

In use, manipulation force $F_1$ is applied to control actuator 2106*a*, manipulation force $F_2$ is applied to control actuator 2106*b*, manipulation force $F_3$ is applied to control actuator 2106*c*, manipulation force $F_4$ is applied to control actuator 2108*a*, manipulation force $F_5$ is applied to control actuator 2108*b*, and manipulation force $F_6$ is applied to control actuator 2108*c*. With the manipulation forces applied to the lung 2010, the horizontal fissure between the upper lobe 2020 and the middle lobe 2023 can be widened to form a gap G. The gap G allows for access to the lung 2010 so the horizontal fissure can be further expanded. The manipulation forces cause the channel arms 2106, 2108 to move in opposite directions, causing the upper lobe 2020 to move away from the middle lobe 2023. The anchor member 2115, in an expanded state within the right bronchus 2016, prevents unintended twisting of the lung 2010 while the manipulation forces are applied to the lung 2010. As such, the lung 2010 can be manipulated in a single plane in order to increase the gap G in an efficient manner. With the manipulation complete, the anchor members 2113, 2115 are deflated and removed from the bronchioles 2022, 2024 and out through the outer sleeve 2103. The anchor member 2105 is also deflated, allowing the outer sleeve 2103 to also be removed from the trachea 2014, causing little to no damage to the trachea 2014 or lung 2020 when compared to conventional procedures using graspers only to mobilize the lung 2020.

If a surgeon has at least one channel arm 2106, 2108 deployed within a bronchiole, and the grasper 2123 arranged on the laparoscopic side of the lung 2010, both the channel arm and the instrument could be driven together to move in the same direction or in opposed directions. Moving both in the same direction would allow for supported movement of the section grasped between them. Moving both in opposite directions would create tissue tension which would make it easier for dissection or tissue plane separation. Moving both in the same direction could also be coordinated in a coupled motion or an antagonistic manner where either the channel arm or instrument was the driver coupling, and the other would be the follower while providing a defined sustainable force between the channel arm and instrument. In some embodiments, other forms of synchronized motion can include a maximum threshold for coupled forces, position control, and/or velocity matching.

Figure 27:
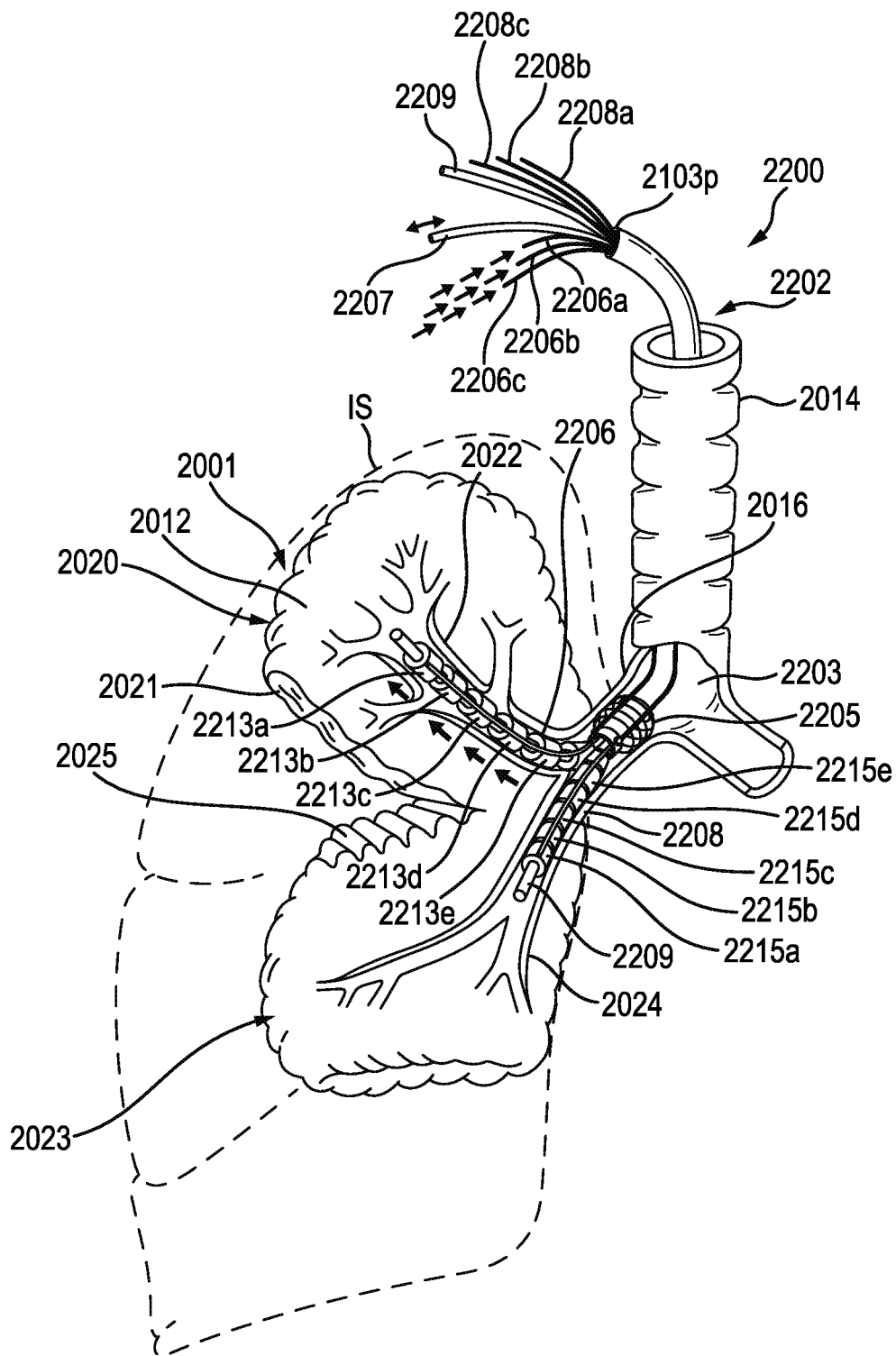
FIG. 27 is a schematic view of another embodiment of a surgical anchoring system, showing the surgical anchoring system inserted through the throat and into a lung.

FIG. 27 illustrates a schematic view of a surgical anchoring system 2200 arranged within a collapsed lung 2201. Aside from the differences described in detail below, the surgical anchoring system 2200 and the collapsed lung 2201 can be similar to the surgical anchoring system 2100 in FIG. 22 and FIG. 26 and the collapsed lung 2010 in FIG. 26 and therefore common features are not described in detail herein.

The surgical anchoring system 2200 includes a surgical instrument 2202, an outer sleeve 2203, an anchor member 2205 coupled to the outer sleeve 2203, a first channel arm 2206, and a second channel arm 2208. The first channel arm 2206 includes control actuators 2206*a*, 2206*b*, 2206*c* extending along the length of the channel arm 2206 and configured to provide a manipulation force to the lung 2201 (e.g., through the first bronchiole 2022). The second channel arm 2208 includes control actuators 2208*a*, 2208*b*, 2208*c* extending along the length of the second channel arm 2208 and configured to provide a manipulation force to the lung 2201 (e.g., through the second bronchiole 2024).

As shown in FIG. 27, the first channel arm 2206 includes anchor members 2213*a*, 2213*b*, 2213*c*, 2213*d*, 2213*e* that are arranged on a clutch actuator 2207 that extends through the first channel arm 2206. Each of the anchor members 2213*a*, 2213*b*, 2213*c*, 2213*d*, 2213*e* are configured to move axially along the length of the channel arm 2206. The clutch actuator 2207 is configured to selectively position the anchor members 2213*a*, 2213*b*, 2213*c*, 2213*d*, 2213*e* at an axial position along the length of the first channel arm 2206. Similar to the anchor member 2113, the anchor members 2213*a*, 2213*b*, 2213*c*, 2213*d*, 2213*e* each include inflatable bladders which can be mechanically expanded or filled with a fluid through a fluid channel extending through the length of the clutch actuator 2207.

Additionally, second channel arm 2208 includes anchor members 2215*a*, 2215*b*, 2215*c*, 2215*d*, 2215*e* arranged on a clutch actuator 2209. Each of the anchor members 2215*a*, 2215*b*, 2215*c*, 2215*d*, 2215*e* are configured to move axially along the length of the second channel arm 2208. The clutch actuator 2209 is configured to selectively position the anchor members 2215*a*, 2215*b*, 2215*c*, 2215*d*, 2215*e* at an axial position along the length of the second channel arm 2208. Similar to the anchor member 2115, the anchor members 2215*a*, 2215*b*, 2215*c*, 2215*d*, 2215*e* each include inflatable bladders which can be mechanically expanded or filled with a fluid through a fluid channel extending through the length of the clutch actuator 2209.

In use, the outer sleeve 2203 is inserted and the anchor member 2205 is moved to an expanded state to contact the inner tissue surface 2022*a* of the right bronchus 2016. The first and second channel arms 2206, 2208 are inserted into and arranged within the bronchioles 2022, 2024 prior to the lung 2010 being collapsed. After the lung 2010 is collapsed, the anchor members 2213*a*, 2213*b*, 2213*c*, 2213*d*, 2213*e*, 2215*a*, 2215*b*, 2215*c*, 2215*d*, 2215*e* are moved to an expanded state to contact an inner tissue surface 2022*a* of the bronchioles 2022, 2024.

With the anchor members 2213*a*, 2213*b*, 2213*c*, 2213*d*, 2213*e*, 2215*a*, 2215*b*, 2215*c*, 2215*d*, 2215*e* in an expanded state, the clutch actuators 2207, 2209 can be axially displaced relative to the outer sleeve 2103, pushing the clutch actuators 2207, 2209 further into the first and second bronchioles 2022, 2024. In some embodiments, the anchor members 2213*a*, 2213*b*, 2213*c*, 2213*d*, 2213*e*, 2215*a*, 2215*b*, 2215*c*, 2215*d*, 2215*e* can slide relatively along the clutch actuators 2207, 2209 a prescribed amount before being coupled to the clutch actuators 2207, 2209. This allows for a space to form between each of the anchor members 2213*a*, 2213*b*, 2213*c*, 2213*d*, 2213*e*, 2215*a*, 2215*b*, 2215*c*, 2215*d*, 2215*e*, which pulls the loose tissue surrounding the first and second bronchioles 2022, 2024 taut. As the clutch actuators 2207, 2209 are retracted from the lung 2201, the gap between each of the anchor members 2213*a*, 2213*b*, 2213*c*, 2213*d*, 2213*e*, 2215*a*, 2215*b*, 2215*c*, 2215*d*, 2215*e* is reduced, collapsing the tissue surrounding the first and second bronchioles 2022, 2024.

In addition to manipulating the lung 2201 using the control actuators of the first channel arms 2206, the first clutch actuator 2207 can be used to axially move the anchor members 2213*a*, 2213*b*, 2213*c*, 2213*d*, 2213*e* along a length of the first channel arm 2206. By axially moving the anchor members 2213*a*, 2213*b*, 2213*c*, 2213*d*, 2213*e*, the upper lobe 2020 and first bronchiole 2022 are partially expanded to an inflated state through the mechanical expansion of the anchor members 2213*a*, 2213*b*, 2213*c*, 2213*d*, 2213*e*. As illustrated, the exterior tissue surface 2021 of the upper lobe 2020 at the horizontal fissure is taut due to the axially expansion of the anchor members 2213*a*, 2213*b*, 2213*c*, 2213*d*, 2213*e* when compared to the exterior tissue surface 2025 of the middle lobe 2023, which is bunched up due to the collapsed state of the lung 2010. The axial expansion of the anchor members 2213*a*, 2213*b*, 2213*c*, 2213*d*, 2213*e* also places the upper lobe 2020 in a similar shape to when the lung 2201 is inflated, as shown by the inflated state line IS.

Similarly, in addition to manipulating the lung 2201 using the control actuators of the second channel arm 2208, the second clutch actuator 2209 can be used to axially move the anchor members 2215a, 2215b, 2215c, 2215d, 2215e along a length of the second channel arm 2208. By axially moving the anchor members 2215a, 2215b, 2215c, 2215d, 2215e, the middle lobe 2023 and second bronchiole 2024 can partially expanded, similar the upper lobe 2020. The axial expansion of the anchor members 2215a, 2215b, 2215c, 2215d, 2215e also can place the middle lobe 2023 in a similar shape to when the lung 2201 is inflated, as shown by the inflated state line IS.

In other embodiments, the amount of axial extension by the anchor members can be guided by a user, but have force limits corresponding to the amount of force capable of being exerted between two anchor members. Additionally, there can be a maximum limit on the amount of displacement between two anchor members to prevent over distention of the organ. In certain embodiments, the anchor members themselves can also have load limits by either controlling the maximum expansive force for limiting friction. The anchor members can have integrated sensors that would limit the externally applied forces between the anchor members as they are axially displaced. The force applied radially could be proportionately coupled to the longitudinal forces applied to prevent inadvertent diametric stretch damage even when applying only a small delicate stretching motion. Alternatively or in addition, the surgical anchoring system can be run in a form of load/creep control, allowing for the maintaining of a predefined force, and then automatically continuing to extend proportionate to the creep in the tissue of the organ. This would allow the viscoelastic properties of the tissue of the organ to be used to help the expansion of the organ rather than hinder the expansion.

In certain embodiments, prior to the activation of the axial movement of the anchor members, a structured light scan can be taken of the tissue, providing a 3D surface model of the pre-stretched anatomy of the organ. This image can be stored and overlaid to the stretch condition of the organ, providing visual information on the nature of the organ shape change, providing insights to the unseen branching of the organ below the exterior tissue surface.

As noted above, the present surgical anchoring systems can be configured to manipulate other natural body lumens or organs. For example, as discussed below, the present surgical anchoring systems can be configured to manipulate one or more portions of the colon endoscopically.

Figure 28:
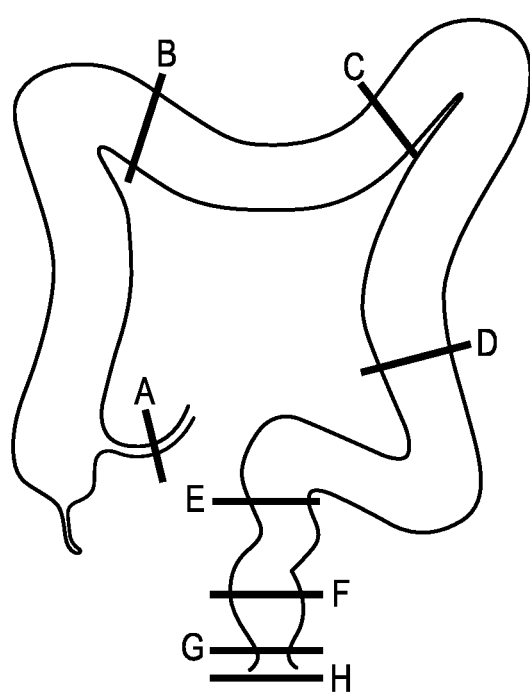
FIG. 28 is a schematic view of a colon.

Surgery is often the primary treatment for early-stage colon cancers. The type of surgery used depends on the stage (extent) of the cancer, its location in the colon, and the goal of the surgery. Some early colon cancers (stage 0 and some early stage I tumors) and most polyps can be removed during a colonoscopy. However, if the cancer has progressed, a local excision or colectomy, a surgical procedure that removes all or part of the colon, may be required. In certain instances, nearby lymph nodes are also removed. A hemicolectomy, or partial colectomy, can be performed if only part of the colon is removed. In a segmental resection of the colon the surgeon removes the diseased part of the colon along with a small segment of non-diseased colon on either side. Usually, about one-fourth to one-third of the colon is removed, depending on the size and location of the cancer. Major resections of the colon are illustrated in FIG. 28, in which (i) A-B is a right hemicolectomy, A-C is an extended right hemicolectomy, B-C is a transverse colectomy, C-E is a left hemicolectomy, D-E is a sigmoid colectomy, D-F is an anterior resection, D-G is a (ultra) low anterior resection, D-H is an abdomino-perineal resection, A-D is a subtotal colectomy, A-E is a total colectomy, and A-H is a total proctocolectomy. Once the resection is complete, the remaining intact sections of colon are then reattached.

During a laparoscopic-assisted colectomy procedure, it is often difficult to obtain an adequate operative field. Often times, dissections are made deep in the pelvis which makes it difficult to obtain adequate visualization of the area. As a result, the lower rectum must be lifted and rotated to gain access to the veins and arteries around both sides of the rectum during mobilization. During manipulation of the lower rectum, bunching of tissue and/or overstretching of tissue can occur. Additionally, a tumor within the rectum can cause adhesions in the surrounding pelvis, and as a result, this can require freeing the rectal stump and mobilizing the mesentery and blood supply before transection and removal of the tumor.

Figure 29:
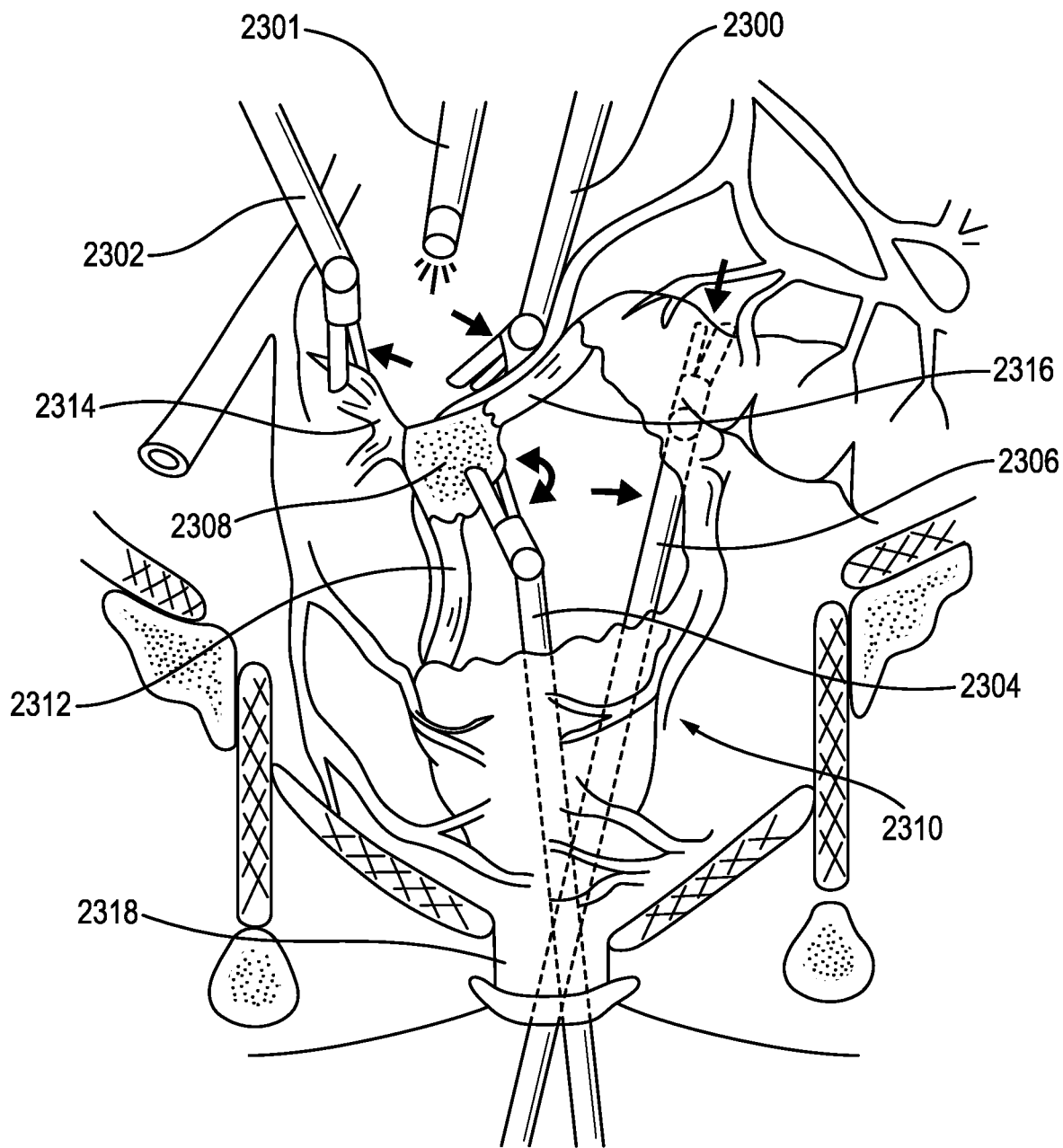
FIG. 29 is a schematic view of a conventional surgical system inserted into an organ.

Further, as illustrated in FIG. 29, multiple graspers 2300, 2302, 2304, 2306 and a laparoscope 2301 are needed to position a tumor 2308 for removal from the colon 2310. During dissection of the colon 2310, the tumor 2308 should be placed under tension, which requires grasping and stretching the surrounding healthy tissue 2312, 2314, 2316 of the colon 2310. However, the manipulating of the tissue 2312, 2314, 2316 surrounding the tumor 2308 can suffer from reduced blood flow and trauma due to the graspers 2300, 2302, 2304, 2306 placing a high grip force on the tissue 2312, 2314, 2316. Additionally, during a colectomy, the transverse colon and upper descending colon may need to be mobilized allowing the good remaining colon to be brought down to connect to the rectum 2318 after the section of the colon 2310 containing the tumor 2308 is transected and removed. A surgical tool that can be used to safely manipulate the colon to provide the surgeon with better visualization and access to the arteries and veins during mobilization would help prevent trauma and blood loss to the surrounding area during a colectomy.

Figure 30:
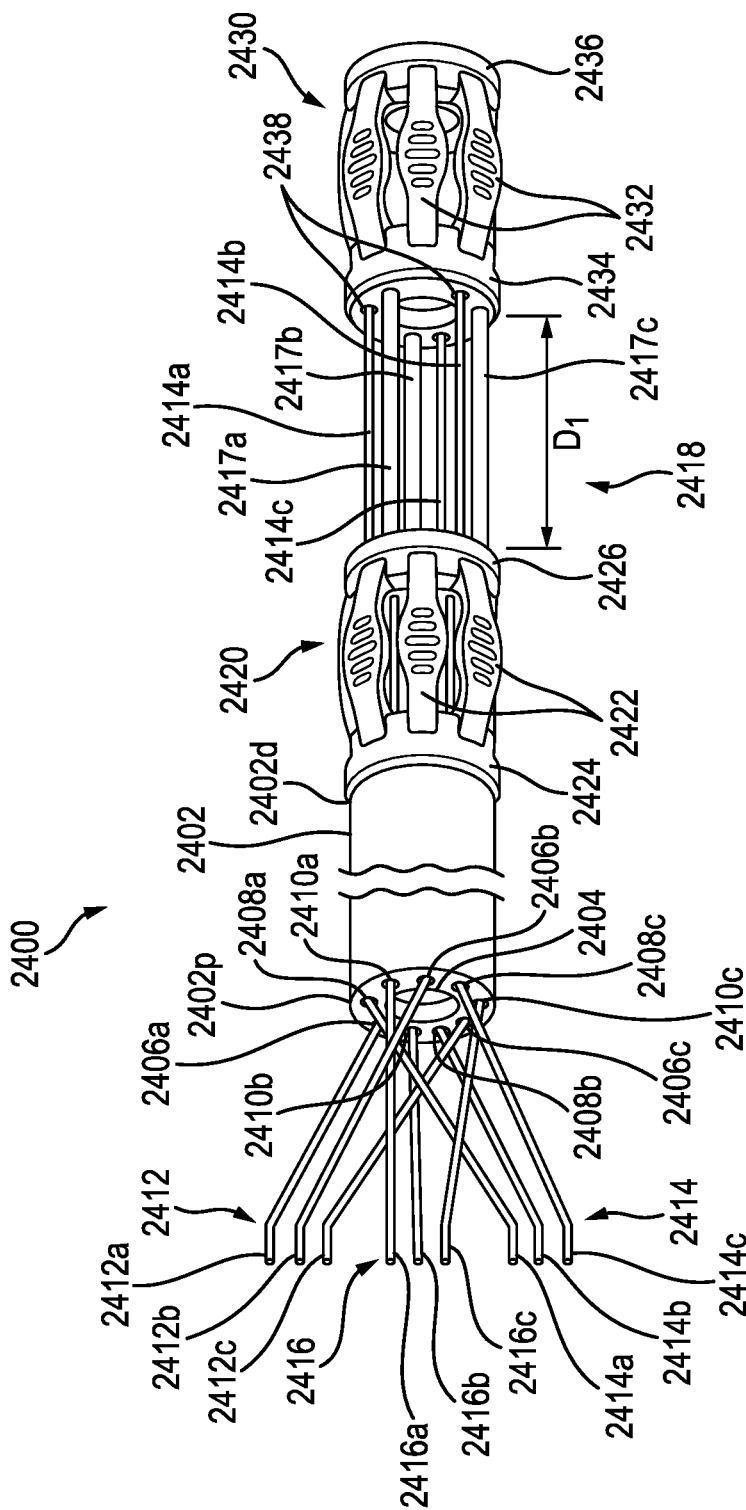
FIG. 30 is a schematic view of another embodiment of a surgical anchoring system having first and second anchor members, showing the first and second anchor members in an unexpanded state.
Figure 31:
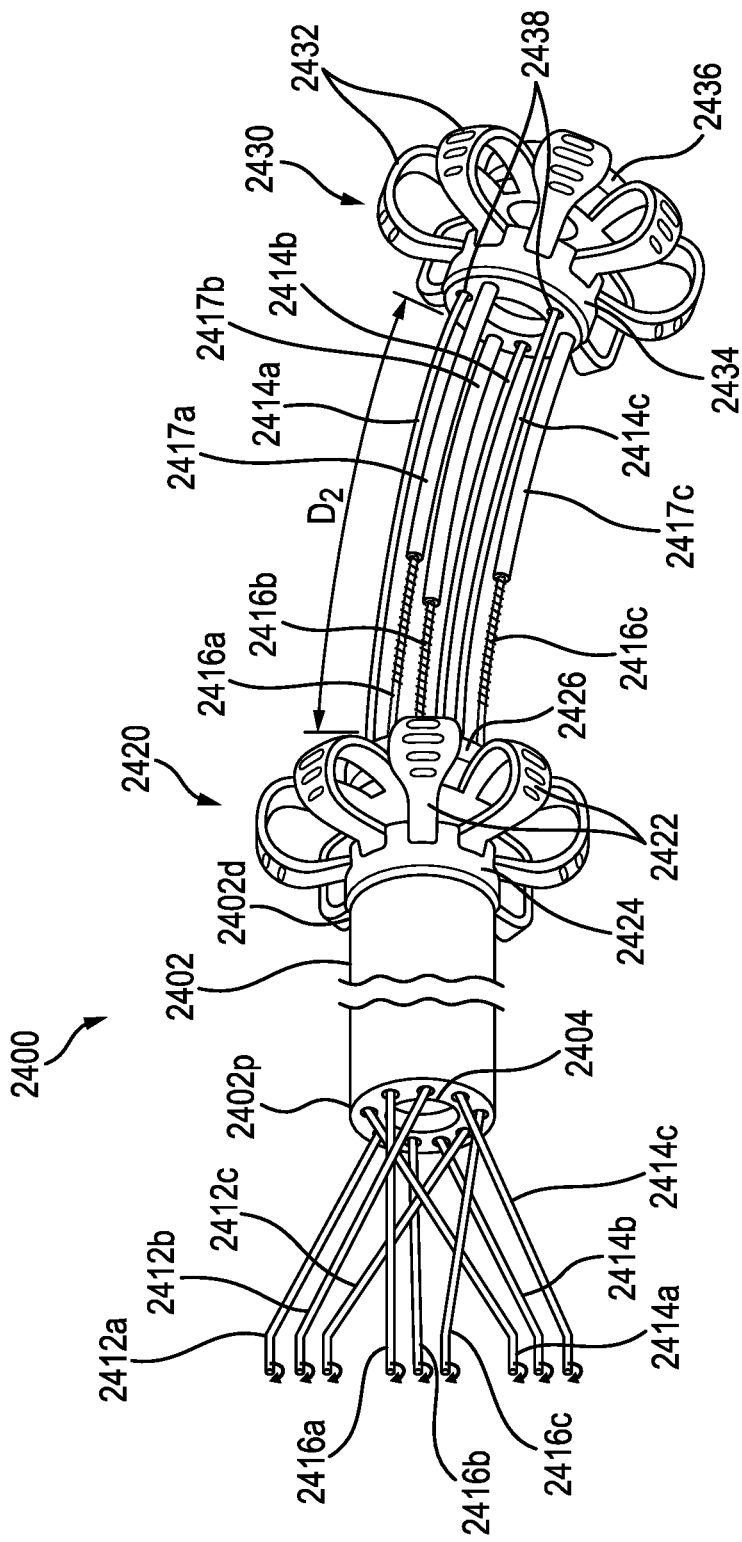
FIG. 31 is a schematic view of the surgical anchoring system of FIG. 30, showing the first and second anchor members in an expanded state.

FIG. 30 and FIG. 31 illustrate one embodiment of a surgical anchoring system 2400 that is configured for endoluminal access into and manipulation of a colon 2310. As will be described in more detail below, the surgical anchoring system 2400 is used to manipulate and tension a portion of the colon 2310 (e.g., section F). For purposes of simplicity, certain components of the surgical anchoring system 2400 and the colon 2310 are not illustrated. While this surgical anchoring system 2400 is shown and described in connection with manipulation of section F of the colon 2310, a person skilled in the art will appreciate that the surgical anchoring system 2400 can be used to additionally, or in the alternative, inflate other sections of the colon 2310.

As illustrated in FIG. 30 and FIG. 31, the surgical anchoring system 2400 can have a variety of configurations. In some embodiments, the surgical anchoring system 2400 includes a tubular member 2402 configured for endoluminal access through a natural orifice, such as the rectum 2318 and into the colon 2310. The tubular member 2402 includes a central lumen 2404 arranged therein and configured to receive an endoscope. Additionally, the tubular member 2402 includes a plurality of working channels formed from working channels 2406a, 2406b, 2406c, 2408a, 2408b, 2408c, 2410a, 2410b, 2410c extending therethrough. In other embodiments, the tubular member can have other suitable configurations and shapes.

Figure 32:
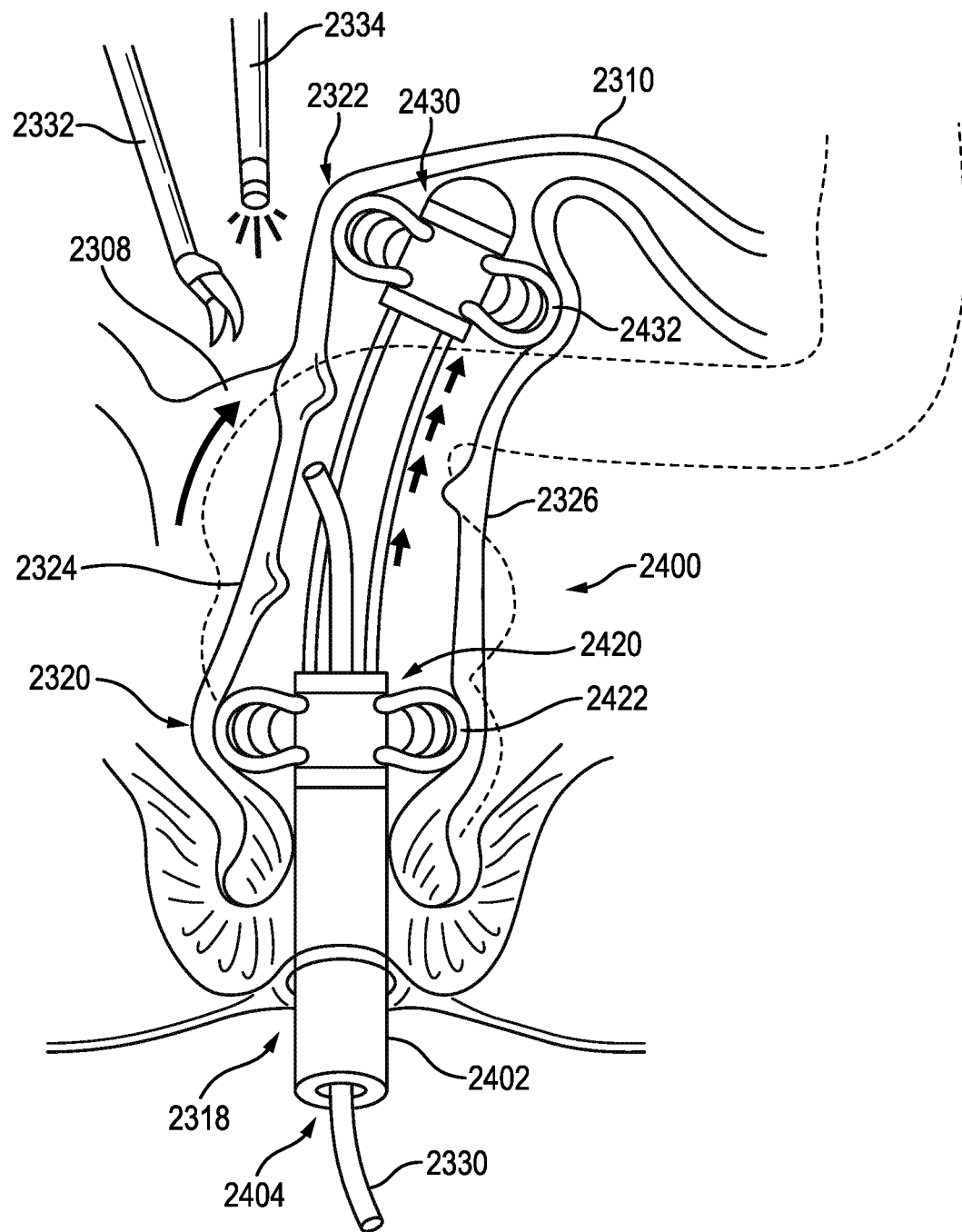
FIG. 32 is a cross-sectional view of the surgical anchoring system of FIG. 31, showing the surgical anchoring system inserted into an organ.

The surgical anchoring system 2400 also includes an anchoring assembly 2418 coupled to the tubular member 2402 and extending distally from the distal end 2402d of the tubular member 2402. The anchoring assembly 2418 includes a first anchor member 2420 and a second anchor member 2430. The first anchor member 2420 is coupled to the distal end 2402*d* of the tubular member 2402 and is configured to engage a first anatomical location and secure the first anatomical location relative to the tubular member 2402 (FIG. 32). The first anchor member 2420 includes a first plurality of expandable anchoring elements 2422 extending between a proximal collar 2424 and a distal collar 2426. The distal collar 2426 is configured to axially move relative to the proximal collar 2424, such that when the distal collar 2426 moves axially towards the proximal collar 2424, the expandable anchoring elements 2422 expand radially outward from the axis of axial movement by the distal collar 2426. By expanding radially outward, the expandable anchoring elements 2422 are configured to at least partially contact an inner tissue surface of a natural body lumen or organ while in an expanded state.

In order to axially displace the distal collar 2426 towards the proximal collar 2424, a first plurality of actuators 2412 is connected to the distal collar 2426. The first plurality of actuators 2412 includes actuators 2412*a*, 2412*b*, 2412*c*, where actuator 2412*a* passes through the working channel 2406*a*, actuator 2412*b* passes through the working channel 2406*b*, and the actuator 2412*c* passes through the working channel 2406*c*. As the actuators 2412*a*, 2412*b*, 2412*c* are tensioned and pulled through or rotated within the working channels, the distal collar 2426 is axially displaced towards the proximal collar 2424, expanding the expandable anchoring elements 2422. In order for the actuators 2412*a*, 2412*b*, 2412*c* to interact with the distal collar 2426, the actuators 2412*a*, 2412*b*, 2412*c* pass through a plurality of working channels (not shown) within the proximal collar 2424.

The second anchor member 2430 is moveable relative to the first anchor member 2420 and positioned distal to the first anchor member 2420 at a distance $D_1$. The second anchor member 2430 is configured to engage a second anatomical location and is moveable relative to the first anatomical location (FIG. 32). The second anchor member 2430 includes a second plurality of expandable anchoring elements 2432 extending between a proximal collar 2434 and a distal collar 2436. The distal collar 2436 is configured to axially move relative to the proximal collar 2434, such that when the distal collar 2436 moves axially towards the proximal collar 2434, the expandable anchoring elements 2432 expand radially outward from the axis of axial movement by the distal collar 2436. By expanding radially outward, the expandable anchoring elements 3432 are configured to at least partially contact an inner tissue surface of a natural body lumen or organ while in an expanded state.

In order to axially displace the distal collar 2436 towards the proximal collar 2434, a second plurality of actuators 2414 is connected to the distal collar 2436. The second plurality of actuators 2414 includes actuators 2414*a*, 2414*b*, 2414*c*, where actuator 2414*a* passes through the working channel 2408*a*, actuator 2414*b* passes through the working channel 2408*b*, and the actuator 2414*c* passes through the working channel 2408*c*. As the actuators 2414*a*, 2414*b*, 2414*c* are tensioned and pulled through or rotated within the working channels, the distal collar 2436 is axially displaced towards the proximal collar 2434, expanding the expandable anchoring elements 2432. In order for the actuators 2414*a*, 2414*b*, 2414*c* to interact with the distal collar 2436, the actuators 2414*a*, 2414*b*, 2414*c* pass through working channels 2438 within the proximal collar 2434, and a plurality of working channels (not shown) within the proximal collar 2424 and the distal collar 2426 of the first anchoring element 2420.

As illustrated in FIG. 31 and FIG. 32, with the first anchor member 2424 and the second anchor member 2434 in expanded states, the first anchor member 2424 is engaged with the first anatomical location 2320, and the second anchor member is engaged with the second anatomical location 2322. In order to axially displace the second anchor member 2430 relative to the first anchor member 2420, the actuators 2416*a*, 2416*b*, 2416*c* are rotated in order to unscrew the actuators 2416*a*, 2416*b*, 2416*c* from the threaded sheaths 2417*a*, 2417*b*, 2417*c*. The actuator 2416*a* is threaded within the threaded sheath 2417*a*, the actuator 2416*b* is threaded within the threaded sheath 2417*b*, and actuator 2416*c* is threaded within the threaded sheath 2417*c*. Since the actuators and threaded sheaths have complementary threads, the rotation of the actuators 2416*a*, 2416*b*, 2416*c* causes the distance between the first anchor member 2420 and the second anchor member 2430 to increase. In some embodiments, once of the actuators 2416*a*, 2416*b*, 2416*c* can be rotated more than the other actuators, causes a curved length $D_2$, which is greater than $D_1$, between the first anchor member 2420 and the second anchor member 2430.

In use, the curved length $D_2$ can be used to create tension on one side of the colon 2310, such as where the location of a tumor is located. Since the first anatomical location 2320 is engaged with the first anchor member 2420 by the expandable anchoring elements 2422, and the second anatomical location 232 is engaged with the second anchor member 2430 by the expandable anchoring elements 2432, when the actuators 2416*a*, 2416*b*, 2416*c* are rotated and unthreaded, the second anatomical location 2322 is selectively repositioned relative to the first anatomical position 2320.

As illustrated in FIG. 32, the tissue wall 2324 is tensioned at a greater degree than the tissue wall 2326, arranged opposite the tissue wall 2324. By tensioning the tissue wall 2324, where the tumor 2308 is located on the colon 2310, the tumor can be visualized and removed by laparoscopically arranged instruments 2332, 2334. Additionally, to further help visualize the tumor 2308, an endoscope 2330 is arranged within the central lumen 2404 of the tubular member 2402.

Sensing Surgical Instruments

During certain surgical procedures, it may be advantageous to be able to track the location and orientation of certain surgical instruments within a patient's body. For example, during a colon resection, the mobilized portion of the colon must be aligned and connected to the rectum in order to reattach the colon to the rectum. In certain surgical systems, at least one of the surgical instruments can include integrated tracking and coordinating means that identifies a location of the surgical instruments relative to each other.

In some embodiments, a surgical instrument can include one or more markers (e.g., attachable or integrated markers) that can be used to track the surgical instrument. This can allow the surgical instrument to directly cooperate with the dual sensing and cooperative control systems. As a result, the surgical instrument can be directly inserted into the body (e.g., into a natural orifice) without a scope (e.g., an endoscope) and used similarly to a scope for.

Figure 33:
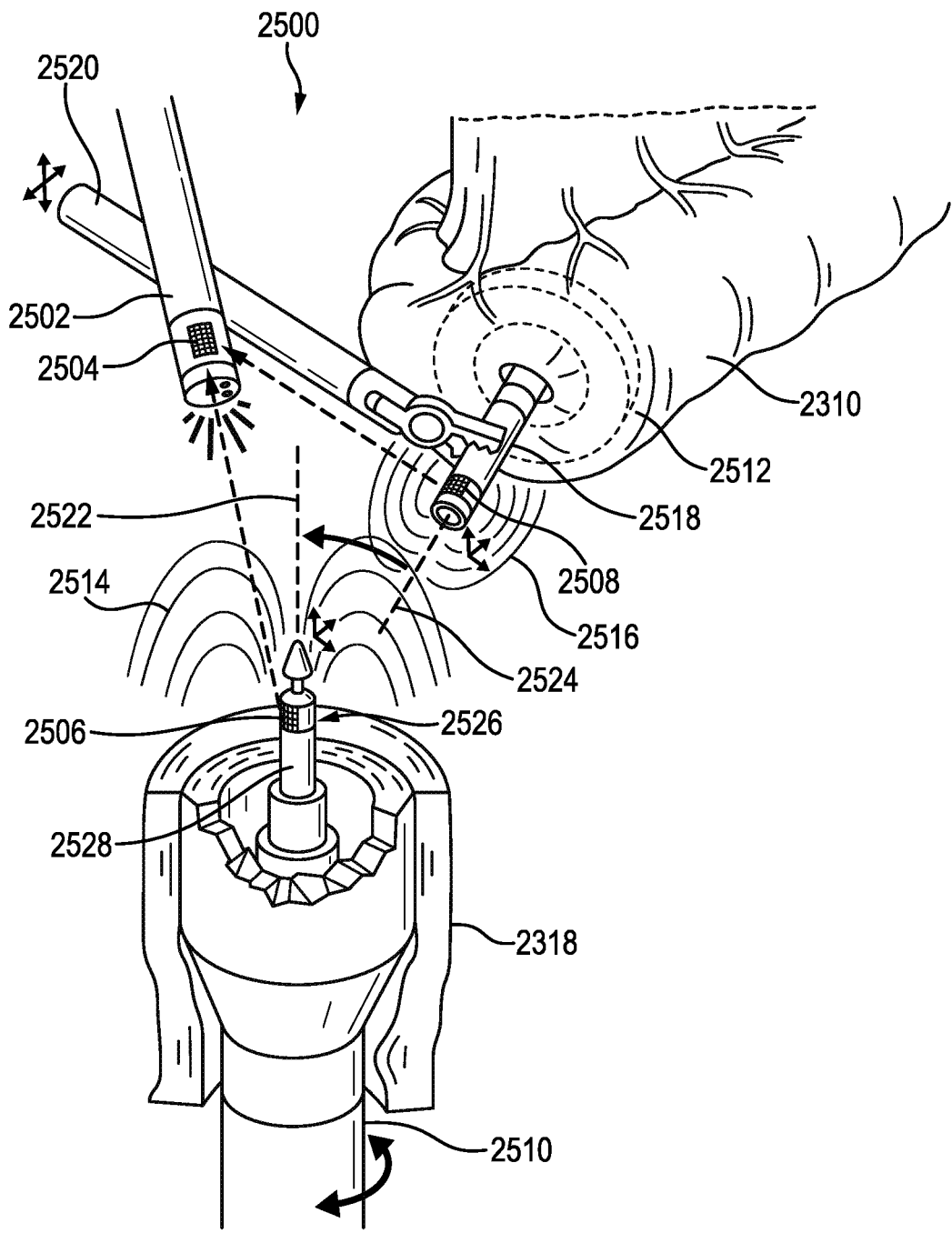
FIG. 33 is a schematic view of another embodiment of a surgical anchoring system having a circular stapler and anvil, each having a tracking means, showing the surgical anchoring system inserted through rectum and into a colon with a portion the circular stapler passing through the rectum and into the colon and the anvil passing through a mobilized portion of the colon.

FIG. 33 illustrates another embodiment of a surgical anchoring system 2500. The surgical anchoring system 2500 includes attachable or integrated markers and a sensing means for use with an instrument introduced through a natural orifice without another scope that would enable it to cooperate with the dual sensing and cooperative control systems.

The surgical anchoring system 2500 includes a laparoscopically arranged instrument 2502 having a sensing array 2504. The sensing array 2504 is configured to interact wirelessly with a first collar 2506 and a second collar 2508 in order to align a circular stapler 2510 arranged within the rectum 2318 with the anvil 2512 arranged within the remainder of the colon 2310. The first collar 2506 is arranged within the circular stapler 2510 and emits a magnetic field 2514. The second collar 2508 is arranged on the anvil 2512 and emits a magnetic field 2516. Both the magnetic fields 2514, 2516 are detectable by the sensing array 2504. The magnetic fields 2514, 2516 are configured to relay location and orientation data about the circular stapler 2510 and the anvil 2512 in order to align the colon 2310 with the rectum 2318.

The anvil 2512 include a post 2518, which is grasped by an instrument 2520 in order to mobilize the colon 2310. As the anvil 2512 is moved by the instrument 2520, the sensing array 2504 collects magnetic field data and determines the distance and misalignment of the stapler trocar axis 2522 and the anvil trocar axis 2524. When the stapler trocar axis 2522 is aligned with the anvil trocar axis 2524, the anvil 2512 can be positioned over the post 2526 of the circular stapler 2510. The post 2526 can include alignment features 2528 as the post 2518 is arranged over the post 2526. In certain embodiments, the circular stapler 2510 can be rotated once the posts 2518, 2526 are aligned with each other, coupling the anvil 2512 to the circular stapler 2510 so that the colon 2310 can be stapled to the rectum 2318.

The instrument 2502 can include an optical sensor arranged on the distal end thereof in order to visualize the treatment area to an external screen in view of a user, aiding them in adjusting and aligning the circular stapler to the correct location for anvil attachment from the laparoscopic side.

The surgical anchoring system disclosed herein can be designed to be disposed of after a single use, or they can be designed to be used multiple times. In either case, however, the surgical anchoring system can be reconditioned for reuse after at least one use. Reconditioning can include any combination of the steps of disassembly of the surgical anchoring system, followed by cleaning or replacement of particular pieces and subsequent reassembly. In particular, the surgical anchoring system can be disassembled, and any number of the particular pieces or parts of the surgical anchoring system can be selectively replaced or removed in any combination. Upon cleaning and/or replacement of particular parts, the surgical anchoring system can be reassembled for subsequent use either at a reconditioning facility, or by a surgical team immediately prior to a surgical procedure. Those skilled in the art will appreciate that reconditioning of a surgical anchoring system can utilize a variety of techniques for disassembly, cleaning/replacement, and reassembly. Use of such techniques, and the resulting reconditioned instrument, are all within the scope of the present application.

Instrument Control Imaging Systems

Devices, systems, and methods for multi-source imaging provided herein allow for cooperative surgical visualization. In general, in cooperative surgical visualization, first and second imaging systems (e.g., first and second scope devices) each gathering images of a surgical site are configured to cooperate to provide enhanced imaging of a surgical site. The cooperative surgical visualization may improve visualization of patient anatomy at the surgical site and/or improve control of surgical instrument(s) at the surgical site.

A surgical visualization system can allow for intraoperative identification of critical structure(s) (e.g., diseased tissue, anatomical structures, surgical instrument(s), etc.). The surgical visualization system may thus enable enhanced intraoperative decision making and improved surgical outcomes. The surgical visualization system can provide advanced visualization capabilities beyond what a medical practitioner sees with the "naked eye" and/or beyond what an imaging system can recognize and/or convey to the medical practitioner. The surgical visualization system can augment and enhance what a medical practitioner is able to know prior to tissue treatment (e.g., dissection, etc.) and, thus, may improve outcomes in various instances. As a result, the medical practitioner can confidently maintain momentum throughout the surgical procedure knowing that the surgical visualization system is tracking a critical structure, which may be approached during dissection, for example. The surgical visualization system can provide an indication to the medical practitioner in sufficient time for the medical practitioner to pause and/or slow down the surgical procedure and evaluate the proximity to the critical structure to prevent inadvertent damage thereto. The surgical visualization system can provide an ideal, optimized, and/or customizable amount of information to the medical practitioner to allow the medical practitioner to move confidently and/or quickly through tissue while avoiding inadvertent damage to healthy tissue and/or critical structure(s) and, thus, to minimize the risk of harm resulting from the surgical procedure.

The surgical systems provided herein generally include a first scope device configured to transmit image data of a first scene within its field of view, a second scope device configured to transmit image data of a second, different scene within its field of view, a tracking device associated with one of the first scope device or the second scope device and configured to transmit a signal indicative of a location of the one of the first scope device or the second scope device relative to the other one of the first scope device or the second scope device, a controller configured to receive the transmitted data and signal, determine the relative distance between the first and second scope devices and provide a merged image. The merged image can be at least a portion of at least the first scope device and the second scope device in a single scene, and at least one of the first scope device and the second scope device in the merged image is a representative depiction thereof. Thus, the merged image may thus provide two separate points of view of the surgical site, which can conveniently allow a medical practitioner to view only one display instead of multiple displays. Further, within that one display, the merged image allows a medical practitioner to coordinate relative location and/or orientation of at least the first and scope devices arranged at or proximate to the surgical site.

The first scope device is configured to be at least partially disposed within at least one of a natural body lumen and an organ (e.g., a lung, a stomach, a colon, or small intestines), and the second scope device is configured to be at least partially disposed outside of the at least one of the natural body lumen and the organ. In certain embodiments, the first scope device is endoscope and the second scope device is a laparoscope. The natural body lumen or organ can be any suitable natural body lumen or organ. Non-limiting examples include a stomach, a lung, a colon, or small intestines.

The surgical systems provided herein can also be used in various robotic surgical systems, such as those discussed above, and can incorporate various tracking and/or imaging mechanisms, such as electromagnetic (EM) tracked tips, fiber bragg grating, virtual tags, fiducial markers, use of probes, identification of known anatomy, various 3D scanning techniques such as using structured light, various sensors and/or imaging systems discussed previously, etc., to assist in tracking movement of the instruments, endoscopes, and laparoscopes relative to each other and/or the overall system. The tracking mechanisms can be configured to transmit tracking data from both a laparoscope and an endoscope so that the location of either scope can be determined relative to the other scope. Additionally, critical structures within the field of view of either scope (e.g., diseased tissue, surgical instruments, anatomical structures) can be tracked by the scope which has such critical structures within their field of view. In total, the surgical systems herein can track the objects within a field of view of each scope, and the relative position of each scope. Therefore, the totality of the tracking data allows the system to calculate the distance of a critical structure from a scope which does not have a critical structure in its field of view based on the tracking data collected by the other scope.

In some embodiments, the surgical system can include a tracking device associated with one of the first scope device or the second scope device and configured to transmit a signal indicative of a location of the one of the first scope device or the second scope device relative to the other one of the first scope device or the second scope device.

In various embodiments, the surgical systems provided herein includes a controller. The surgical system, the controller, a display, and/or the various instruments, endoscopes, and laparoscopes can also be incorporated into a number of different robotic surgical systems and/or can be part of a surgical hub, such as any of the systems and surgical hubs discussed above. The controller in general is configured to merge first and second scenes from an endoscope and a laparoscope, respectively, to visually create a merged image between the first and second scenes. The controller is configured to receive the tracking data detailed above, and in combination with the first and second scenes, generate the merged image containing a representative depiction of at least the endoscope or laparoscope, and any structures within field of view of the scope which is visually impaired by a tissue wall. For example, if the merged image was from a point-of-view of the endoscope, the merged image is the live image stream of what the endoscope is viewing, while including an overlay of the orientations and locations of laparoscopically arranged surgical instruments and a laparoscope, if present.

In some embodiments, the controller can be configured to receive the transmitted image data of the first and second scenes from the first and second scope devices and the transmitted signal from a tracking device, to determine, based on the transmitted signal, a relative distance between the first scope device and the second scope device, and to provide, based on the transmitted image data and relative distance between the first and second scopes, a merged image of at least a portion of at least the first scope device and the second scope device in a single scene, wherein at least one of the first scope device and the second scope device in the merged image is a representative depiction thereof.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with stomach, a person skilled in the art will appreciate that these surgical systems can be used in connection with any other suitable natural body lumens or organs.

Surgery is the most common treatment for stomach cancer. When surgery is required for stomach cancer, the goal is to remove the entire tumor as well as a good margin of healthy stomach tissue around the tumor. Different procedures can be used to remove stomach cancer. The type of procedure used depends on what part of the stomach the cancer is located and how far it has grown into nearby areas. For example, endoscopic mucosal resection (EMR) and endoscopic submucosal dissection (ESD) are procedures on the stomach that can be used to treat some early-stage cancers. These procedures do not require a cut in the skin, but instead the surgeon passes an endoscope down the throat and into the stomach of the patient. Surgical tools (e.g., MEGADYNE™ Tissue Dissector or Electrosurgical Pencils) are then passed through the working channel of the endoscope to remove the tumor and some layers of the normal stomach wall below and around it.

Other surgical procedures include a subtotal (partial) or a total gastrectomy that can be performed as an open procedure (e.g., surgical instruments are inserted through a large incision in the skin of the abdomen) or as a laparoscopic procedure (surgical instruments are inserted into the abdomen through several small cuts). A laparoscopic gastrectomy procedure generally involves insufflation of the abdominal cavity with carbon dioxide gas to a pressure of around 15 millimeters of mercury (mm Hg). The abdominal wall is pierced and a 5-10 mm in diameter straight tubular cannula or trocar is then inserted into the abdominal cavity. A laparoscope connected to an operating room monitor is used to visualize the operative field and is placed through one of the trocar(s). Laparoscopic instruments are placed through two or more additional trocars for manipulation by the surgeon and surgical assistant(s) to remove the desired portion(s) of the stomach.

Figure 34:
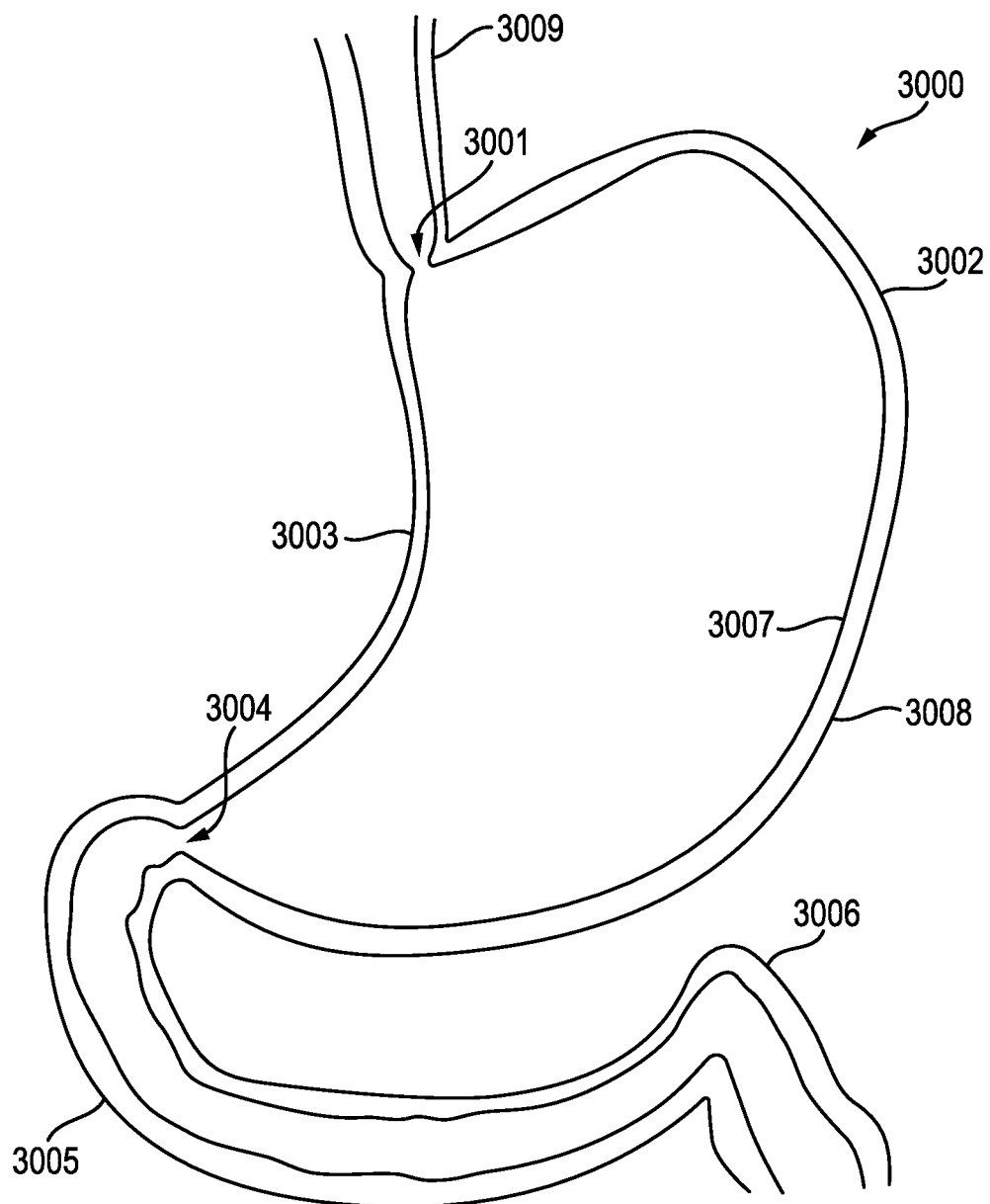
FIG. 34 is a schematic view of a stomach.

FIG. 34 illustrates a schematic depiction of a stomach 3000. The stomach 3000 can include an esophageal sphincter 3001, a greater curvature 3002, a lesser curvature 3003, a pyloric sphincter 3004, a duodenum 3005, and a duodenojejunal flexure 3006. Additionally, the stomach 3000 includes an inner tissue wall 3007 and an outer tissue wall 3008. The esophageal sphincter 3001 connects the stomach to the esophagus 3009, and allows an endoscope to be passed through a patient's mouth, down the esophagus 3009, and passed the esophageal sphincter 3001 in order to access the intraluminal space of the stomach 3000. The pyloric sphincter 3004, duodenum 3005, and duodenojejunal flexure 3006 connect the stomach 3000 to the small intestines (not shown).

Figure 35:
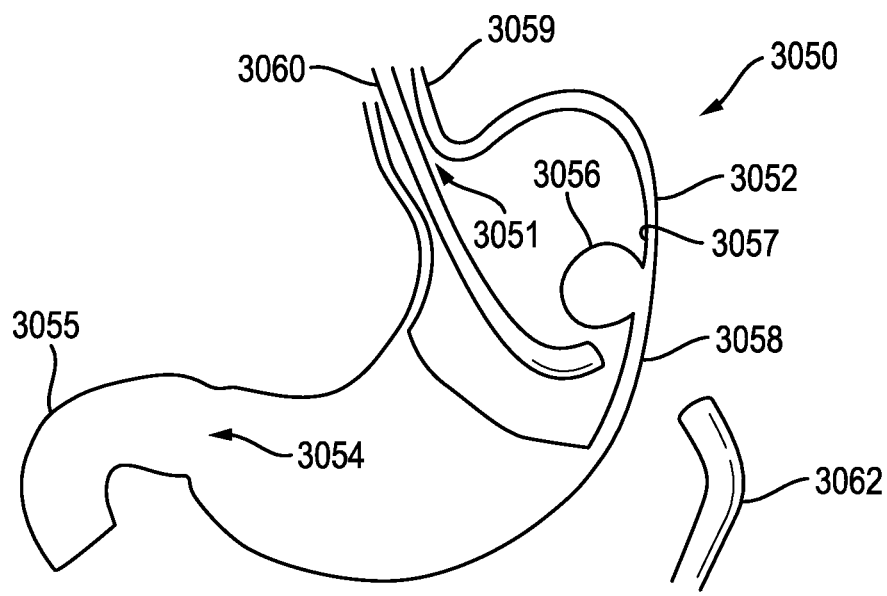
FIG. 35 is a schematic view of a conventional surgical system having a laparoscope and an endoscope, showing the laparoscope positioned outside of a stomach and an endoscope positioned within the stomach.
Figure 36:
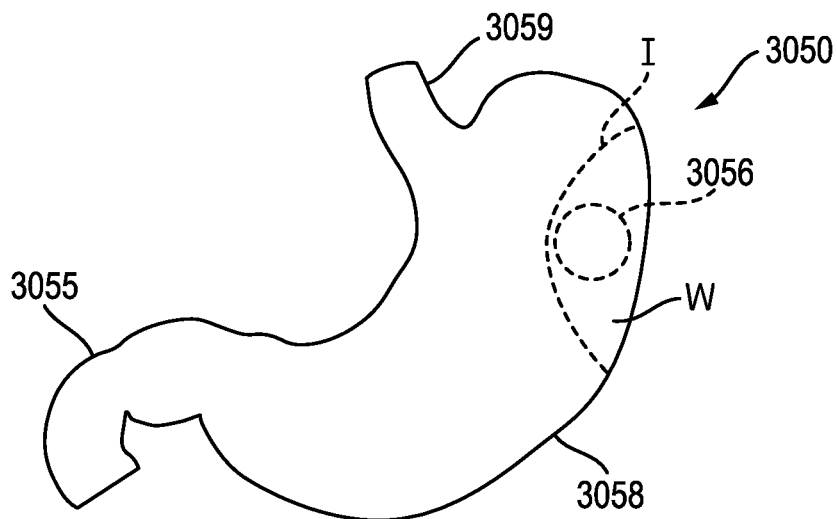
FIG. 36 is a schematic view of the stomach of FIG. 35, showing a conventional wedge resection to remove a tumor from the stomach using the surgical system of FIG. 35.

A conventional surgical procedure to remove a tumor from a stomach is called a wedge resection, where the portion of the stomach where the tumor is arranged is removed in full. FIG. 35 and FIG. 36 illustrate an exemplary embodiment of a conventional surgical system that is configured for endoluminal and laparoscopic access into a stomach 3050 to remove a tumor 3056. Similar to the stomach 3000, the stomach 3050 includes an esophageal sphincter 3051, a greater curvature 3052, a lesser curvature 3053, a pyloric sphincter 3054, a duodenum 3055, an inner tissue wall 3057, and an outer tissue wall 3058. As illustrated, the tumor 3056 is arranged on the inner tissue wall 3057 of the greater curvature 3052. The tumor 3056 is arranged away from the esophageal sphincter 3051 and esophagus 3059, and on the inner tissue wall 3057 of the greater curvature 3052. In order to remove the tumor 3056, an endoscope 3060 is arranged in the intraluminal space, and a laparoscope 3062 is arranged in the extraluminal space.

While both the endoscope 3060 and the laparoscope 3062 are providing image data to a display so that a surgeon can properly position the scopes and operate on the stomach 3050, the images from each scope are separate, requiring the surgeon to look at two different monitors, or a frame-in-frame arrangement. This is problematic when both the endoscope 3060 and the laparoscope 3062 must work cooperatively in order to create the incision line I to remove the wedge W with the tumor 3056 attached. The surgeon therefore typically relies on their experience or knowledge of the anatomy to ensure the endoscope 3060 and laparoscope 3062 are working cooperatively and arranged in the correct location on either side of the inner tissue wall 3057 and outer tissue wall 3058.

With conventional surgical systems, a unified visual image of a connected or joint surgical treatment site cannot be provided. Instead, a user is required either to monitor multiple displays at the same time and guess as to the orientation and distance between various surgical instruments and/or scopes visualized by different scopes involved in the same procedure or to incorporate an additional visual system into the procedure in an attempt to track the scopes and instruments. The surgical systems provided herein avoid these issues by integrating imaging from both an endoscope and a laparoscope into a single visual display to simplify alignment and deployment of various surgical instruments and scopes.

Figure 37:
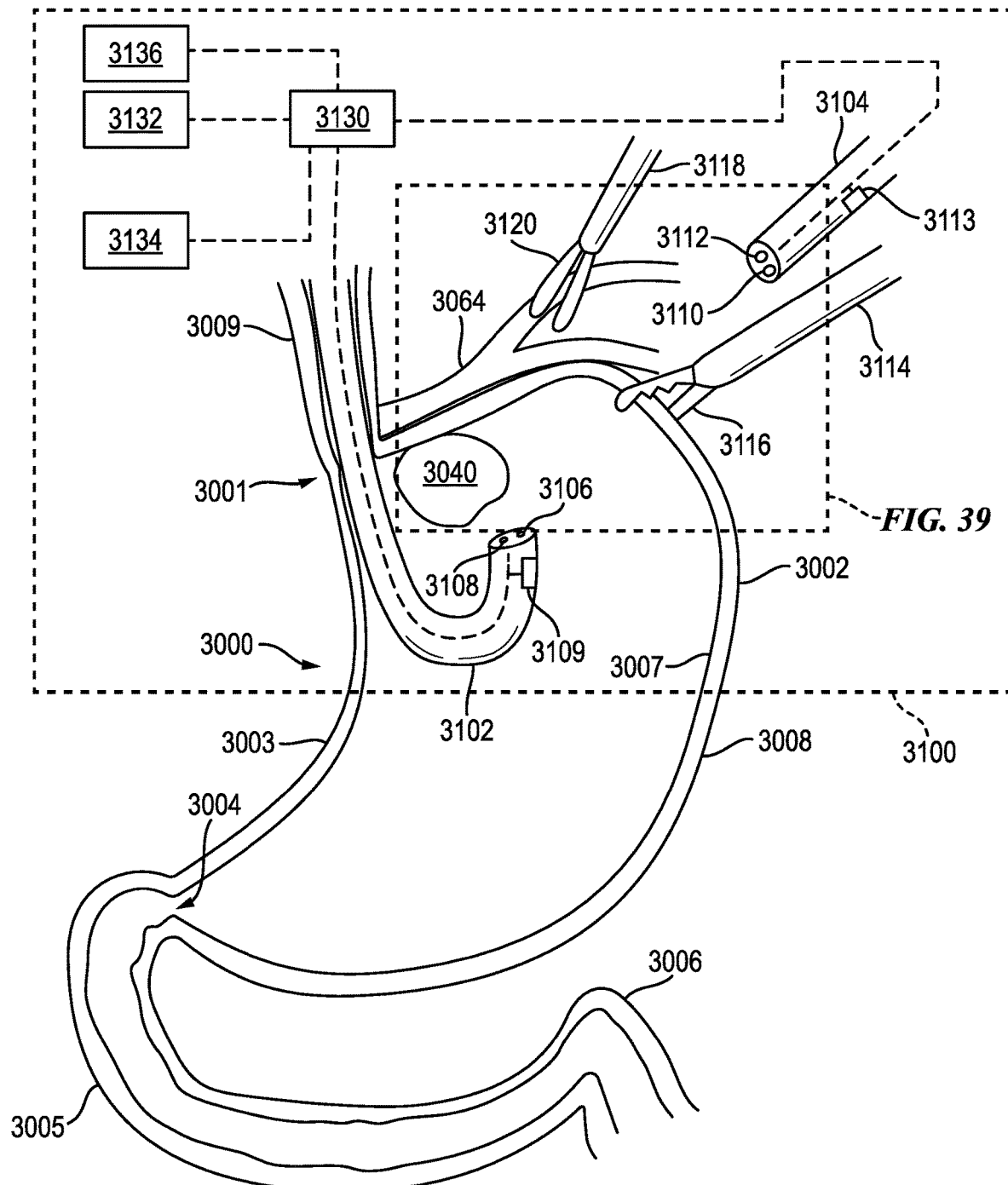
FIG. 37 is a schematic view of an embodiment of a surgical system having a laparoscope, laparoscopic instruments, and an endoscope, showing the laparoscope and laparoscopic instruments positioned outside of a stomach and the endoscope positioned within the stomach.

FIG. 37 illustrates an exemplary embodiment of a surgical system 3100 that is configured for endoluminal access into and laparoscopic access of the stomach 3000. As will be described in more detail below, the surgical system 3100 can transmit data from different scope devices in order to create a merged image of a single scene at the surgical site, which can include a representative depiction of at least one of the scope devices in the merged image. For purposes of simplicity, certain components of the surgical system 3100 and the stomach 3000 are not illustrated.

As shown, the stomach 3000 includes a tumor 3040 arranged on the greater curvature 3002. When operating on the stomach 3000, the blood vessels 3064 may need to be manipulated (e.g., mobilized) using laparoscopically arranged instruments in order to properly access the tumor 3040. In use, as described in more detail below, the surgical system 3100 can provide a merged image so that the endoscope and laparoscope can operate cooperatively while neither scope can visually see the other in their field of view (e.g., due to the stomach wall positioned therebetween).

The surgical system 3100 includes an endoscope 3102 that is configured for endoluminal access through the esophagus 3009 and into the stomach 3000. The endoscope 3102 can have a variety of configurations. For example, in this illustrated embodiment, the endoscope 3102 includes a first optical sensor 3106 (e.g., a camera) and lighting element 3108. Alternatively, or in addition, the endoscope 3102 can include a working channel (not shown) arranged along the length of the endoscope 3102 to pass an instrument endoluminally into the stomach 3000. In some embodiments, the endoscope 3102 can include an outer sleeve (not shown) configured to be inserted through a patient's mouth (not shown) and down the esophagus 3009. The outer sleeve can include a working channel that is configured to allow the endoscope 3102 to be inserted through the outer sleeve and access the stomach 3000. In certain embodiments, the endoscope 3102 can include a working channel extending therethrough. This working channel can be configured to receive one or more surgical instruments and/or allow fluid to pass therethrough to insufflate a lumen or organ (e.g., the stomach).

Further, the surgical system 3100 includes a laparoscope 3104 that is configured for laparoscopic access through the abdominal wall (not shown) and into the extraluminal anatomical space adjacent to the stomach 3000. The laparoscope 3104 can have a variety of configurations. For example, in this illustrated embodiment, the laparoscope 3104 includes a second optical sensor 3110 (e.g., a camera) and a lighting element 3112. Alternatively, or in addition, the laparoscope 3104 can include a working channel (not shown) arranged along the length of the laparoscope 3104 to pass an instrument laparoscopically into the extraluminal space. In some embodiments, the laparoscope 3104 can be inserted into the extraluminal anatomical space through a trocar or multi-port (not shown) positioned within and through a tissue wall. The trocar or multi-port can include ports for passing the laparoscope 3104 and/or other surgical instruments into the extraluminal anatomical space to access the stomach 3000.

As shown in FIG. 37, the endoscope 3102 includes a first tracking device 3109 disposed on or within the endoscope 3102. The first tracking device 3109 is configured to transmit (e.g., to controller 3130) a signal that is indicative of a location of the endoscope 3102 relative to the laparoscope 3004. Additionally, the laparoscope 3104 includes a second tracking device 3113 disposed on or within the laparoscope 3104. The second tracking device 3113 is configured to transmit (e.g., to controller 3130) a signal that is indicative of a location of the laparoscope 3104 relative to the endoscope 3102. In other embodiments, only one of the endoscope 3102 and the laparoscope 3104 include a tracking device.

Alternatively, or in addition, the transmitted signal (or an additional transmitted signal) from the first tracking device 3109 can be further indicative of an orientation of the endoscope 3102 relative to the laparoscope 3004. Alternatively, or in addition, the transmitted signal (or an additional transmitted signal) from the second tracking device 3113 can be further indicative of an orientation of the laparoscope 3004 relative to the first scope device.

In some embodiments, the first and second tracking devices 3109, 3113 are configured to use magnetic or radio frequency sensing to detect a location, an orientation, or both of the endoscope 3102 and laparoscope 3104, respectively (e.g., when the endoscope 3102 and laparoscope 3104 positioned on opposite sides of the tissue wall of the stomach 3000). Alternatively, the first and second tracking devices 3109, 3113 are configured to use common anatomic landmarks to detect a location, an orientation, or both of the endoscope 3102 and laparoscope 3104, respectively (e.g., when the endoscope 3102 and laparoscope 3104 positioned on opposite sides of the tissue wall of the stomach 3000). The first and second tracking devices 3109, 3113 can each transmit the signal(s) to a controller (like controller 3130). Various embodiments of magnetic fiducial markers and using magnetic fiducial markers in detecting location are discussed further, for example, in U.S. Pat. App No. 63/249,658 entitled "Surgical Devices, Systems, And Methods For Control Of One Visualization With Another" filed on Sep. 29, 2021.

Figure 38:
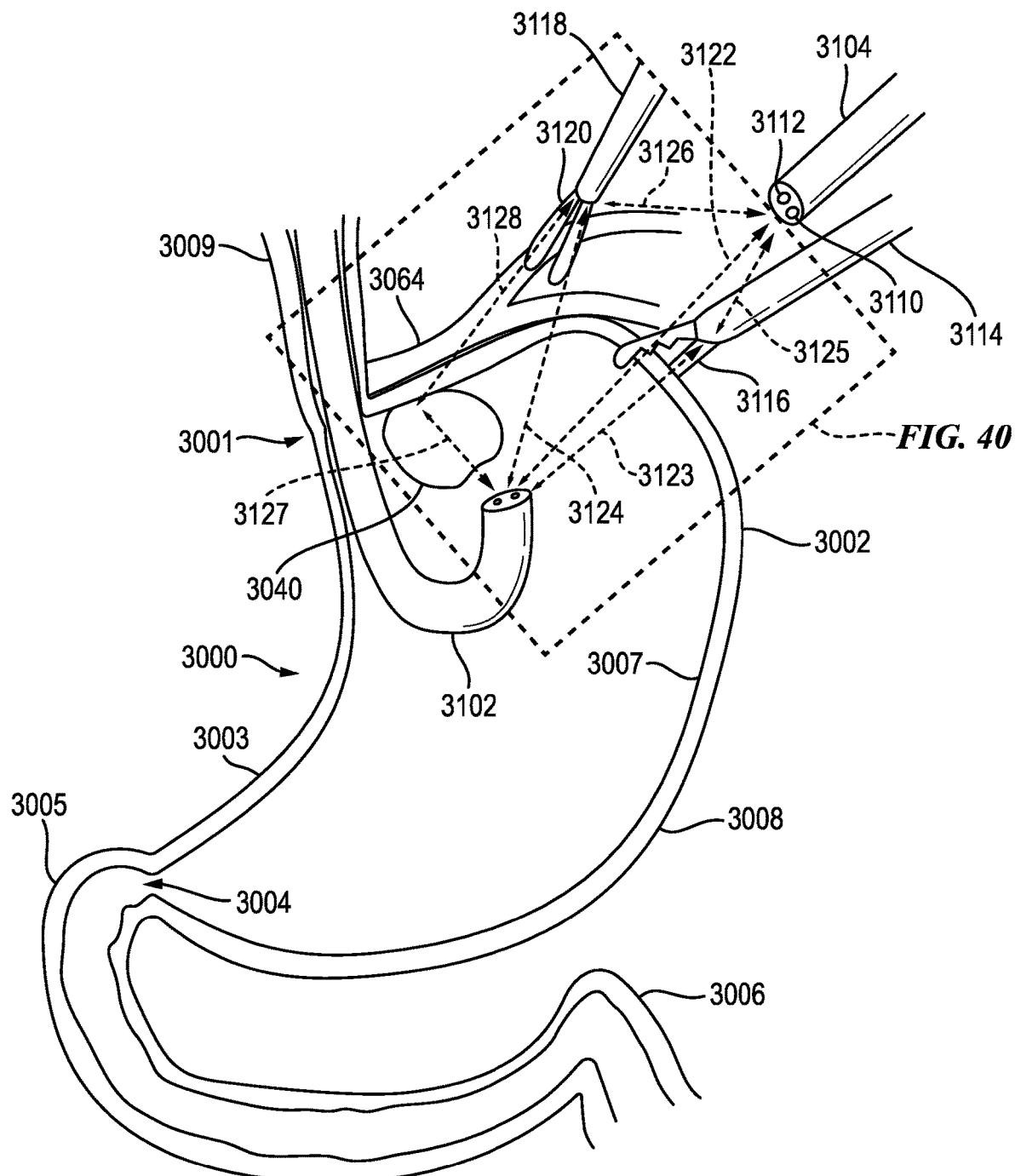
FIG. 38 is a schematic view of the surgical system of FIG. 37, showing the relative distances between the laparoscope, the laparoscopic instruments, the endoscope, and a tumor within the stomach.

As further shown in FIG. 37 and FIG. 38, the surgical system 3100 includes first and second surgical instruments 3114, 3118 that are each configured for laparoscopic access through the abdominal wall and into the extraluminal anatomical space surrounding the stomach 3000. The first and second surgical instruments 3114, 3118 can have a variety of configurations. For example, in this illustrated embodiment, the first and second surgical instruments 3114, 3118 each include a pair of jaws 3116, 3120, respectively, that are configured to manipulate the stomach 3000 from the laparoscopic side. While two surgical instruments 3114, 3118 are illustrated, in other embodiments, the surgical system 3100 can include one surgical instrument or more than two surgical instruments. In some embodiments, the first and second surgical instruments 3114, 3118 can be passed through ports of the same trocar and/or multi-port device that the laparoscope 3104 is positioned therethrough.

The surgical system 3100 also includes a controller 3130 communicatively coupled to the endoscope 3102 and the laparoscope 3104, and is configured to receive the transmitted image data of the first and second scenes from the first and second optical sensors 3106, 3110, respectively. The controller 3130 is also communicatively coupled to first and second tracking devices 3109, 3113 and is configured to receive the transmitted signals from the first and second tracking devices 3109, 3113, respectively. Once received, the controller 3130 is configured to determine at least the relative distance between the endoscope 3102 and the laparoscope 3104. In certain embodiments, the controller 3130 can also be configured to determine the relative orientation between endoscope 3102 and the laparoscope 3104.

As shown in FIG. 38, the relative distance between the endoscope 3102 and the laparoscope 3104 is illustrated in as dashed arrow 3122. Based on both the transmitted image data and the relative distance between endoscope 3102 and the laparoscope 3104, the controller 3130 is configured to provide a merged image to a display, for example, on a first display 3132, a second display 3134, or both of the surgical system 3100. In the merged image, at least one of the endoscope 3102 and the laparoscope 3104 is a representative depiction thereof.

The first and second displays 3132, 3134 can be configured in a variety of configurations. For example, in some embodiments, the first display can be configured to display the first scene and the second display can be configured to display the second scene, and the first display, the second display, or both, can be further configured to display the merged image. In another embodiment, the surgical system 3100 can include, a third display 3136 (FIG. 37) that can be used to display the merged image, and the first and second displays 3132, 3134 are used to only show the transmitted image data from the optical sensors 3106, 3110, respectively, without any modification. In this embodiment, a surgeon can access the real-time scenes from both the endoscope 3102 and the laparoscope 3104 on the first and second displays 3132, 3134, while also having access to the merged image on the third display 3136.

As stated above, the endoscope 3102 includes the first optical sensor 3106. The first optical sensor 3106 is configured to transmit image data of a first scene within a field of view of the endoscope 3102 to the controller 3130. In this illustrated embodiment, the tumor 3040 is arranged within the field of view of the endoscope 3102. As a result, the controller 3130, based on the transmitted image data can determine the relative distance between the endoscope 3102 and the tumor 3040. As shown in FIG. 38, the relative distance between the endoscope 3102 and the tumor 3040 is illustrated as dashed arrow 3127. In some embodiments, the relative distance 3127 can be determined by using structured light projected onto the tumor 3040 (e.g., via lighting element 3108) and tracked by the first optical sensor 3106. Further, in some embodiments, the controller 3130 based on the determined relative distances 3122 (between the endoscope 3102 and laparoscope 3104) and determined relative distance 3127 (between the endoscope 3102 and the tumor 3040), the controller can calculate the relative distance between the laparoscope 3104 and the tumor 3040.

Additionally, the laparoscope 3104 includes the second optical sensor 3110. The second optical sensor 3110 is configured to transmit image data of a second scene within a field of view of the laparoscope 3104 to the controller 3130. The first and second surgical instruments 3114, 3118 are arranged within the field of view of the laparoscope 3104. As a result, the controller 3130, based on the transmitted image data, can determine the relative distance between the laparoscope 3104 and each of the first and second surgical instruments 3114, 3118. In certain embodiments, the controller 3130 can also be configured to determine the relative orientation between the laparoscope 3104 and each of the first and second surgical instruments 3114, 3118.

As shown in FIG. 38, the relative distance between the laparoscope 3104 and the first surgical instrument 3114 is illustrated as dashed arrow 3125, and the relative distance between the laparoscope 3104 and the second surgical instrument 3118 is illustrated as dashed arrow 3126. In some embodiments, the relative distances 3125, 3126 can be determined by using structured light projected onto the surgical instruments 3114, 3118 (e.g., by lighting element 3112) and tracked by the second optical sensor 3110.

Based on the relative distance 3122 (between the endoscope 3102 and laparoscope 3104), the relative distance 3125 (between the laparoscope 3104 and the first surgical instrument 3114), 3126 (between the laparoscope 3104 and the second surgical instrument 3118), 3127 (between the endoscope 3102 and the tumor 3040), the controller 3130 can determine, for example, the relative distance between the endoscope 3102 and each of the first surgical instrument 3114 and the second surgical instrument 3118, the relative distance between the tumor 3040 and each of the first instrument 3114 and the second instrument 3118, etc. As shown in FIG. 38, the relative distance from the endoscope 3102 to the first surgical instrument 3114 is illustrated as dashed arrow 3123, the relative distance from the endoscope 3102 to the second surgical instrument 3118 is illustrated as dashed arrow 3124, and the relative distance from the tumor 3040 to the surgical second instrument 3118 is illustrated as dashed arrow 3128. Based on the determined relative distances 3123, 3124, 3128, and the transmitted image data (e.g., of the first scene, the second scene, or both), the controller can create a merged image that is projected onto the first display 3132, the second display 3134, or both. Since there is direct imaging of each of the instruments sets from their respective cameras, and because the system is able to determine the exact type of devices in use (e.g., graspers, cutters) since the instruments have been scanned into or identified in some form to the surgical hub to allow setup of the system for interaction with the devices, the system can create a 3D model recreation of each of the instruments. With the relative distances measured or at least one coupled 3D axis registration, the system could display the devices from the occluded camera and invert them in the necessary manner to show their location, orientation and status in real-time. These 3D models could even be modified with details directly imaged from the camera viewing the occluded cooperative image.

Further, in certain embodiments, the controller can also determine relative orientations between the endoscope 3102 and the laparoscope 3104, the first instrument 3114 and/or the second instrument 3118 relative to the endoscope 3102 and/or relative to the tumor 3040, etc. Based on the determined relative orientations and the transmitted image data (e.g., of the first scene, the second scene, or both), the merged image can also illustrate not only the locations, but also the orientations of one or more of the endoscope 3102, the laparoscope 3104, the first surgical instrument 3114, the second surgical instrument 3118, and the tumor 3040. As discussed above, the means to create a completely generated 3D model of the instrument that can be overlaid into the image of the system which cannot see the alternative view. Since the representative depiction is a generated image, various properties of the image (e.g., the transparency, color) can also be manipulated to allow the system to be clearly shown as not within the real-time visualization video feed, but as a construct from the other view. If the user where to switch between imaging systems, the opposite view could also have the constructed instruments within its field of view. In some embodiments, there is another way to generate these overlays. The obstructed image could isolate the instruments in its stream from the surrounding anatomy, invert and align the image to the known common axis point and then merely overlay a live image of the obstructed view into the non-obstructed view camera display feed. Like the other representative depiction above, the alternative overlay could be shaded, semi-transparent, or otherwise modified to insure the user can tell the directly imaged view from the overlaid view in order to reduce confusion. This could be done with key aspects of the anatomy as well (e.g., the tumor that can be seen by one camera but not the other). The system could utilize the common reference between the cameras and display the landmark, point of interest, or key surgical anatomy aspect and even highlight it to allow for better approaches and interaction even from the occluded approach of the key aspect.

Figure 39:
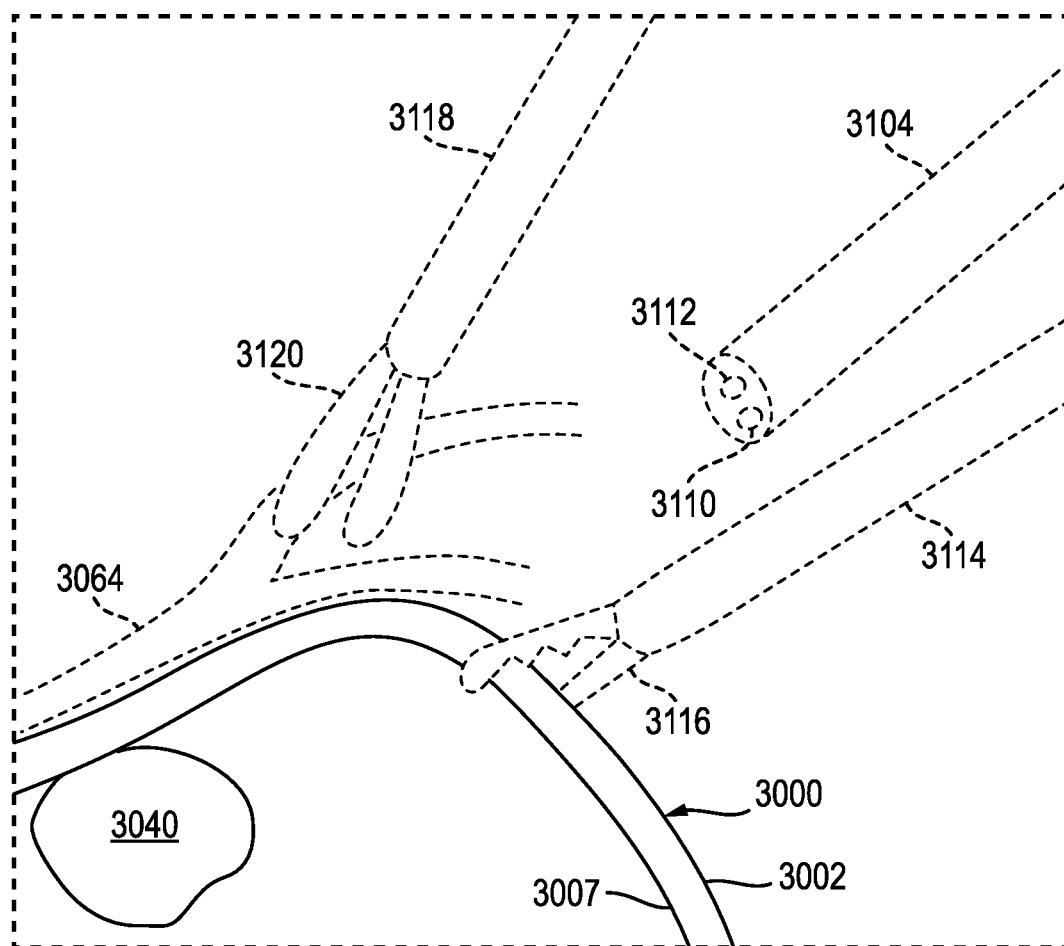
FIG. 39 is a schematic view of a merged image of the surgical system of FIG. 37 from the perspective of the endoscope.

FIG. 39 illustrates an exemplary embodiment of a merged image. The merged image illustrates a real-time first scene within the field of view of the endoscope 3102 with an overlaid representative depiction of a portion of the laparoscopic side of the stomach (e.g., the blood vessels 3064, the laparoscope 3104, and/or the surgical first and second instruments 3114, 3118). A person skilled in the art will understand that the phrase "representative depiction" as used herein refers to a virtual overlay on an actual depiction from a camera, where the virtual overlay corresponds to the location and orientation of objects which are arranged within the field of view of a camera, but not visible to the camera due to an obstacle being arranged between the camera and the objects, and that the phrase "actual depiction" as used herein refers to an unmodified, real-time image or video stream from a camera. Based on the transmitted image data of the first scene in combination with the determined relative distances 3122, 3123, 3124, the controller 3130 can provide the merged image from the point of view of the endoscope 3102, where the laparoscope 3104 and the surgical instruments 3114, 3118 are shown as representative depictions which correspond to their location in the extraluminal space in real-time. In the illustrated embodiment, the representative depictions are shown in dashed outlines of the corresponding blood vessels 3064, laparoscope 3104, and surgical instruments 3114, 3118. However, other forms of representative depictions can be used, such as simple geometric shapes to represent the non-visual instruments and anatomical structures within the intraluminal space.

Figure 40:
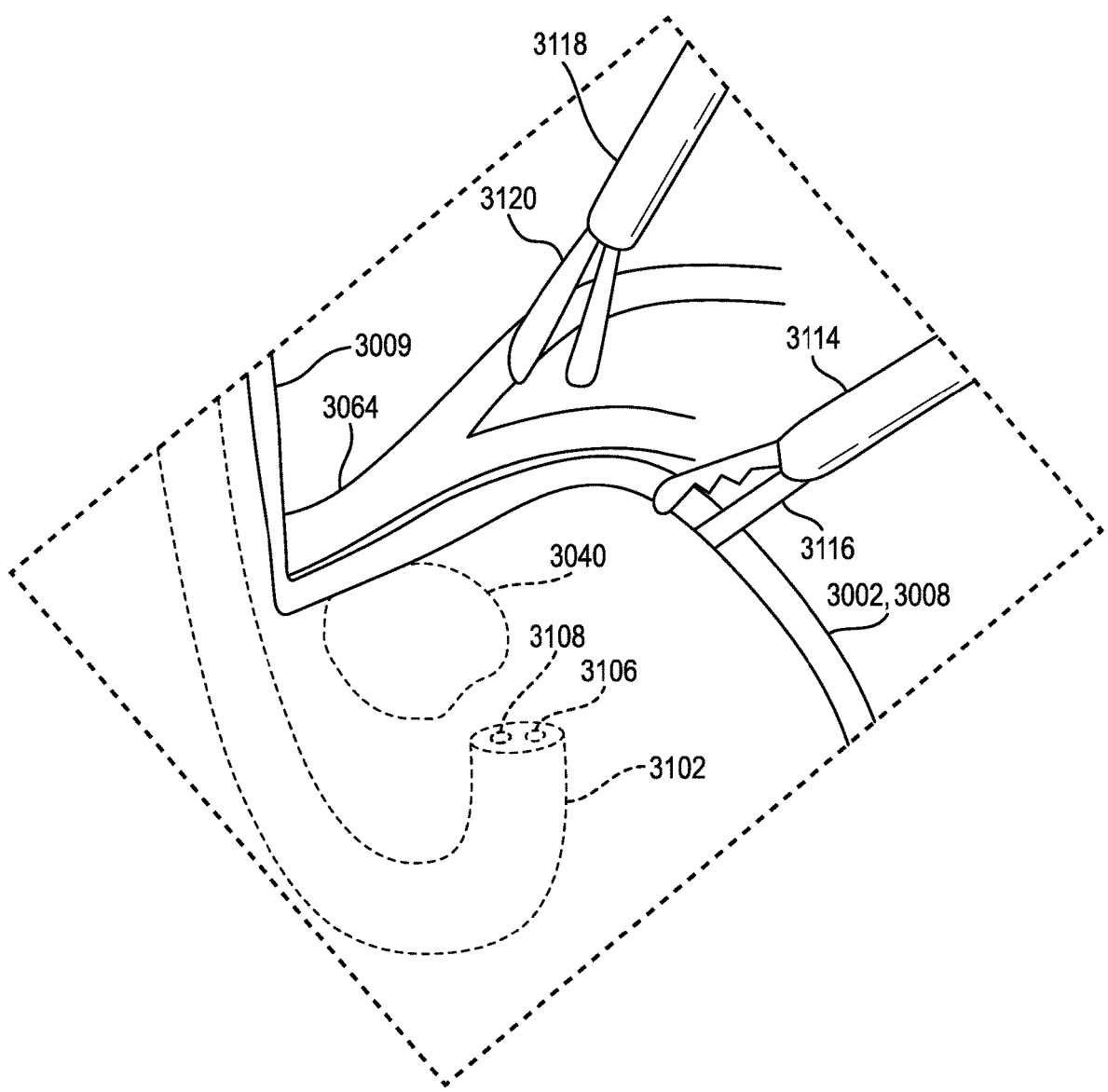
FIG. 40 is a schematic view of a merged image of the surgical system of FIG. 38 from the perspective of the laparoscope.

Alternatively, or in addition, the controller 3130 can generate a merged image from the perspective of the laparoscope 3104. For example, in FIG. 40, the merged image illustrates a the real-time second scene within the field of view of the laparoscope 3104 and an overlaid representative depiction of a portion of the endoscopic side of the stomach (e.g., the tumor 3040 and/or the endoscope 3102). Based on the transmitted image data of the second scene in combination with the determined, the controller 3130 can provide the merged image from the point of view of the laparoscope 3104, where the endoscope 3102 and the tumor 3040 are shown as representative depictions which correspond to their location in the intraluminal space in real-time. In the illustrated embodiment, the representative depictions are shown in dashed outlines of the corresponding tumor 3040 and endoscope 3102. However, other forms of representative depictions can be used, such as simple geometric shapes to represent the non-visual instruments and anatomical structures within the intraluminal space.

In some embodiments, monitoring of interior and exterior portions of interconnected surgical instruments can be performed in order to be image both the internal and external interactions of the surgical instruments with adjacent surgical instruments. In certain embodiments, the surgical instruments that include an articulation actuation system outside of the body. Additionally, the surgical instruments can be configured to be coupled to electromechanical arms of a robotic system. A tracking device can be used to ensure that robotic arms of different instruments do not contact one another outside of the body even though the internal instruments may not be contacting. This system can be used to control intended and prevent inadvertent interactions of laparoscopically arranged instruments by monitoring intracorporeal and extracorporeal aspects of the same instruments.

In other embodiments, the coordination of interior and exterior views of portions of surgical instruments can be accomplished by two separate imaging systems. This would enable the monitoring of the external interactions of multiple surgical instruments while controlling and tracking the internal interactions of those same surgical instruments. The system can minimize unintended external interactions between the surgical instruments while improving the internal operation envelop of the same surgical instruments.

Instrument Control Imaging Systems for Visualization of Upcoming Surgical Procedure Steps Devices, systems, and methods for multi-source imaging provided herein allow for cooperative surgical visualization that enable instrument coordination of the instruments based on a procedure plan for a specific operation. In general, the present surgical systems provide images of both the intraluminal anatomical space and the extraluminal anatomical space, and based on these images, provide a merged image in which certain surgical steps that are performed endoscopically can be coordinated with a known surgical site in a subsequent step performed laparoscopically, or vice versa.

For a surgical procedure, there is a corresponding procedure plan which a surgeon follows as the surgery progresses. The steps in a procedure plan can be performed in a linear fashion in order to achieve a desired outcome, such as removing a tumor from a stomach. Through the procedure plan, several steps are known in advance: (i) the tumor must be partially resected from the inner tissue wall of the stomach; (ii) the stomach must be flipped in order to access the tumor from the laparoscopic side in order to maintain the stomach in an upright orientation to prevent stomach acid from spilling out; and (iii) an incision must be made laparoscopically in order to access the tumor. These pieces of information suggest that two different incisions must be made on the stomach, one to partially remove the tumor, and one to create an opening in the stomach wall to access the tumor. Based on this knowledge that two separate incisions must be made in relatively the same location, an algorithm can calculate where the first and second incisions should be located to align the second incision with the first incision so that the incisions are as small as possible and efficiently made.

In one exemplary embodiment, the surgical systems can include an energy applying surgical instrument configured to apply energy to a natural body lumen or organ, a first scope device configured to transmit image data of a first scene within its field of view, a second scope device configured to transmit image data of a second scene within its field of view, and a controller configured to receive the transmitted image data of the first and second scenes and to provide a merged image of the first and second scenes. As a result, the merged image provides two separate points of view of the surgical site which allows a medical practitioner to coordinate a location of energy to be applied to an inner surface of a tissue wall at the surgical site relative to an intended interaction location of a second instrument on an outer surface of the tissue wall in a subsequent procedure step at the surgical site.

The controller is configured to generate a merged image of the first and second scenes. The controller receives the actual depiction from each of the first imaging system and second imaging system. The actual depiction can be a photo or a live video feed of what each of the imaging systems, which are attached to each of the scope devices, are seeing in real time. Each of the first and second scenes depict certain critical structures which are not visible by the other imaging system. For example, the first imaging system, arranged endoscopically can have a tumor and an energy applying surgical instrument within its field of view. Additionally, the second imaging system can include laparoscopic instruments arranged within its field of view. Further, as will be discussed in more detail, the merged image facilitates coordination of a location of energy to be applied by the energy applying surgical instrument to an inner surface of a tissue wall at a surgical site relative to an intended interaction location of a second instrument on an outer surface of the tissue wall in a subsequent procedure step at the surgical site.

In some embodiments, the system would need to couple "known" points. These known points would likely be either fixed aspects (e.g., instrument or scope features, since they are on rigid and predictable systems) or linked anatomic landmarks (e.g., a known anatomic sphincter, ligament, artery that can be seen from both systems directly). The tumor is likely visible or partially visible in one of imaging systems. In hollow organ surgeries, the tissue walls are usually thin and the tumors superficial to at least one side of the organ. An example would be lung cancer. In lung cancer the tumor would be present in either the dissected parenchyma (i.e. from the lap side) or in the bronchial wall (i.e. from the endoscopic approach). Then the system would only need to identify one scope with respect to the other in 3D space or identify an anatomic landmark that both scope can see from different points of view in order to overly the tumor from the side that can see it to the imaging system that cannot.

The first scope device is configured to be at least partially disposed within at least one of a natural body lumen and an organ (e.g., a lung, a stomach, a colon, or small intestines), and the second scope device is configured to be at least partially disposed outside of the at least one of the natural body lumen and the organ. In certain embodiments, the first scope device is endoscope and the second scope device is a laparoscope. The natural body lumen or organ can be any suitable natural body lumen or organ. Non-limiting examples include a stomach, a lung, a colon, or small intestines.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with a stomach, a person skilled in the art will appreciate that these surgical systems can be used in connection with any other suitable natural body lumens or organs.

Figure 41:
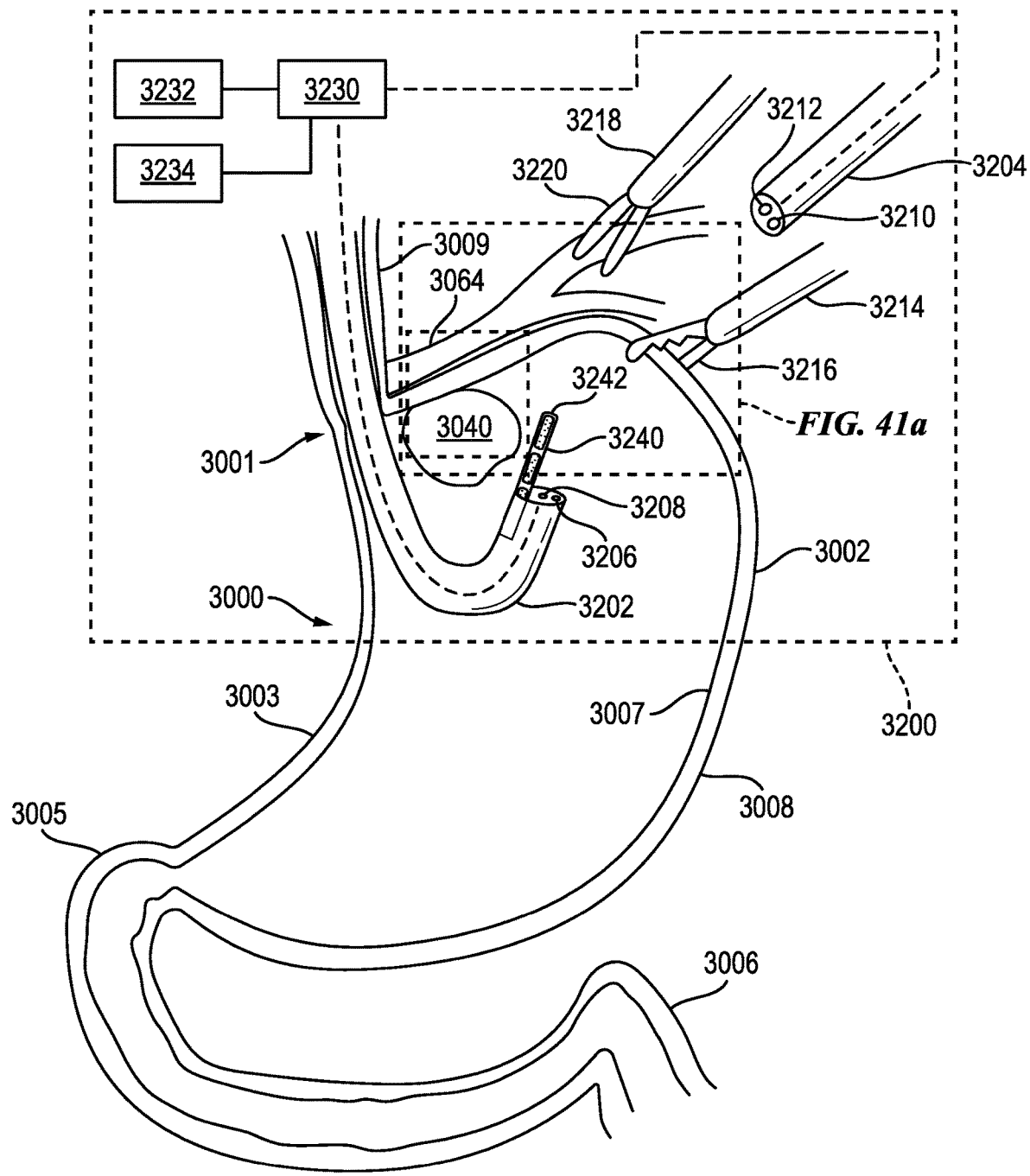
FIG. 41 is a schematic view of the surgical system of FIG. 40, showing a partial removal of a tumor arranged within the stomach by an endoscopically arranged instrument.
Figure 42:
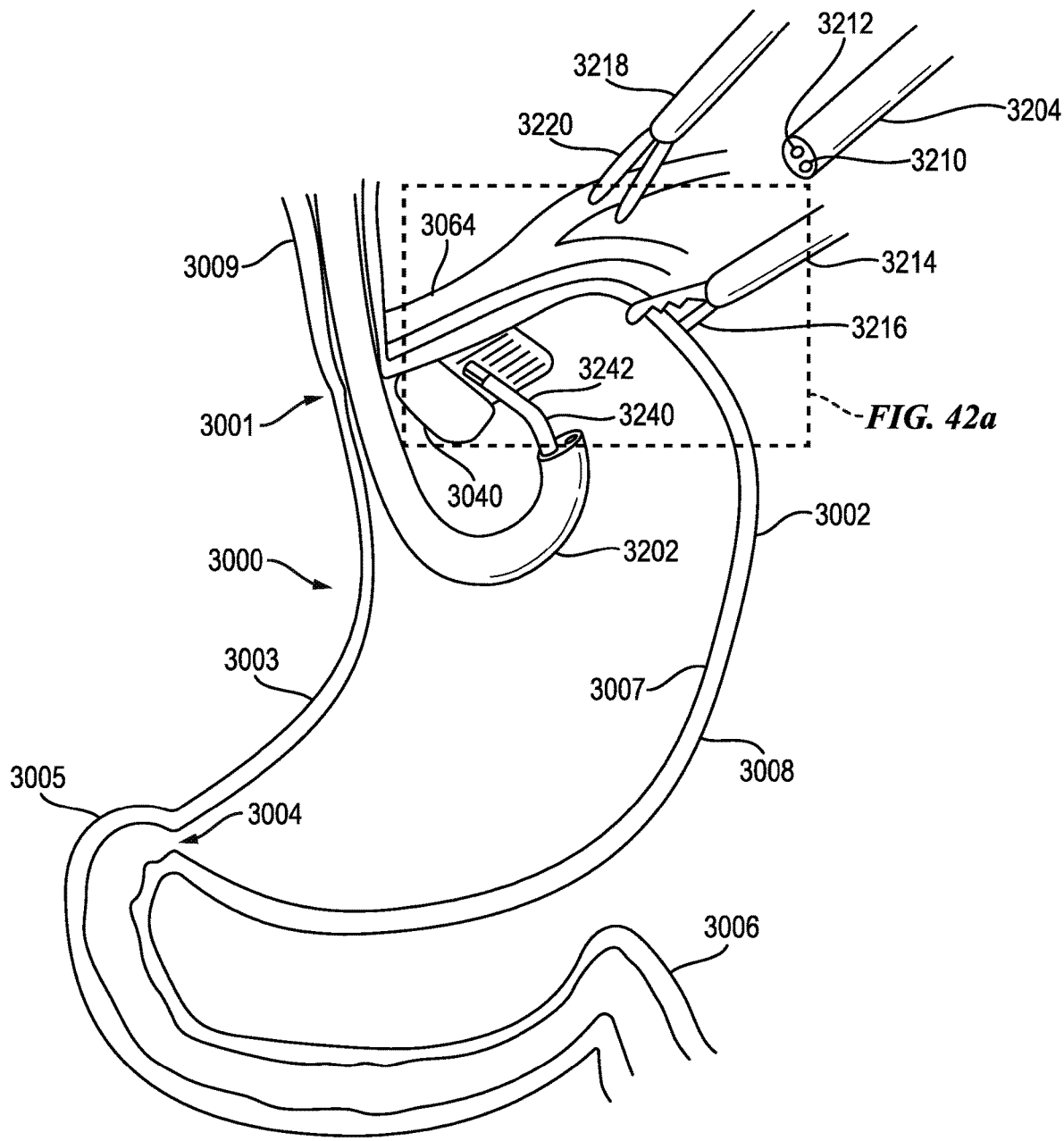
FIG. 42 is a schematic view of the surgical system of FIG. 41, showing the partial removal of a tumor from an inner tissue wall of a stomach.

FIG. 41 and FIG. 42 illustrate an exemplary embodiment of a surgical system 3100 that is configured for endoluminal access into and laparoscopic access of the stomach 3000. Aside from the differences described in detail below, the surgical system 3200 can be similar to surgical system 3100 (FIG. 37 and FIG. 38) and therefore common features are not described in detail herein. For purposes of simplicity, certain components of the surgical system 3200 and the stomach 3000 are not illustrated.

As shown, the stomach 3000 includes an esophageal sphincter 3001, a greater curvature 3002, a lesser curvature 3003, a pyloric sphincter 3004, a duodenum 3005, and a duodenojejunal flexure 3006. Additionally, the stomach includes an inner tissue wall 3007, and an outer tissue wall 3008. As illustrated, the stomach 3000 includes a tumor 3040 arranged on the greater curvature 3002. When operating on the stomach 3000, the blood vessels 3064 may need to be manipulated (e.g., mobilized) using laparoscopically arranged instruments in order to properly access the tumor 3040. In use, as described in more detail below, the surgical system 3200 can provide a merged image so that energy application and incisions in subsequent procedure steps can be coordinated and visualized.

The surgical system 3200 includes an endoscope 3202 configured for endoluminal access through the esophagus 3009 and into the stomach 3000. The endoscope 3202 can have a variety of configurations. For example, in this illustrated embodiment, the endoscope 3202 includes an optical sensor 3206 (e.g., a camera) and light element 3208. Further, the endoscope 3202 includes a working channel 3203 that is arranged along the length of the endoscope 3202. The working channel 3203 is configured to receive one or more surgical instruments and/or allow fluid to pass therethrough to insufflate a lumen or organ (e.g., the stomach). In some embodiments, the endoscope 3202 can include an outer sleeve (not shown) configured to be inserted through a patient's mouth (not shown) and down the esophagus 3009. The outer sleeve can include a working channel that is configured to allow the endoscope 3202 to be inserted through the outer sleeve and access the stomach 3000.

The surgical system 3200 also includes a laparoscope 3204 configured for laparoscopic access through the abdominal wall (not shown) and into the extraluminal anatomical space adjacent to the stomach 3000. The laparoscope 3204 can have a variety of configurations. For example, in this illustrated embodiment, the laparoscope 3204 includes an optical sensor 3210 (e.g., a camera) and lighting element 3212. Alternatively, or in addition, the laparoscope 3204 can include a working channel (not shown) arranged along the length of the laparoscope 3204 to pass an instrument laparoscopically into the extraluminal anatomical space. In some embodiments, the laparoscope 3204 can be inserted into the extraluminal anatomical space through a trocar or multi-port (not shown) positioned within and through a tissue wall. The trocar or multi-port can include ports for passing the laparoscope 3204 and/or other surgical instruments into the extraluminal anatomical space to access the stomach 3000.

As shown in FIG. 41 and FIG. 42, the surgical system 3200 includes an energy applying surgical instrument 3240 that passes through the working channel 3203 of the endoscope 3202 and into the stomach 3000. While the energy applying surgical instrument can have a variety of configurations, in this illustrated embodiment, the energy applying surgical instrument 3240 includes a blade 3242 at a distal end thereof. The blade 3242 can have a variety of configurations. For example, in some embodiments, the blade can be in the form of mono-polar RF blade or an ultrasonic blade. Exemplary embodiments of energy applying surgical instruments that can be used with the present systems are further described in U.S. Pat. No. 10,856,928, which is incorporated herein by reference in its entirety. A GEM blade is a Megadyne smart monopolar blade. It is an advanced monopolar blade capable of sensing the tissue and apply the appropriate RF energy need for the task, just like advanced bipolar or the smart ultrasonic controls. A person skilled in the art will appreciate that the type of surgical instrument and the structural configuration of the surgical instrument, including the end effector, depends at least upon the surgical site and the surgical procedure to be performed.

As further shown in FIG. 41, the energy applying surgical instrument 3202 includes a force sensor 3209 (e.g., the force sensor 3209 can be coupled to one or more motors (not shown) of the instrument 3202 or of a robotic arm (not shown) that is coupled to the instrument 3202). During use, the force sensor 3209 is configured to sense the amount of force being applied by the blade 3242 to the tissue of the stomach 3000 as the blade 3242 moves (e.g., cuts) through the tissue. The force sensor 3209 is further configured to transmit the force data to a controller 3230 of the surgical system 3200. The controller 3230 can aggregate the received feedback input(s) (e.g., force data), perform any necessary calculations, and provide output data to effect any adjustments that may need to be made (e.g., adjust power level, advancement velocity, etc.). Additional details on the force sensor 3209 and controller 3230 are further described in previously mentioned U.S. Pat. No. 10,856,928, which is incorporated herein by reference in its entirety. In some embodiments, the force sensor 3209 can be omitted.

Alternatively, or in addition, the controller 3230 is configured to calculate an insertion depth of the blade 3242 of the energy applying surgical instrument 3240 within tissue of the stomach 30 based on the transmitted image data from either the endoscope 3202 and/or the laparoscope 3204. For example, during endoscopic dissection of the stomach wall, the optical sensor 3206 of the laparoscope 3204 can monitor the dissection site from outside the stomach. Based on this image data that is transmitted to the controller 3230, the controller 3230 can determine the depth of the blade 3242. This can prevent inadvertent full thickness penetration which can result in a leak. Further, the laparoscope 3204 can also monitor heat (via IR wavelength) and collateral thermal damage (tissue refractivity & composition) of the stomach at the dissection site where the energy applying surgical instrument is active. This laparoscopic thermal and welding monitoring can be used to further prevent unnecessary damage to the stomach tissue (e.g., help trigger power adjustments to the energy applying surgical instrument). Various embodiments of thermal and welding monitoring in surgical systems to prevent unnecessary damage to tissue are discussed further, for example, in U.S. Pat. App No. 63/249,658 entitled "Surgical Devices, Systems, And Methods For Control Of One Visualization With Another" filed on Sep. 29, 2021.

The surgical system 3200 includes first and second surgical instruments 3214, 3218 that are each configured for laparoscopic access through the abdominal wall and into the extraluminal anatomical space surrounding the stomach 3000. The first and second surgical instruments 3114, 3118 can have a variety of configurations. For example, in this illustrated embodiment, the first and second surgical instruments 3114, 3118 each include a pair of jaws 3116, 3120, respectively, that are configured to manipulate the stomach 3000 from the laparoscopic side. While two surgical instruments 3114, 3118 are illustrated, in other embodiments, the surgical system 3100 can include one surgical instrument or more than two surgical instruments. In some embodiments, the first and second surgical instruments 3114, 3118 can be passed through ports of the same trocar and/or multi-port device that the laparoscope 3104 is positioned therethrough.

As stated above, the endoscope 3202 includes the first optical sensor 3206. The first optical sensor 3106 is configured to transmit image data of a first scene within a field of view of the endoscope 3102 to the controller 3130. In this illustrated embodiment, the tumor 3040 is arranged within the field of view of the endoscope 3102. As shown in FIG. 41, the energy applying surgical instrument 3240 is inserted into the working channel of the endoscope 3202 and the blade 3242 is advanced towards the tumor 3040. In conventional surgical systems, a surgeon would partially remove the tumor 3040 using the blade 3242 based on the endoscopic scene only, and then proceed to perform a partial stomach flip blindly (e.g., using only the laparoscopic scene) to remove the tumor 3040 laparoscopically through an incision in the stomach wall. The surgeon is not able to coordinate the endoscopic and laparoscopic incisions accurately, and instead approximates where the tumor is during the stomach flip, which could lead to inaccurate incisions which remove more tissue than required. However, in the present system 3200, since both the endoscope 3202 and laparoscope 3204 can provide image data of the surgical site from both the intraluminal anatomical space and the extraluminal anatomical space, the dissection margin (e.g., where the energy applying surgical instrument 3240 is going to apply energy to partially remove the tumor) can be coordinated with a second incision (e.g., where a laparoscopic cut will be made in a subsequent procedure step to remove or detach the tumor 3240 from the stomach.)

The surgical system 3200 also includes a controller 3230 communicatively coupled to the endoscope 3202 and the laparoscope 3204. The controller 3230 is configured to receive the transmitted image data of the first and second scenes from the first and second optical sensors 3206, 3210 and provide a merged image of first and second scenes. This merged image facilitates coordination of a location of energy to be applied by the energy applying surgical instrument 3240 to the inner tissue wall 3057 of the stomach at the surgical site 3245 relative to an intended interaction location of a second instrument (e.g., cutting instrument 3248 having end effectors 3250 in FIG. 43) on the outer tissue wall 3058 of the stomach in a subsequent procedure step at the surgical site 3245.

The controller 3230 is configured to provide a merged image to a display, for example, on a first display 3232, a second display 3234, or both of the surgical system 3200. The first and second displays 3232, 3234 can be configured in a variety of configurations. For example, in some embodiments, the first display can be configured to display the first scene and the second display can be configured to display the second scene, and the first display, the second display, or both, can be further configured to display the merged image. In another embodiment, the surgical system 3200 can include, a third display that can be used to display the merged image, and the first and second displays 3232, 3234 are used to only show the transmitted image data from the first and second optical sensors 3206, 3210, respectively, without any modification. In this embodiment, a surgeon can access the real-time scenes from both the endoscope 3202 and the laparoscope 3204 on the first and second displays 3232, 3234, while also having access to the merged image on the third display 3236.

Figure 41A:
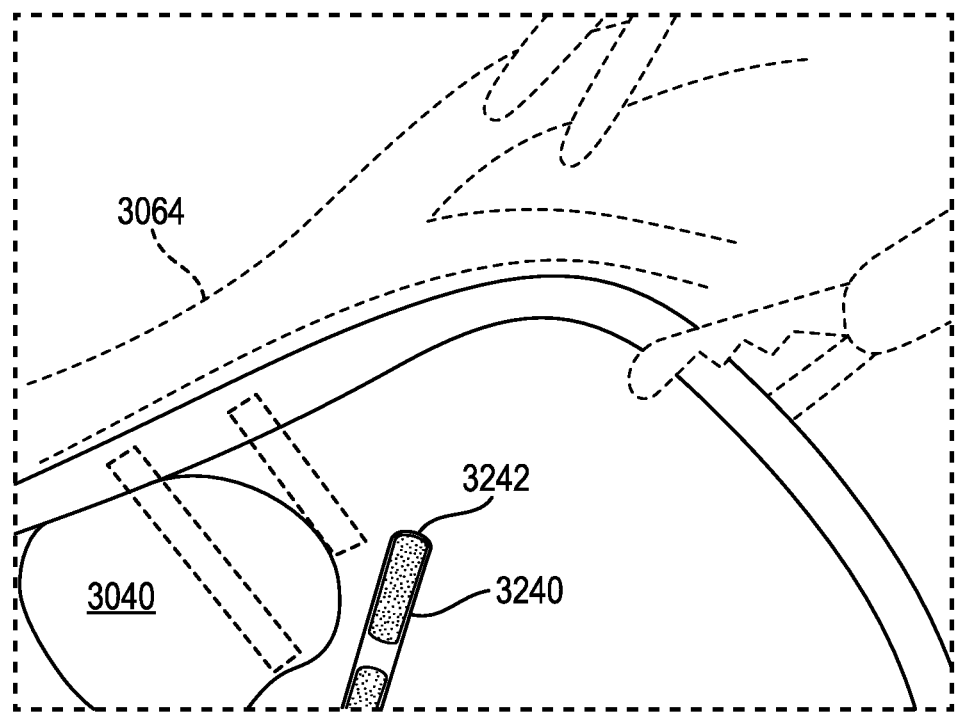
FIG. 41a is a schematic view of a merged image of the surgical system of FIG. 41 from the perspective of the endoscope.

As illustrated in FIG. 41a, the display 3232 depicts the scene from the endoscope 3202, where the optical sensor 3206 has the tumor 3040, energy applying surgical instrument 3240, and the blade 3242 in its field of view. Based on subsequent steps of the procedure plan, the controller 3230 can provide a merged image, where a first interaction location 3244, including a start location 3244a and an end location 3244b, is depicted in relation to the tumor 3040 as a representation of the intended interaction locations of the energy applying surgical instrument 3240. The start location 3244a corresponds to a start point of an incision to partially remove the tumor 3040 from the internal tissue wall 3007 of the stomach 3000, and the end location 3244b corresponds to an end point of the incision initiated at the start location 3244a. As such, a surgeon would be able to visualize where an incision should start and end, based on subsequent procedure steps. In some embodiments, one or more of the subsequent steps are based on the procedure plan. In certain embodiments, one or more of the subsequent procedure steps can be an adjusted based on the actual surgical steps relative to the procedure plan that have already been performed (e.g., GPS map destination directions recalculated based on user actions during the surgical procedure). In some embodiments, the blood vessels 3064 and surgical instruments 3216, 3220 can be shown in the merged image as representative depictions, similar to the merged images of FIG. 39.

Figure 42A:
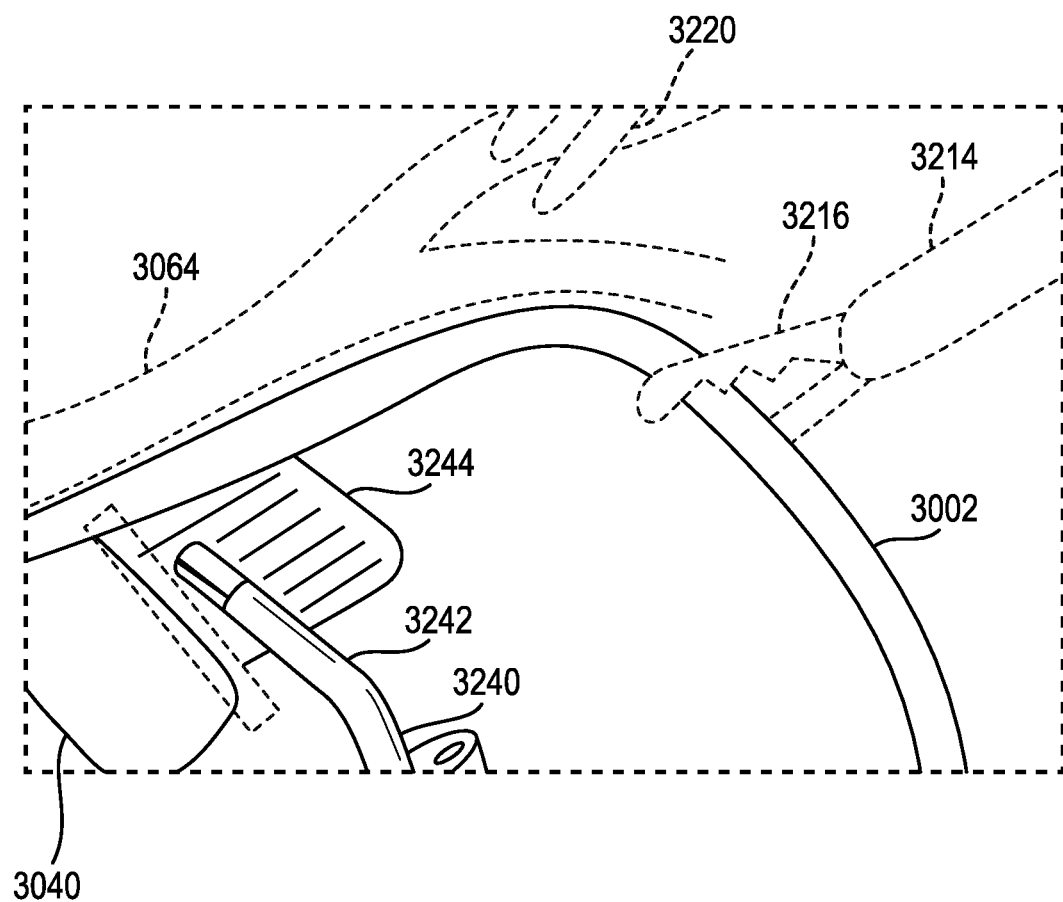
FIG. 42a is a schematic view of a merged image of the surgical system of FIG. 42 from the perspective of the endoscope.

As illustrated in FIG. 42, after energy applying surgical instrument is used to partially remove the tumor 3040 from the inner tissue wall 3007 of the stomach by applying the blade 3242 to the tissue surrounding the tumor 3040. As illustrated in FIG. 42a, the blade 3242 traverses from the first interaction location 3244a to the second interaction location 3244b. Once the blade 3242 has reached the second interaction location 3244b, the energy application is terminated as to not fully remove the tumor 3040 from the inner tissue wall 3007.

As stated above, the surgical system 3200 also includes a controller 3230 communicatively coupled to the endoscope 3202 and the laparoscope 3204, and is configured to receive the transmitted image data of the first and second scenes from the first and second optical sensors 3206, 3210, respectively. The controller 3230 is also communicatively coupled to first and second tracking devices 3252, 3254 arranged within the endoscope and laparoscope, similar to tracking device 3109, 3113, and is configured to receive the transmitted signals from the first and second tracking devices, respectively. Once received, the controller 3230 is configured to determine at least the relative distance between the endoscope 3202 and the laparoscope 3204. In certain embodiments, the controller 3230 can also be configured to determine the relative orientation between endoscope 3202 and the laparoscope 3204.

In some embodiments, the first and second tracking devices 3252, 3254 are configured to use magnetic or radio frequency sensing to detect a location, an orientation, or both of the endoscope 3202 and laparoscope 3204, respectively (e.g., when the endoscope 3202 and laparoscope 3204 positioned on opposite sides of the tissue wall of the stomach 3000). Alternatively, the first and second tracking devices 3252, 3254 are configured to use common anatomic landmarks to detect a location, an orientation, or both of the endoscope 3202 and laparoscope 3204, respectively (e.g., when the endoscope 3202 and laparoscope 3204 positioned on opposite sides of the tissue wall of the stomach 3000). The first and second tracking devices 3252, 3254 can each transmit the signal(s) to a controller (like controller 3230). Various embodiments of magnetic fiducial markers and using magnetic fiducial markers in detecting location are discussed further, for example, in U.S. Pat. App No. 63/249,658 entitled "Surgical Devices, Systems, And Methods For Control Of One Visualization With Another" filed on Sep. 29, 2021.

Figure 43:
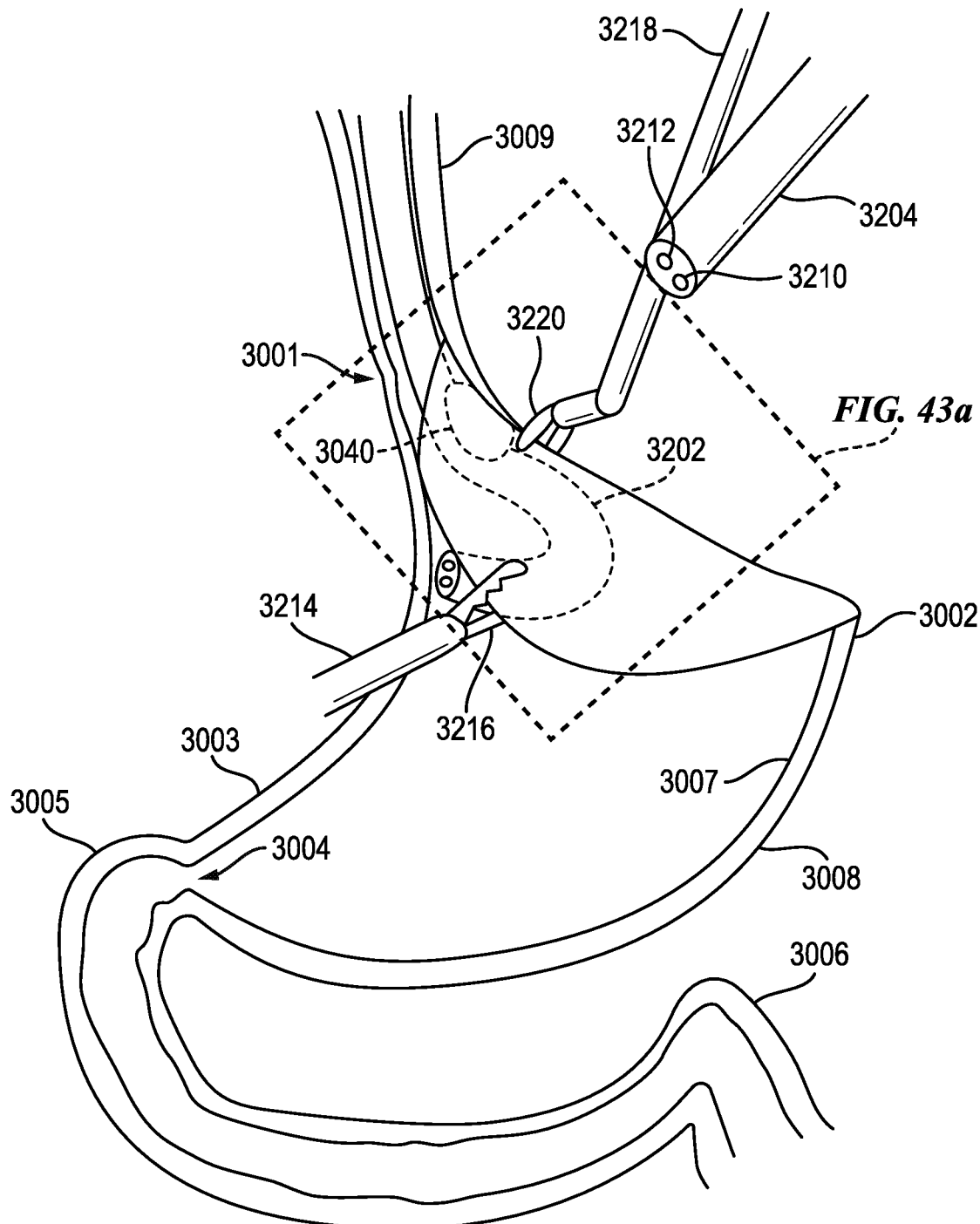
FIG. 43 is a schematic view of the surgical system of FIG. 42, showing mobilization of an upper portion of the stomach by the laparoscopically arranged instrument.

As shown in FIG. 43, the relative distance between the endoscope 3202 and the laparoscope 3204 is illustrated in as dashed arrow 3222. Based on both the transmitted image data and the relative distance between endoscope 3202 and the laparoscope 3204, the controller 3230 is configured to provide a merged image to a display, for example, on a first display 3232, a second display 3234, or both of the surgical system 3200. In the merged image, at least one of the endoscope 3202 and the laparoscope 3204 is a representative depiction thereof.

As stated above, the endoscope 3202 includes the first optical sensor 3206. The first optical sensor 3206 is configured to transmit image data of a first scene within a field of view of the endoscope 3202 to the controller 3230. In this illustrated embodiment, the tumor 3040 is arranged within the field of view of the endoscope 3202. As a result, the controller 3230, based on the transmitted image data can determine the relative distance between the endoscope 3202 and the tumor 3040. As shown in FIG. 43, the relative distance between the endoscope 3202 and the tumor 3040 is illustrated as dashed arrow 3227. In some embodiments, the relative distance 3227 can be determined by using structured light projected onto the tumor 3040 (e.g., via lighting element 3208) and tracked by the first optical sensor 3206. Further, in some embodiments, the controller 3230, based on the determined relative distances 3222 (between the endoscope 3202 and laparoscope 3204) and determined relative distance 3227 (between the endoscope 3202 and the tumor 3040), the controller can calculate the relative distance between the laparoscope 3204 and the tumor 3040.

Additionally, the laparoscope 3204 includes the second optical sensor 3210. The second optical sensor 3210 is configured to transmit image data of a second scene within a field of view of the laparoscope 3204 to the controller 3230. The cutting instrument 3248 is arranged within the field of view of the laparoscope 3204. As a result, the controller 3230, based on the transmitted image data, can determine the relative distance between the laparoscope 3204 and the cutting instrument 3248. In certain embodiments, the controller 3230 can also be configured to determine the relative orientation between the laparoscope 3204 and the cutting instrument 3248.

As shown in FIG. 43, the relative distance between the laparoscope 3204 and the cutting instrument 3248 is illustrated as dashed arrow 3225. In some embodiments, the relative distances 3225 can be determined by using structured light projected onto the cutting instrument 3248 (e.g., by lighting element 3212) and tracked by the second optical sensor 3210.

Based on the relative distance 3222 (between the endoscope 3202 and laparoscope 3204), the relative distance 3225 (between the laparoscope 3204 and the cutting instrument 3248), and the relative distance 3227 (between the endoscope 3202 and the tumor 3040), the controller 3230 can determine, for example, the relative distance between the tumor 3040 and cutting instrument 3248 and the cutting plane of the cutting instrument 3248. As shown in FIG. 43, the relative distance from the tumor 3040 to the cutting instrument 3248 is illustrated as dashed arrow 3223. Based on the determined relative distances 3223, and the transmitted image data (e.g., of the first scene, the second scene, or both), the controller can create a merged image that is projected onto the first display 3232, the second display 3234, or both. Since there is direct imaging of each of the instruments sets from their respective cameras, and because the system is able to determine the exact type of devices in use (e.g., graspers, cutters) since the instruments have been scanned into or identified in some form to the surgical hub to allow setup of the system for interaction with the devices, the system can create a 3D model recreation of each of the instruments. With the relative distances measured or at least one coupled 3D axis registration, the system could display the devices from the occluded camera and invert them in the necessary manner to show their location, orientation and status in real-time. These 3D models could even be modified with details directly imaged from the camera viewing the occluded cooperative image.

Figure 43A:
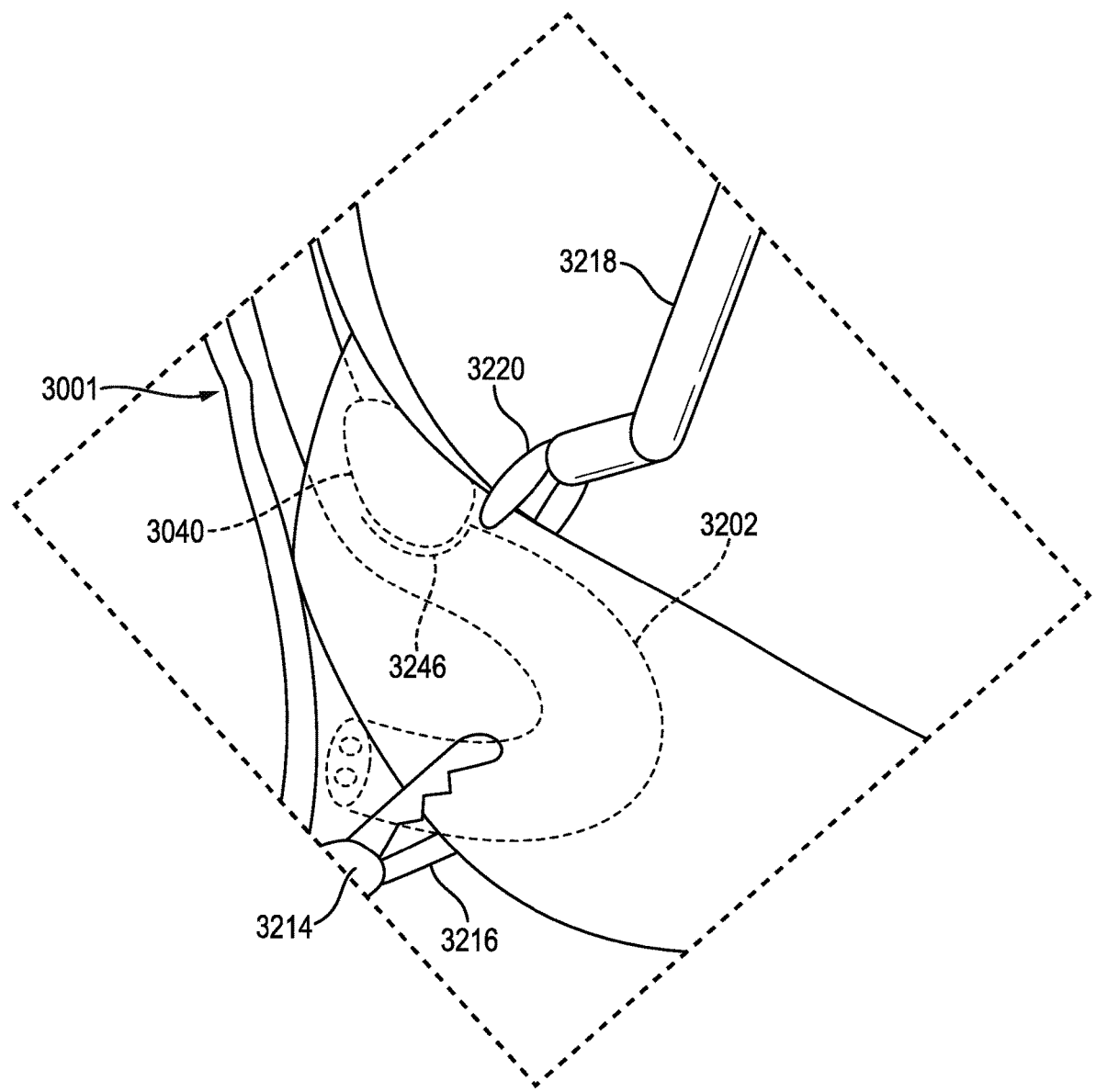
FIG. 43a is a schematic view of a merged image of the surgical system of FIG. 43 from the perspective of the endoscope.

As illustrated in FIG. 43a, the location of the first interaction location 3244 is coordinated with the location of a second interaction location 3246 so that the first interaction location 3244 abuts the second interaction location 3246. The controller 3230 can provide a merged image shown on the display 3234, where a second interaction location 3246 is depicted in relation to the tumor 3040 and the first interaction location 3244 as a representation of the intended interaction location of the surgical instrument 3218. In this illustrated embodiment, the second interaction location 3246 corresponds to an incision to open the stomach 3000 after a portion of the stomach has been flip procedure in order to remove the tumor 3040 from the stomach 30 laparoscopically.

Due to this coordination and alignment of the first interaction location 3244 and the second interaction location 3246, there is minimal damage to the surrounding tissue of the stomach 3000 when incisions are created using the interaction locations 3244, 3246 as guides. The second interaction location 3246 is able to be placed at the exact location of the tumor 3040, even though the tumor is not visible from the laparoscopic side. Due to the endoscope 3202 being able to visualize the tumor, and communicate with the controller 3230. In the illustrated embodiment, the interaction locations 3244, 3246 are shown in dashed outlines. However, other forms of representative depictions, such as simple geometric shapes, can be used.

Figure 44A:
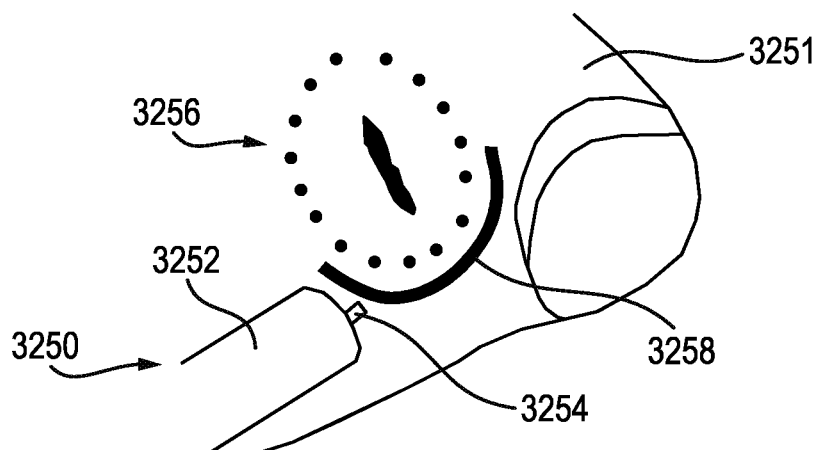
FIG. 44a is a detailed view of another embodiment of a surgical system, showing the removal of a damaged portion of tissue from a colon.

In some embodiments, coordination of lesion removal can be effected with externally supported orientation control via laparoscopic instruments or retractors. Alternatively, or in addition, coordination of lesion removal can be effected with internally supported balloon orientation control closure. For example, a surgical systems 3150 that is configured for lesion removal using an endoscopic and laparoscopic approach, in combination with an endoscopically supported balloon is illustrated in FIG. 44a, can be provided. This is an alternate procedure that has both intra luminal and extra luminal interactive operations. The submucosal dissection and separation is done within the colon. The dissection is stopped before full perimeter dissection is done. An incision is then made in the colon wall and the tumor flipped out into the extra luminal space. The endocutter is the brought into both seal/transect the tumor from the remaining attachment and to close the incision defect. This is done to minimize invasiveness and trauma and seal and remove the tumor since it is not really able to be done entirely intraluminal. This requires the same cooperation and interaction from devices and landmarks on both side of an organ wall that is only viewable from one side at a time.

Figure 44B:
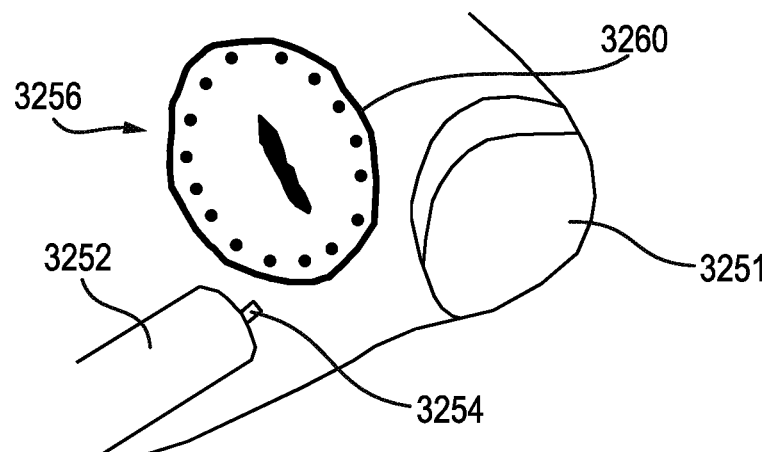
FIG. 44b is a detailed view of the surgical system of FIG. 44a, showing an incision in the seromuscular layer.
Figure 44C:
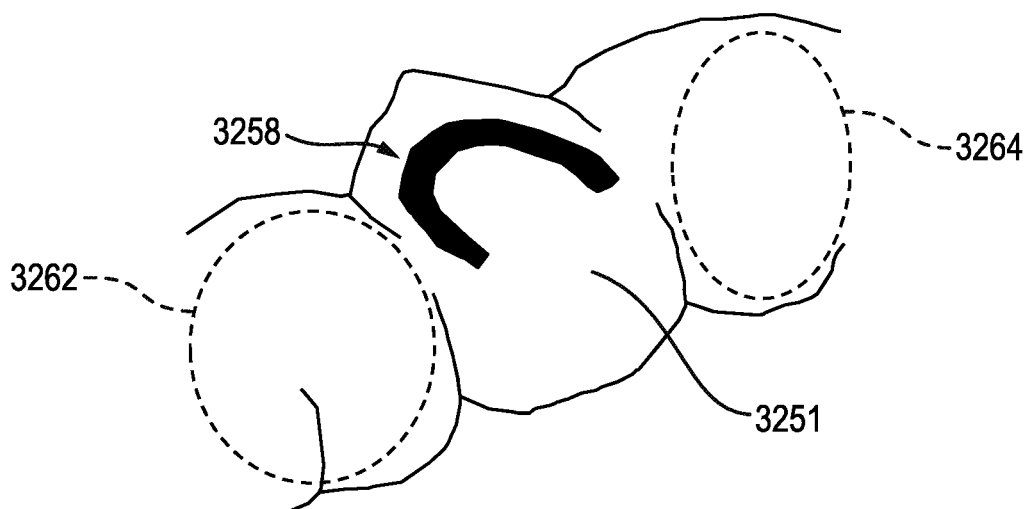
FIG. 44c is a detailed view of the surgical system of FIG. 44b, showing an endoscopic balloon inflation.
Figure 44D:
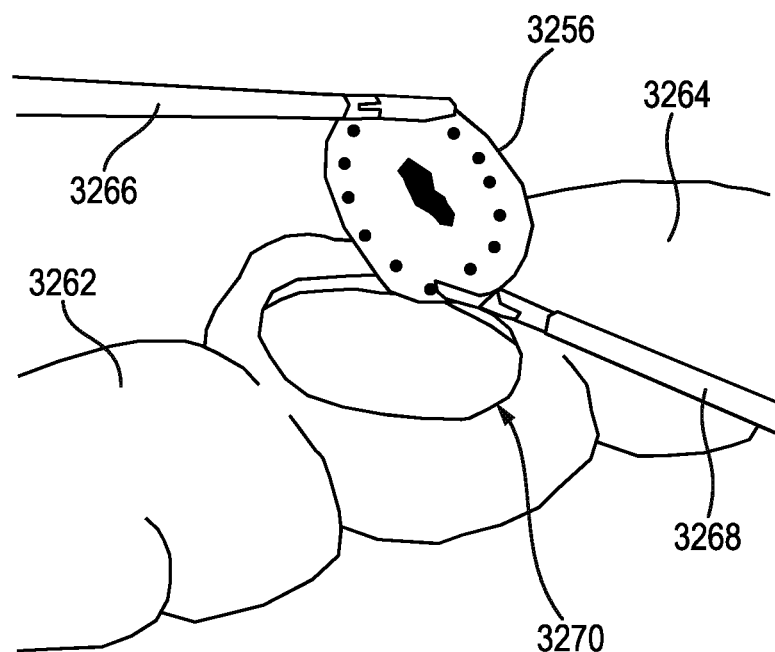
FIG. 44d is a detailed view of the surgical system of FIG. 44c, showing a lesion removal.
Figure 44E:
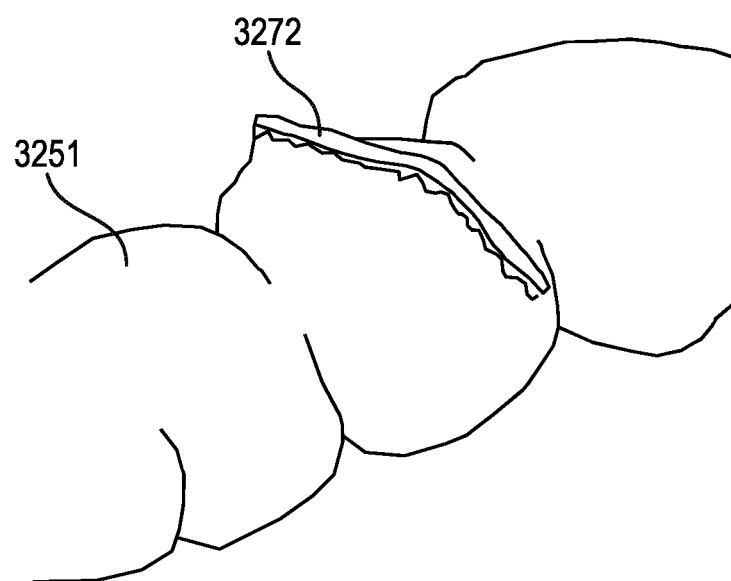
FIG. 44e is a detailed view of the surgical system of FIG. 44d, showing a sealing of the colon.

The surgical system 3150 includes a surgical instrument 3152 having a cutting tip 3154. The cutting tip 3154 is arranged at the distal end of the surgical instrument 3152. As illustrated in FIG. 44a, an initial mucosal incision 3158 can be made in the colon 3151 from the endoscopic side by the surgical instrument 3152. The mucosal incision 3158 is made around the lesion 3156 in order to prepare the lesion 3156 for removal, with the mucosal incision 3158 being only partially around the lesion 3156. As illustrated in FIG. 44b, an incision 3160 can be made in the seromuscular layer of the colon 3151 completely around the lesion 3156 after the mucosal incision 3158 is made. As illustrated in FIG. 44c, balloons 3162, 3164 are endoscopically arranged on either side of the area of the colon 3151 where the lesion 3156 is located. Even though not shown in the FIG. 44a and FIG. 44b, the balloons 3162, 3164 are present and inflated during the creation of the mucosal incision 3158 and the seromuscular incision 3160. The balloons 3162, 3164 provide tension to the colon 3151 to allow for a cleaner incision, and also reduce the likelihood that the lesion 3156 will contact the contents of the colon 3151 during removal through the "crown method." As illustrated in FIG. 44d, with the mucosal incision 3158 and the seromuscular incision 3160, the lesion 3156 can be removed by laparoscopically arranged instruments 3166, 3168. With the lesion 3156 removed, the hole 3170 left by the removal can be stapled closed by staples 3172, as illustrated in FIG. 44e.

Coordinated Instrument Control Systems

Surgical systems that allow for coordinated imaging, such as the surgical systems described above, can also include coordination of the instruments at a specific step of an operation. Since the surgical systems can provide images of both the intraluminal space and the extraluminal space, certain surgical steps which require both endoscopic and laparoscopic coordination with a known surgical site can be performed.

The surgical systems include surgical imaging systems described above, which can be used to track and locate various scopes and instruments arranged on opposite sides of a tissue wall, and provide a merged image. Since the merged image shows the orientation and location of instruments and scopes arranged on opposite sides of a tissue wall which are not visible to each scope, the instruments can be arranged on either side of the tissue wall in order to coordinate motion of the instruments from either side of the tissue wall.

For a surgical procedure, there may be a surgical step which requires coordination between instruments arranged endoscopically and laparoscopically. For example, during a procedure to remove a tumor from a stomach, an incision must be made laparoscopically to access the tumor, and then the tumor must be passed from the intraluminal space to the extraluminal space for removal. However, the endoscopically arranged instruments and the laparoscopically instruments used to pass the tumor through the incision cannot visually see the each other while the handoff is occurring. However, in combination with the imaging systems of the endoscope and laparoscope, the instruments can be coordinated to align with the incision in the stomach wall to pass the tumor through the incision since the instruments can be visualized through the stomach wall.

In one exemplary embodiment, the surgical system can include a first scope device configured to transmit image data of a first scene. Further, a second scope device is configured to transmit image data of a second scene, the first scene being different than the second scene. A tracking device is associated with one of the first scope device or the second scope device and configured to transmit a signal indicative of a location of one of the first scope device or the second scope device relative to the other one of the first scope device or the second scope device. A first surgical instrument is configured to interact with an internal side of a target tissue structure. A second surgical instrument is configured to interact an external side of the target tissue structure. A controller is configured to receive the transmitted image data and transmitted signal. Based on the transmitted signal and image data, the controller can determine on a first relative distance from the first scope device to the second scope device, a second relative distance from the first scope device to the first surgical instrument positioned within at least one natural body lumen and organ, and a third relative distance from the second scope to the second surgical instrument positioned outside of at least one natural body lumen and the organ. Relative movements of the instruments are coordinated based on the determined relative distances.

The controller is further configured to generate a merged image of the first and second scenes. The controller receives the actual depiction from each of the first imaging system and second imaging system. The actual depiction can be a photo or a live video feed of what each of the imaging systems, which are attached to each of the scope devices, are seeing in real time. Each of the first and second scenes depict certain critical structures that are not visible by the other imaging system. For example, the first imaging system, arranged endoscopically, can have a tumor and a surgical instrument within its field of view. Additionally, the second imaging system can include laparoscopic instruments arranged within its field of view. Further, as will be discussed in more detail, the merged image facilitates coordination of the relative movements of both endoscopic and laparoscopic instruments at a surgical site.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with a stomach, a person skilled in the art will appreciate that these surgical systems can be used in connection with any other suitable natural body lumens or organs.

Figure 45:
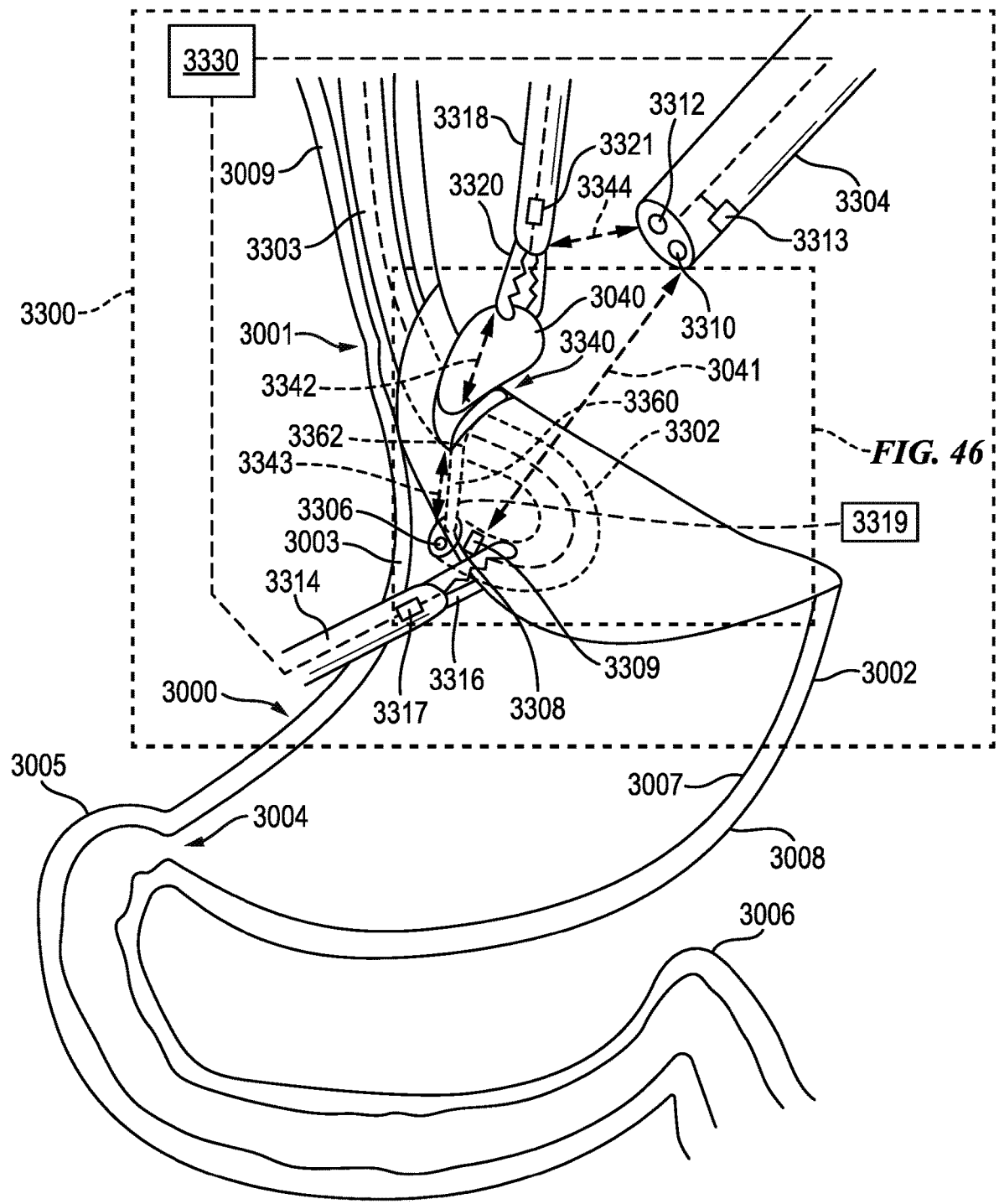
FIG. 45 is a schematic view of another embodiment of a surgical system, showing a removal of a tumor from a stomach by a laparoscopically arranged instrument.

FIG. 45 illustrates an exemplary embodiment of a surgical system 3300 that is configured for endoluminal access into and laparoscopic access of the stomach 3000. Aside from the differences described in detail below, the surgical system 3300 can be similar to surgical system 3100 (FIG. 37 and FIG. 38) and therefore common features are not described in detail herein. For purposes of simplicity, certain components of the surgical system 3300 and the stomach 3000 are not illustrated.

As shown, the stomach 3000 includes an esophageal sphincter 3001, a greater curvature 3002, a lesser curvature 3003, a pyloric sphincter 3004, a duodenum 3005, and a duodenojejunal flexure 3006. Additionally, the stomach includes an inner tissue wall 3007, and an outer tissue wall 3008. As illustrated, the stomach 3000 includes a tumor 3040 arranged on the greater curvature 3002. When operating on the stomach 3000, the blood vessels 3064 may need to be manipulated (e.g., mobilized), such as by using laparoscopically arranged instruments, to properly access the tumor 3040. In use, as described in more detail below, the surgical system 3200 can provide a merged image so that energy application and incisions in subsequent procedure steps can be coordinated and visualized.

The surgical system 3300 includes an endoscope 3302 configured for endoluminal access through the esophagus 3009 and into the stomach 3000. The endoscope 3302 can have a variety of configurations. For example, in this illustrated embodiment, the endoscope 3302 includes an optical sensor 3306 (e.g., a camera) and light element 3308. Further, the endoscope 3302 includes a working channel 3303 that is arranged along the length of the endoscope 3302. The working channel 3303 is configured to receive one or more surgical instruments and/or allow fluid to pass therethrough to insufflate a lumen or organ (e.g., the stomach). In some embodiments, the endoscope 3302 can include an outer sleeve (not shown) configured to be inserted through a patient's mouth (not shown) and into the esophagus 3009. The outer sleeve can include a working channel that is configured to allow the endoscope 3302 to be inserted through the outer sleeve and access the stomach 3000.

The surgical system 3300 also includes a laparoscope 3304 configured for laparoscopic access through the abdominal wall (not shown) and into the extraluminal anatomical space adjacent to the stomach 3000. The laparoscope 3304 can have a variety of configurations. For example, in this illustrated embodiment, the laparoscope 3304 includes an optical sensor 3310 (e.g., a camera) and lighting element 3312. Alternatively, or in addition, the laparoscope 3304 can include a working channel (not shown) arranged along the length of the laparoscope 3304 to pass an instrument laparoscopically into the extraluminal anatomical space. In some embodiments, the laparoscope 3304 can be inserted into the extraluminal anatomical space through a trocar or multi-port (not shown) positioned within and through a tissue wall. The trocar or multi-port can include ports for passing the laparoscope 3304 and/or other surgical instruments into the extraluminal anatomical space to access the stomach 3000.

The endoscope 3302 includes a tracking device 3309 arranged with the endoscope 3302. The tracking device 3309 is configured to transmit a signal indicative of a location of the endoscope 3302 relative to the laparoscope 3304. Additionally, laparoscope 3304 includes a tracking device 3313 associated with the laparoscope 3304. The tracking device 3313 is configured to transmit a signal indicative of a location of the laparoscope 3304 relative to the endoscope 3302. In some embodiments, the tracking devices 3309, 3313 are configured to use magnetic or radio frequency sensing to detect a location and orientation of the endoscope 3302 and laparoscope 3304 arranged opposite sides of the tissue wall of the stomach 3000. Alternatively, the tracking devices 3309, 3313 are configured to use common anatomic landmarks to detect a location and orientation of the endoscope 3302 and laparoscope 3304 arranged opposite sides of the tissue wall of the stomach 3000. The tracking devices 3309, 3313 can determine a relative distance represented by dashed arrow 3341, which is indicative of the location of one of the endoscope 3302 and laparoscope 3304 relative to the other scope device.

In some embodiments, the first and second tracking devices 3309, 3313 are configured to use magnetic or radio frequency sensing to detect a location, an orientation, or both, of the endoscope 3302 and laparoscope 3304, respectively (e.g., when the endoscope 3302 and laparoscope 3304 positioned on opposite sides of the tissue wall of the stomach 3000). Alternatively, the first and second tracking devices 3309, 3313 are configured to use common anatomic landmarks to detect a location, an orientation, or both, of the endoscope 3302 and laparoscope 3304, respectively (e.g., when the endoscope 3302 and laparoscope 3304 positioned on opposite sides of the tissue wall of the stomach 3000). The first and second tracking devices 3309, 3313 can each transmit the signal(s) to a controller (like controller 3330). Various embodiments of magnetic fiducial markers and using magnetic fiducial markers in detecting location are discussed further, for example, in U.S. Pat. App No. 63/249,658 entitled "Surgical Devices, Systems, And Methods For Control Of One Visualization With Another" filed on Sep. 29, 2021.

As shown in FIG. 45, the surgical system 3300 includes a surgical instrument 3360 that passes through the working channel 3303 of the endoscope 3302 and into the stomach 3000. While the surgical instrument can have a variety of configurations, in this illustrated embodiment, the surgical instrument 3360 includes graspers 3362 at a distal end thereof. A person skilled in the art will appreciate that the type of surgical instrument and the structural configuration of the surgical instrument, including the end effector, depends at least upon the surgical site and the surgical procedure to be performed. While only one surgical instrument 3360 is illustrated, in other embodiments, the surgical system 3300 can include more than one surgical instrument arranged in the working channel of the endoscope.

As further shown in FIG. 45, the surgical instrument 3360 includes a force sensor 3319 (e.g., the force sensor 3319 can be coupled to one or more motors (not shown) of the instrument 3360 or of a robotic arm (not shown) that is coupled to the instrument 3360). During use, the force sensor 3319 is configured to sense the amount of force being applied by the graspers 3362 to the tissue of the stomach 3000 as the graspers 3362 manipulate the tissue. The force sensor 3319 is further configured to transmit the force data to a controller 3330 of the surgical system 3300. The controller 3330 can aggregate the received feedback input(s) (e.g., force data), perform any necessary calculations, and provide output data to effect any adjustments that may need to be made (e.g., adjust power level, advancement velocity, etc.). Additional details on the force sensor 3319 and controller 3330 are further described in previously mentioned U.S. Pat. No. 10,856,928, which is incorporated herein by reference in its entirety. In some embodiments, the force sensor 3319 can be omitted.

The surgical system 3300 includes first and second surgical instruments 3314, 3318 that are each configured for laparoscopic access through the abdominal wall and into the extraluminal anatomical space surrounding the stomach 3000. The first and second surgical instruments 3314, 3318 can have a variety of configurations. For example, in this illustrated embodiment, the surgical instruments 3314, 3318 include graspers 3316, 3320, respectively. While two surgical instruments 3314, 3318 are illustrated, in other embodiments, the surgical system 3300 can include more than two surgical instruments. The surgical instruments 3314, 3318 are configured to be inserted through the abdominal wall and into the extraluminal space to manipulate and/or operate on the stomach 3000 from the laparoscopic side. In some embodiments, the first and second surgical instruments 3314, 3318 can be passed through ports of the same trocar and/or multi-port device that the laparoscope 3304 is positioned therethrough.

The surgical instrument 3314 includes a force sensor 3317 arranged with the surgical instrument 3314. The force sensor 3317 is configured to sense an applied force to the target tissue structure by the surgical instrument 3314. Additionally, the surgical instrument 3318 includes a force sensor 3321 arranged with the surgical instrument 3318. The force sensor 3321 is configured to sense an applied force to the target tissue structure by the surgical instrument 3318. The controller 3330 is further configured to determine an amount of strain that is applied to the stomach 3000 by at least one of the surgical instruments 3314, 3318 via the force sensors 3317, 3321.

As stated above, the endoscope 3302 includes the optical sensor 3306. The optical sensor 3306 is configured to transmit image data of a first scene within a field of view of the endoscope 3302 to the controller 3330. As shown in FIG. 45, the surgical instrument 3340 is inserted into the working channel of the endoscope 3302 and advanced towards the tumor 3040. In conventional surgical systems, a surgeon would perform a partial stomach flip blindly (e.g., using only the laparoscopic scene) to remove the tumor 3040 laparoscopically through an incision in the stomach wall. The surgeon is not able to coordinate the endoscopic and laparoscopic instruments accurately, and instead approximates the location of the tumor and instruments during the stomach flip, potentially leading to inaccurate removal of the tumor and the removal more tissue than needed. However, in the present system 3300, since both the endoscope 3302 and laparoscope 3304 can provide image data of the surgical site from both the intraluminal anatomical space and the extraluminal anatomical space, the handoff of the tumor through the incision from the intraluminal space to the extraluminal space can be coordinated between both sets of instruments.

As shown in FIG. 45, the endoscope 3302 can determine the location of the tumor 3040 and incision 3340 based on the relative distance 3343, and the location of the surgical instrument 3360, which is sensed by the optical sensor 3306 and determined by the controller 3330. In some embodiments, the relative distance 3343 is determined using structured light projected onto the tumor 3040 and/or surgical instrument 3360 and tracked by the optical sensor 3306. Additionally, the laparoscope 3304 includes the optical sensor 3310. The optical sensor 3310 is configured to transmit image data of a second scene within a field of view of the laparoscope 3304. The surgical instruments 3314, 3318 are arranged within the field of view of the laparoscope 3304. As shown in FIG. 45, the laparoscope 3304 can determine the location of the surgical instruments 3318 based on the relative distance 3344, which is measured by the optical sensor 3310 and determined by the controller 3330. In some embodiments, the relative distance 3344 is determined by using structured light projected onto the surgical instrument 3318 and tracked by the optical sensor 3310.

The surgical system 3300 also includes a controller 3330 communicatively coupled to the endoscope 3302 and the laparoscope 3304. The controller 3330 is configured to receive the transmitted image data of the first and second scenes from the optical sensors 3306, 3310. The controller 3330 is also configured to determine, based on the transmitted signals, a relative distance from the endoscope 3302 to the laparoscope device 3304 represented by dashed arrow 3341, a relative distance from the tumor 3040 to the surgical instrument 3318 represented by dashed arrow 3342, a relative distance from the endoscope 3302 to the tumor 3040 represented by dashed arrow 3343, and a relative distance from the laparoscope 3304 to the surgical instrument 3318 positioned outside of at least one natural body lumen and the organ represented by dashed arrow 3344.

Figure 46:
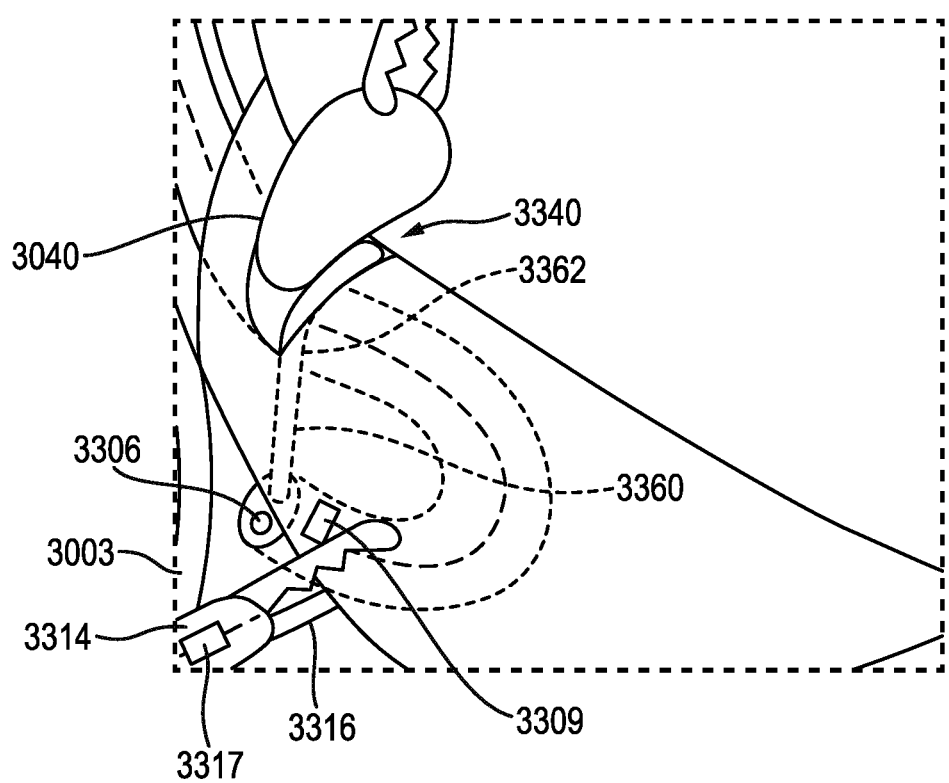
FIG. 46 is a schematic view of a merged image of the surgical system of FIG. 45 from the perspective of the laparoscope.

As illustrated in FIG. 46, based on the determined relative distances, a merged image is provided by the controller 3330 to depict the scene within the field of view of the laparoscope 3304, while also overlaying a representative depiction of the objects arranged only within view of the endoscope 3302 such as the tumor and the surgical instrument 3360. The optical sensor 3310 has the surgical instruments 3314, 3318 and the outer tissue wall 3007 in its field of view, and cannot visually detect the tumor 3040, endoscope 3302, or the surgical instrument 3360.

The controller 3330 is configured to provide a merged image to a display. The displays can be configured in a variety of configurations. For example, in some embodiments, a first display can be configured to display the first scene and a second display can be configured to display the second scene, and the first display, the second display, or both, can be further configured to display the merged image. In another embodiment, the surgical system 3300 can include, a third display that can be used to display the merged image, and the first and second displays are used to only show the transmitted image data from the first and second optical sensors 3306, 3310, respectively, without any modification. In this embodiment, a surgeon can access the real-time scenes from both the endoscope 3302 and the laparoscope 3304 on the first and second displays while also having access to the merged image on the third display.

Based on the relative distances 3341, 3342, 3343, 3344 determined by the controller 3330, the controller 3330 can provide the merged image from the point of view of the laparoscope 3304, where the endoscope 3302 and the surgical instrument 3360 are shown as representative depictions which correspond to their location in the intraluminal space in real-time. In the illustrated embodiment, the representative depictions are shown in dashed outlines of the endoscope 3302 and surgical instrument 3360. However, other forms of representative depictions can be used, such as simple geometric shapes to represent the non-visual instruments and anatomical structures within the intraluminal space. By using the merged image, a surgeon can arrange the surgical instruments in a proper position in order to operate on the stomach 3000. With the mobilized tumor 3040 produced in the merged image, along with the endoscope 3302 and surgical instrument 3360, the surgical instrument 3360 can be coordinated through movement commands input by a user to align the partially removed tumor 3040 with the incision made in the stomach wall. The surgical instrument 3318 can also be coordinated through movement commands input by the user to align the surgical instrument 3318 with the incision 3340 on the laparoscopic side. As such, when the tumor 3040 is at least partially passed through the incision 3340 by the surgical instrument 3360 from the intraluminal space to the extraluminal space, the surgical instrument 3318 can grasp the tumor 3040 and aid in removing the tumor 3040 from the stomach 3000.

In use, the controller 3330 can be configured to restrict movement of the surgical instrument 3314 and the surgical instrument 3318 relative to each other at the target tissue structure (e.g., tumor 3040) based on the transmitted image data of the first and second scenes and the relative distances 3341, 3342, 3342 through the robotic arms which the surgical instruments are attached to.

Figure 47:
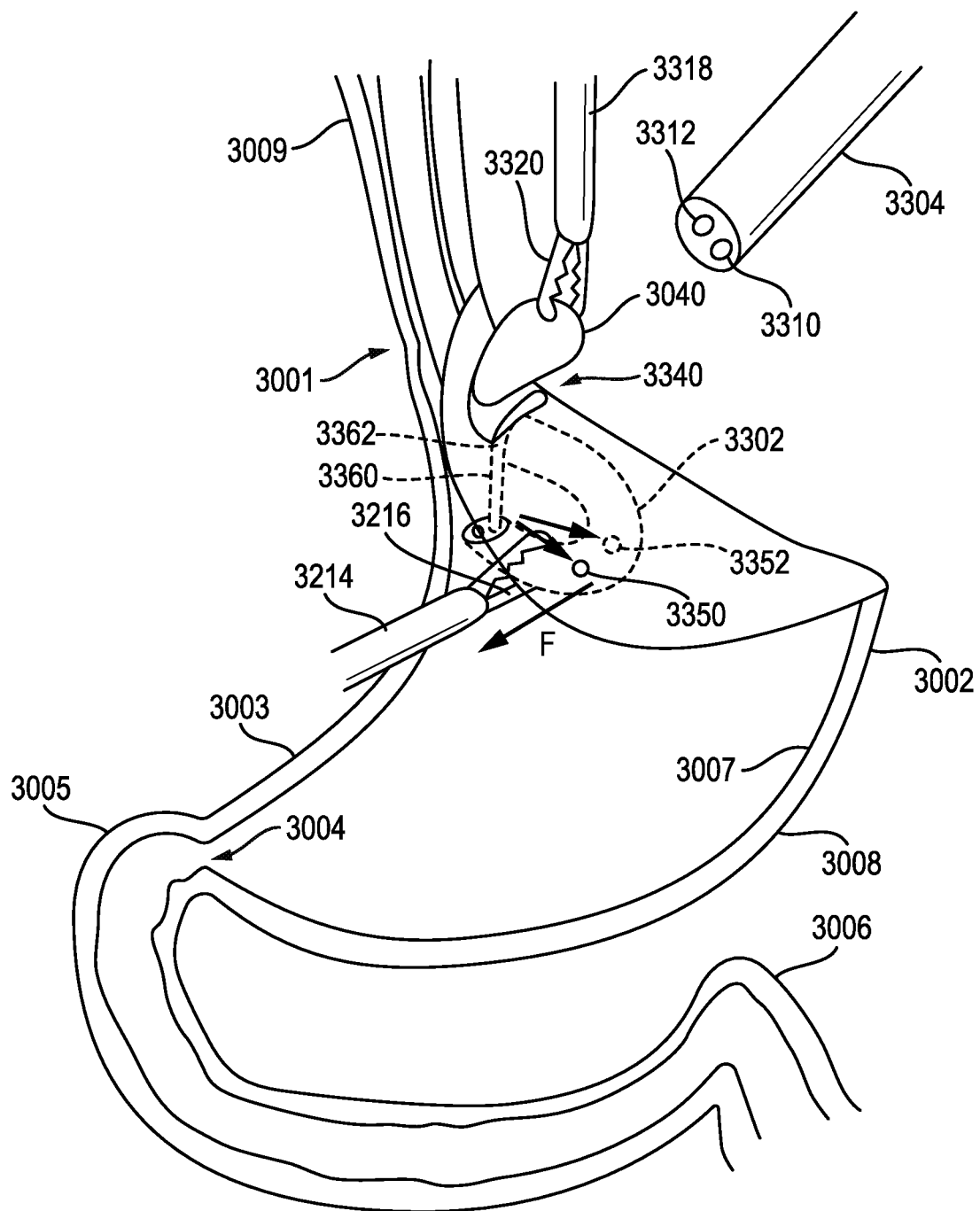
FIG. 47 is a schematic view of the surgical system of FIG. 45, showing a tissue strain measurement using markers arranged on the inner tissue surface of the stomach.

As illustrated in FIG. 47, the controller 3330 is further configured to determine an amount of strain that is applied to the stomach 3000 by at least one of the surgical instruments 3314, 3318 with the use of visual markers 3350, 3352 associated with the stomach 3000. The visual markers 3350, 3352 are at least one of one or more local tissue markings on the stomach 30, one or more projected light markings on the stomach 3000, or one or more anatomical aspects of at least one of the stomach 3000. The visual markers 3350, 3352 are detected by the optical sensor 3306 of the endoscope 3302 or the optical sensor 3310 of the laparoscope 3304. In use, the optical sensor 3306 or optical sensor 3310 senses the movement of the visual marker 3350 as it transitions to the visual marker 3352.

Figure 48:
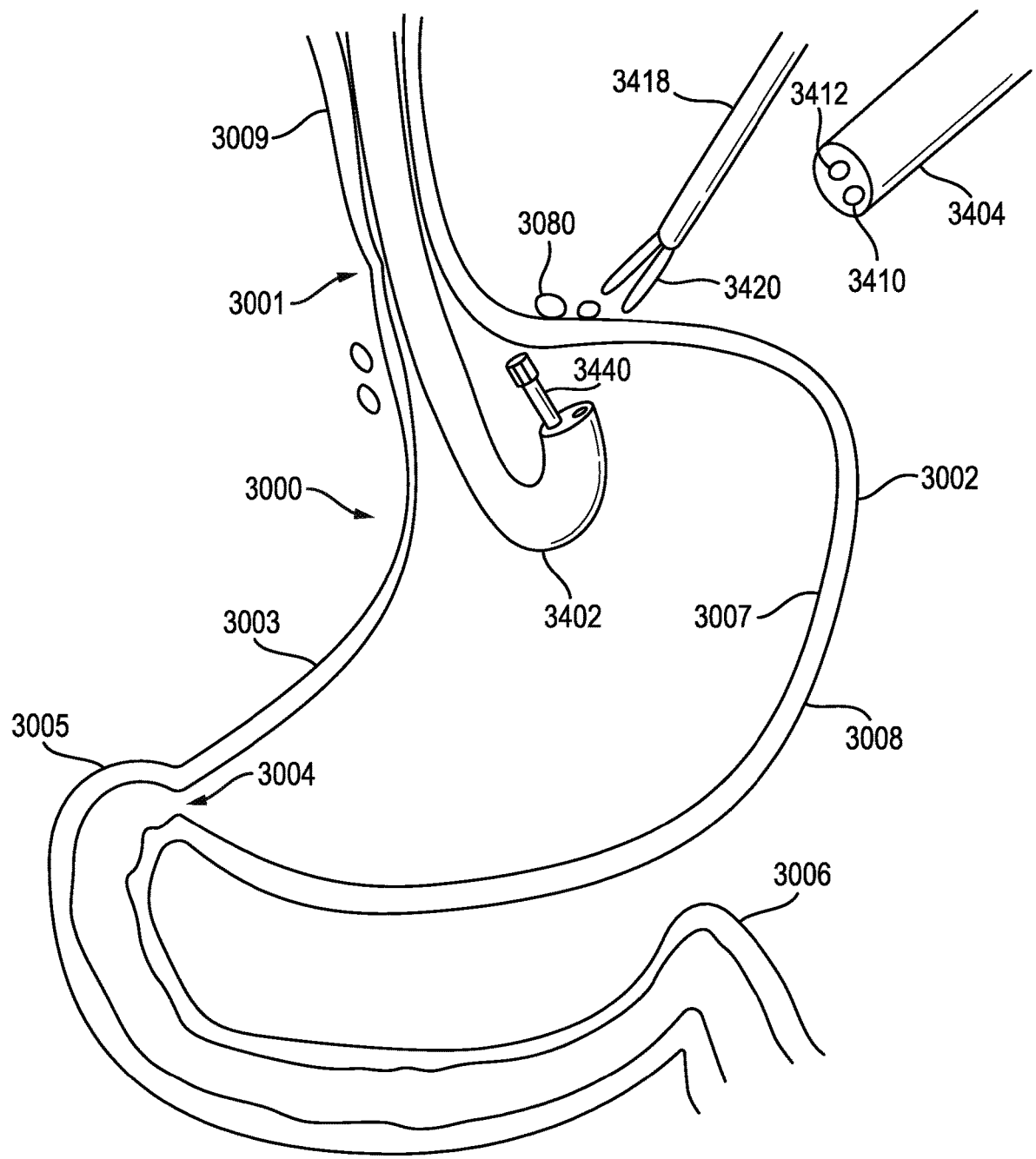
FIG. 48 is a schematic view of another embodiment of a surgical system, showing the removal of lymph nodes from the outer tissue wall of a stomach.

As illustrated in FIG. 48, the surgical system 3400 can be used for optical temperature sensing methods in order to sense the external temperature of the stomach 3000 while an ablation is occurring internally to ensure that certain layers of the stomach 3000 are not damaged. Aside from the differences described in detail below, the surgical system 3400 can be similar to surgical system 3300 (FIG. 45) and therefore common features are not described in detail herein. The temperature monitoring methods can be used to restrict the application of energy by an energy applying surgical instrument 3440 endoscopically. For example, an energy applying surgical instrument 3440 is endoscopically arranged through the endoscope 3402. Additionally, a laparoscope 3404 and a surgical instrument 3418 are laparoscopically arranged in the extraluminal space. The laparoscope 3404 includes an optical sensor 3410 and a light 3412.

In use, in order to remove lymph nodes 3080, the energy applying surgical instrument 3440 can apply an energy to the internal wall 3007 of the stomach 3000. The laparoscopically arranged surgical instrument 3418 can be arranged to grasp the lymph nodes 3080. As the energy applying instrument applies energy to the lymph nodes, the optical sensor 3410 can detect the temperature of the tissue of the stomach 3000, and reduce the amount of energy applied if the temperature becomes too high in order to prevent tissue damage.

In some embodiments, the surgical system 3400 can be used for control of mid-thickness ablation (e.g., thermal, electrical, or microwave) controlled by one imaging access system by coordinating it with a second system viewing from a different point-of-view, similar to surgical system 3000. Additionally, after removal of a tumor, the final ablation from the endoscopic side could be used to expand the margin around the site of the tumor to insure complete removal of the cancer. For example, where a cancerous tumor is close to the esophageal sphincter, maintenance of the sphincter is important to preventing acid reflux from occurring and thus it is useful to maintain as much healthy tissue as possible avoid unnecessary expansive dissection and resection.

The surgical systems disclosed herein can be designed to be disposed of after a single use, or they can be designed to be used multiple times. In either case, however, the surgical systems can be reconditioned for reuse after at least one use. Reconditioning can include any combination of the steps of disassembly of the surgical systems, followed by cleaning or replacement of particular pieces and subsequent reassembly. In particular, the surgical systems can be disassembled, and any number of the particular pieces or parts of the surgical systems can be selectively replaced or removed in any combination. Upon cleaning and/or replacement of particular parts, the surgical systems can be reassembled for subsequent use either at a reconditioning facility, or by a surgical team immediately prior to a surgical procedure. Those skilled in the art will appreciate that reconditioning of a surgical systems can utilize a variety of techniques for disassembly, cleaning/replacement, and reassembly. Use of such techniques, and the resulting reconditioned instrument, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. It will be appreciated that the terms "proximal" and "distal" are used herein, respectively, with reference to the top end (e.g., the end that is farthest away from the surgical site during use) and the bottom end (e.g., the end that is closest to the surgical site during use) of a surgical instrument, respectively. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A surgical system, comprising:
   a first scope device configured to be at least partially disposed within at least one of a natural body lumen and an organ and configured to transmit image data of a first scene within a field of view of the first scope device;
   a second scope device configured to be at least partially disposed outside of the at least one of the natural body lumen and the organ and to transmit image data of a second scene within a field of view of the second scope device, the second scene being different than the first scene;
   a tracking device associated with one of the first scope device or the second scope device and configured to transmit a signal indicative of a location of the one of the first scope device or the second scope device relative to the other one of the first scope device or the second scope device; and
   a controller configured to receive (i) the transmitted image data of the first and second scenes and (ii) the transmitted signal, to determine, based on the transmitted signal, a relative distance between the first scope device and the second scope device, and to provide, based on the transmitted image data and relative distance between the first and second scopes, a merged image of at least a portion of at least the first scope device and the second scope device in a single scene, wherein at least one of the first scope device and the second scope device in the merged image is a representative depiction thereof.

2. The surgical system of claim 1, wherein the first scope device and the second scope device are each illustrated as a representative depiction thereof in the merged image.

3. The surgical system of claim 1, further comprising a first display that is configured to display the first scene and a second display that is configured to display the second scene.

4. The surgical system of claim 3, wherein at least one of the first display and the second display is further configured to display the single scene.

5. The surgical system of claim 3, further comprising a third display that is configured to display the single scene.

6. The surgical system of claim 1, wherein the first scope device is an endoscope and the second scope device is a laparoscope.

7. The surgical system of claim 1, wherein the first scene does not include the second scope device, and wherein the second scene does not include the first scope device.

8. The surgical system of claim 1, wherein the tracking device is associated with the first scope device.

9. The surgical system of claim 1, wherein the tracking device is associated with the second scope device.

10. The surgical system of claim 1, wherein the signal is further indicative of an orientation of the first scope device within one of the natural body lumen and the organ relative to the second scope device, and wherein the controller is further configured to determine, based on the transmitted signal, a relative orientation of the first scope device.

11. The surgical system of claim 1, wherein the signal is further indicative of an orientation of the second scope device positioned outside of the at least one of the natural body lumen and the organ relative to the first scope device, and wherein the controller is further configured to determine, based on the transmitted signal, a relative orientation of the second scope device.

12. The surgical system of claim 1, the controller is further configured to determine, based on at least the transmitted image data, at least one of a location and an orientation of at least one instrument positioned outside of the at least one natural body lumen and the organ relative to the first scope device, wherein at least a portion of the at least one instrument is illustrated as an actual depiction or representative depiction thereof in the merged image.

13. Surgical system of claim 1, wherein the controller is further configured to (i) receive an additional signal that is indicative of at least one of a location and an orientation of at least one instrument positioned outside of the at least one natural body lumen and the organ relative to the second scope device, (ii) to determine, based on the transmitted additional signal, at least one of a relative location and a relative orientation of the at least one instrument, wherein at least a portion of the at least one instrument is illustrated as an actual depiction or representative depiction thereof in the merged image.

14. A method, comprising:
 transmitting, by a first scope device, image data of a first scene within a field of view of the first scope device while at least a portion of the first device is positioned within at least one of a natural body lumen and an organ;
 transmitting, by a second scope device, image data of a second scene within a field of view of the second scope device while the second scope device is positioned outside of the at least one of the natural body lumen and the organ, the second scene being different than the first scene;
 transmitting, by a tracking device, a signal indicative of a location of one of the positioned first scope device or second scope device relative to the other positioned first scope device or second scope device;
 receiving, by a controller, the transmitted image data of the first and second scenes and the transmitted signals of the location of the first and second scope devices;
 determining, by the controller and based on the transmitted signal, a relative distance between the first scope device and the second scope device; and
 generating, by the controller and based on the transmitted image data and the relative distance between the first and second scope devices, a merged image of at least a portion of at least the first scope device and the second scope device in a single scene, wherein at least one of the first scope device and the second scope device in the single scene is a representative depiction thereof.

15. The method of claim 14, further comprising:
 illustrating a representative depiction of the first scope device in the merged image; and
 illustrating a representative depiction of the second scope device in the merged image.

16. The method of claim 14, further comprising:
 displaying the first scene on a first display; and
 displaying the second scene on a second display.

17. The method of claim 14, further comprising displaying the single scene on at least one of the first display and the second display.

18. The method of claim 14, further comprising displaying the single scene on a third display.

19. The method of claim 14, further comprising transmitting, by the tracking device, a signal indicative of an orientation of the one of the first scope device or the second scope device relative to the other one of the first scope device or the second scope device.

20. The method of claim 14, further comprising:
 determining, by the controller and based on the transmitted image data, at least one of a position and an orientation of at least one or more instruments positioned outside of the at least one natural body lumen and the organ relative to the first scope device.

* * * * *